United States Patent
Schunk et al.

(10) Patent No.: US 8,404,740 B2
(45) Date of Patent: *Mar. 26, 2013

(54) SPIROCYCLIC CYCLOHEXANE COMPOUNDS

(75) Inventors: Stefan Schunk, Aachen (DE); Saskia Zemolka, Aachen (DE); Derek Saunders, Aachen (DE); Michael Gruss, Aachen (DE); Heinz Graubaum, Berlin (DE)

(73) Assignee: Gruenenthal GmbH, Aachen (DE)

( * ) Notice: Subject to any disclaimer, the term of this patent is extended or adjusted under 35 U.S.C. 154(b) by 792 days.

This patent is subject to a terminal disclaimer.

(21) Appl. No.: 12/545,461

(22) Filed: Aug. 21, 2009

(65) Prior Publication Data

US 2010/0048554 A1    Feb. 25, 2010

Related U.S. Application Data

(63) Continuation of application No. PCT/EP2008/001270, filed on Feb. 19, 2008.

(30) Foreign Application Priority Data

Feb. 22, 2007    (DE) .................... 10 2007 009 235

(51) Int. Cl.
*A61K 31/35* (2006.01)
*A61K 31/382* (2006.01)
*C07D 335/04* (2006.01)
*C07D 209/54* (2006.01)

(52) U.S. Cl. ......... 514/437; 514/449; 514/451; 549/16; 549/339; 549/359; 548/408

(58) Field of Classification Search ............ 549/16, 549/339, 359; 514/437, 449, 451; 548/408
See application file for complete search history.

(56) References Cited

U.S. PATENT DOCUMENTS

| | | | |
|---|---|---|---|
| 3,328,412 | A | 6/1967 | Atkinson et al. |
| 4,291,039 | A | 9/1981 | Van Dyke, Jr. et al. |
| 4,575,508 | A | 3/1986 | Steiner et al. |
| 5,328,905 | A | 7/1994 | Hamminga et al. |
| 5,631,265 | A | 5/1997 | Audia et al. |
| 5,760,051 | A | 6/1998 | Audia et al. |
| 5,869,691 | A | 2/1999 | Audia et al. |
| 7,332,519 | B2 | 2/2008 | Hinze et al. |
| 7,485,634 | B2 | 2/2009 | Martin et al. |
| 7,547,707 | B2 | 6/2009 | Hinze et al. |
| 7,595,311 | B2 | 9/2009 | Busch et al. |
| 2005/0192333 | A1 | 9/2005 | Hinze et al. |
| 2006/0004034 | A1 | 1/2006 | Hinze et al. |
| 2006/0235012 | A1 | 10/2006 | Davidson et al. |
| 2007/0149557 | A1 | 6/2007 | Collins et al. |
| 2008/0125475 | A1 | 5/2008 | Linz et al. |
| 2008/0221141 | A1 | 9/2008 | Friderichs et al. |
| 2008/0280942 | A1 | 11/2008 | Diaz-Fernandez et al. |
| 2009/0042866 | A1 | 2/2009 | Lennox et al. |
| 2009/0326218 | A1 | 12/2009 | Martin et al. |

FOREIGN PATENT DOCUMENTS

| | | |
|---|---|---|
| DE | 102 52 667 A1 | 5/2004 |
| DE | 103 60 792 A1 | 7/2005 |
| DE | 10 2005 016 460 A1 | 10/2006 |
| GB | 1055203 A | 1/1967 |
| WO | WO 2004/043967 A1 | 5/2004 |
| WO | WO 2006/108565 A1 | 10/2006 |
| WO | WO 2008/009415 A2 | 1/2008 |

OTHER PUBLICATIONS

Fuad A. Abdulla et al., "Axotomy Reduces the Effect of Analgesic Opioids Yet Increases the Effect of Nociceptin on Dorsal Root Ganglion Neurons", The Journal of Neuroscience, Dec. 1, 1998, 18(23): 9685-9694.

Anthony L. Beck et al., "Synthesis of 3,4-Bridged Indoles by Photocyclisation Reactions. Part 2.[1] Photocyclisation of Halogenoacetyl Tryptophol Derivatives and α-Chloro Indol-3-ylalkanoate Esters", J. Chem. Soc. Perkin Trans. 1, pp. 813-821, 1992.

Girolamo Calo et al., "Pharmacology of nociceptin and its receptor: a novel therapeutic target", British Journal of Pharmacology (2000) 129, 1261-1283, Macmillan Publishers Ltd.

Simon J. Garden et al., "A versatile synthetic methodology for the synthesis of tryptophols", Tetrahedron 58 (2002) 8399-8412, Pergamon.

Francois Jenck et al., "Orphanin FQ acts as an anxiolytic to attenuate behavioral responses to stress", Proc. Natl. Acad. Sci. USA, vol. 94, pp. 14854-14858, Dec. 1997, Neurobiology.

I. Jirkovsky et al., "Synthesis of 1,3,4,9-Tetrahydro-1-alkylthiopyrano [3,4-*b*] indole-1-acetic Acids. The Sulfur Isoster of Prodolic Acid", vol. 12, pp. 937-940, Ayerst Research Laboratories, Montreal, Quebec, Canada, Oct. 1975.

(Continued)

*Primary Examiner* — Rita Desai

(74) *Attorney, Agent, or Firm* — Crowell & Moring LLP

(57) ABSTRACT

Spirocyclic cyclohexane compounds corresponding to formula I

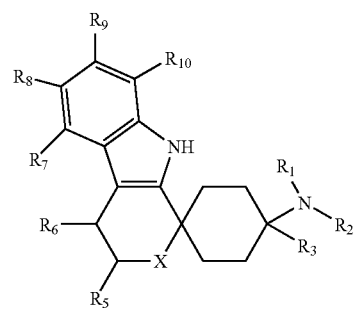

In which $R_1$, $R_2$, $R_3$ and $R_5$ through $R_{10}$ and X have defined meanings, a process for their preparation, pharmaceutical compositions containing such compounds, and the use of such spirocyclic cyclohexane compounds in the treatment and/or inhibition of pain and other conditions mediated by the ORL-1 or the μ-opioid receptor.

17 Claims, No Drawings

OTHER PUBLICATIONS

Michael A. King et al., "Spinal analgesic activity of orphanin FQ/nociceptin and its fragments", Neuroscience Letters 223 (1997) 113-116, Elsevier Science Letters.

Daniel Lednicer et al., "4-Amino-4-arylcyclohexanones and Their Derivatives, a Novel Class of Analgesics. 1. Modification of the Aryl Ring", The Upjohn Company, Research Laboratories, Kalamazoo, Michigan, Received Aug. 7, 1979.

Toshiya Manabe et al., "Facilitation of long-term potentiation and memory in mice lacking nociceptin receptors", Letters to Nature, vol. 394, pp. 577-581, Aug. 6, 1998, Macmillan Publishers Ltd.

Jean-Claude Meunier et al., "Isolation and structure of the endogenous agonist of opioid receptor-like $ORL_1$ receptor" Letters of Nature, vol. 377, pp. 532-535, Oct. 12, 1995.

J. S. Mogil et al., "Orphanin FQ is a Functional Anti-Opioid Peptide", Letter to Neuroscience, Neuroscience vol. 75, No. 2, pp. 333-337, 1996, Elsevier Science Ltd., Pergamon, Great Britain.

Miyuki Nishi et al., "Unrestrained nociceptive response and disregulation of hearing ability in mice lacking the nociceptin/orphaninFQ receptor", The EMBO Journal, vol. 16, No. 8, pp. 1858-1864, 1997, Oxford University Press.

Rainer K. Reinscheid et al., "Orphanin FQ: A Neuropeptide That Activates an Opioidlike G Protein-Coupled Receptor", Science, vol. 270, pp. 792-794, Nov. 3, 1995.

Van Bac et al., "New Strategy in the Stereocontrolled Synthesis of the Spiro Ketal Subunit of Milbemycins", Tetrahedron Letters, vol. 29, No. 23, pp. 2819-2822, 1988, Pergamon Press plc, Great Britain.

Bandini Marco et al., "$InBr_3$-Catalyzed Friedel-Crafts Addition of Indoles to Chiral Aromatic Epoxides: A Facile Route to Enantiopure Indolyl Derivatives", JOC Note, J. Org. Chem. 2002, 67, 5386-5389.

Peter D. Davis et al., "Inhibitors of Protein Kinase C. $1.^1$ 2,3-Bisarylmaleimides", J. Med. Chem. 1992, 35, 177-184.

D. Mark Cleave et al., "Synthesis and Antibacterial Activity of [6,5,5] and [6,6,5] Tricyclic Fused Oxazolidinones", Bioorganic & Medicinal Chemistry Letters 8 (1998) 1231-1236.

Katsuya Kato et al., "Synthesis of α-trifluoromethylated indoleacetic acid: a potential peroxidase-stable plant growth regulator", Journal of Fluorine Chemistry 99 (1999) 5-7.

Alan R. Katritzky et al., "The Chemistry of N-Substituted Benzotriazoles; Part 11. $^1$ The Preparation of Tertiary Amines Containing Tertiary-Alkyl Groups from Ketones, Secondary Amines, and Organometallic Reagents", Communications, Synthesis, pp. 66-69, Jan. 1989.

Alan H. Katz et al., "Synthesis and Analgesic Activity of Pemedolac (cis-1-Ethyl-1,3,4,9-tetrahydro-4-(phenylmethyl) pyrano[3,4-b]indole-1-acetic Acid)", J. Med. Chem. 1988, 31, 1244-1250.

Chunrong Ma et al., "Efficient Asymmetric Synthesis of Biologically Important Tryptophan Analogues via a Palladium-Mediated Heteroannulation Reaction", J. Org. Chem. 2001, 66, 4525-4542.

T. Sandmeyer, "Ueber Isonitrosoacetanilide und deren Kondensation zu Isatinen", The British Library, pp. 234-242.

Masafumi Yamagishi et al., "Biological Activities and Quantitative Structure-Activity Relationships of Spiro[imidazolidine-4,4'(1'H)-quinazoline]-2,2',5(3'H)-triones as Aldose Reductase Inhibitors", J. Med. Chem. 1992, 35, 2085-2094.

Tetsuro Shinada et al., "Facile Synthesis of 6-Hydroxyindole-3-acetic Acid: On the Structure of the Aromatic Subunit of Nephilatoxin-1-6", Tetrahedron Letters, vol. 37, No. 39, pp. 7099-7102, 1996, Great Britain.

Aeri Park et al., "New solid-state chemistry technologies to bring better drugs to market: knowledge-based decision making", Expert Opin. Drug Discov. (2007) 2(1), pp. 145-154.

Ali Ardati et al., "Interaction of [$^3$H] Orphanin FQ and $^{125}$I-Tyr14-Orphanin FQ with the Orphanin FQ Receptor: Kinetics and Modulation by Cations and Guanine Nucleotides", Molecular Pharmacology, vol. 51, pp. 816-824 (1997).

German Search Report dated Aug. 29, 2007 w/partial English translation (nine (9) pages).

International Search Report dated Jul. 15, 2008 w/partial English translation (three (3) pages).

SPIROCYCLIC CYCLOHEXANE COMPOUNDS

CROSS REFERENCE TO RELATED APPLICATIONS

This application is a continuation of international patent application no. PCT/EP2008/001270, filed Feb. 19, 2008 designating the United States of America and published in German on Aug. 28, 2008 as WO 2008/101659, the entire disclosure of which is incorporated herein by reference. Priority is claimed based on Federal Republic of Germany patent application no. DE 10 2007 009 235.2, filed Feb. 22, 2007.

BACKGROUND OF THE INVENTION

The present invention relates to spirocyclic cyclohexane compounds, to processes for the preparation thereof, to pharmaceutical compositions comprising these compounds and to the use of spirocyclic cyclohexane compounds in the preparation of pharmaceutical compositions.

The heptadecapeptide nociceptin is an endogenous ligand of the ORL1 (opioid-receptor-like) receptor (Meunier et al., Nature 377, 1995, p. 532-535) which belongs to the family of the opioid receptors and is to be found in many regions of the brain and of the spinal cord and exhibits a high affinity for the ORL1 receptor. The ORL1 receptor is homologous with the µ, κ and δ opioid receptors, and the amino acid sequence of the nociceptin peptide exhibits a strong similarity with those of the known opioid peptides. The activation of the receptor induced by nociceptin leads, via coupling with $G_{i/o}$ proteins, to inhibition of adenylate cyclase (Meunier et al., Nature 377, 1995, p. 532-535).

After intercerebroventicular administration, the nociceptin peptide exhibits pronociceptive and hyperalgesic activity in various animal models (Reinscheid et al., Science 270, 1995, p. 792-794). These findings can be explained as inhibition of stress-induced analgesia (Mogil et al., Neuroscience 75, 1996, p. 333-337). In this connection, nociceptin has also been shown to have anxiolytic activity (Jenck et al., Proc. Natl. Acad. Sci. USA 94, 1997, 14854-14858).

On the other hand, nociceptin has also been shown to have an antinociceptive effect in various animal models, especially after intrathecal administration. Nociceptin has an antinociceptive action in various models of pain, for example in the tail-flick test in the mouse (King et al., Neurosci. Lett., 223, 1997, 113-116). In models for neuropathic pain, it has likewise been possible to demonstrate an antinociceptive action for nociceptin, which is of particular interest in that the effectiveness of nociceptin increases after axotomy of spinal nerves. This is in contrast to conventional opioids, whose effectiveness diminishes under these conditions (Abdulla and Smith, J. Neurosci., 18, 1998, p. 9685-9694).

The ORL1 receptor is additionally also involved in the regulation of further physiological and pathophysiological processes. These include inter alia learning and memory formation (Manabe et al., Nature, 394, 1997, p. 577-581), hearing ability (Nishi et al., EMBO J., 16, 1997, p. 1858-1864) and numerous further processes. In an overview article by Calo et al. (Br. J. Pharmacol., 129, 2000, 1261-1283), an overview is given of the indications or biological processes in which the ORL1 receptor plays or with high probability might play a role. Those mentioned are, inter alia: analgesia, stimulation and regulation of food intake, influence on µ-agonists such as morphine, treatment of withdrawal symptoms, reduction of the addictive potential of opioids, anxiolysis, modulation of motor activity, memory disorders, epilepsy; modulation of neurotransmitter secretion, especially of glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhoea), relaxing effects on the respiratory tract, micturition reflex (urinary incontinence). The use of agonists and antagonists as anoretics, analgesics (also in co-administration with opioids) or nootropics is furthermore discussed.

The possible applications of compounds that bind to the ORL1 receptor and activate or inhibit it are correspondingly many and varied. In addition, opioid receptors such as the µ-receptor and the other subtypes of these opioid receptors, namely δ and κ, play a large part in the therapy of pain as well as in other of the mentioned indications. It is accordingly advantageous if the compounds also exhibit activity in respect of these opioid receptors.

WO 2004043967 discloses spirocyclic cyclohexane compounds which have a high affinity for the ORL1 receptor but also for the µ-opioid receptor. WO 2004043967 also describes, generically, a group in which $R^3$ denotes alkyl or cycloalkyl. However, no exemplary compounds that are part of this sub-group are disclosed.

Solubility is an important property for bioavailability and a significant factor in respect of the effectiveness and therefore also the success of a pharmaceutical composition. Complex processes are used to increase the solubility, for example the preparation of micro- or nano-particles (e.g. Exp. Op. Dug Disc. 2007, 2, 145); however, it is simpler and more predictable to develop compounds which have a higher solubility while being equally as effective.

A disadvantage of the example compounds disclosed in WO 2004043967 is the poor solubility of the compounds.

SUMMARY OF THE INVENTION

It was an object of the present invention to provide pharmaceutical compositions which act on the nociceptin/ORL1 receptor system and have a higher solubility than the compounds disclosed in WO 2004043967.

Surprisingly, it has now been found that some compounds which are described generically in WO 2004043967 but have not been disclosed by means of example compounds have a higher solubility than the example compounds disclosed therein. The invention therefore provides spirocyclic cyclohexane compounds corresponding to formula I

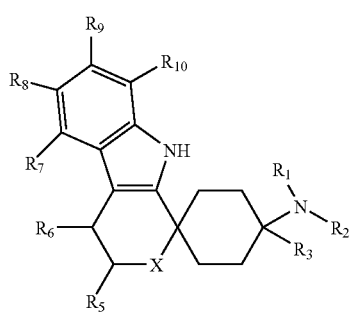

wherein
$R^1$ and $R^2$ each independently represent H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl, unsubstituted or mono- or poly-substituted; or $C_{1-3}$-alkyl-bonded aryl, $C_{3-8}$-cycloalkyl or heteroaryl, in each case mono- or poly-substituted or unsubstituted; or $R^1$ and $R^2$ together represent $CH_2CH_2OCH_2CH_2$, $CH_2CH_2NR^{11}CH_2CH_2$ or $(CH_2)_{3-6}$, wherein $R^{11}$ denotes H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; or $C_{1-3}$-alkyl-bonded aryl, $C_{3-8}$-cycloalkyl or heteroaryl, in each case mono- or poly-substituted or unsubstituted;

$R^3$ represents $C_{1-8}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted;

$R^5$ represents =O; H; $C_{1-5}$-alkyl, saturated or unsaturated, branched or unbranched, unsubstituted or mono- or poly-substituted; $COOR^{13}$, $CONR^{13}$, $OR^{13}$; $C_{3-8}$-cycloalkyl, saturated or unsaturated, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted;

$R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted; or $R^5$ and $R^6$ together denote $(CH_2)_n$ where n=2, 3, 4, 5 or 6, wherein individual hydrogen atoms can also be replaced by F, Cl, Br, I, $NO_2$, $CF_3$, $OR^{13}$, CN or $C_{1-5}$-alkyl;

$R^7$, $R^8$, $R^9$ and $R^{10}$ each independently represent H, F, Cl, Br, I, $NO_2$, $CF_3$, $OR^{13}$, $SR^{13}$, $SO_2R^{13}$, $SO_2OR^{13}$, NHC(=O)$NR^{14}R^{15}$, $SO_2NR^{14}R^{15}$, CN, $COOR^{13}$, $NR^{14}R^{15}$; $C_{1-5}$-alkyl, $C_{3-8}$-cycloalkyl, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted; wherein $R^{13}$ denotes H; $C_{1-5}$-alkyl in each case saturated or unsaturated, branched or unbranched, unsubstituted or mono- or poly-substituted; $C_{3-8}$-cycloalkyl, in each case saturated or unsaturated, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted;

$R^{14}$ and $R^{15}$ independently of one another denote H; $C_{1-5}$-alkyl, in each case saturated or unsaturated, branched or unbranched, unsubstituted or mono- or poly-substituted; or $C_{3-8}$-cycloalkyl, in each case saturated or unsaturated, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted; or $R^{14}$ and $R^{15}$ together form $CH_2CH_2OCH_2CH_2$, $CH_2CH_2NR^{16}CH_2CH_2$ or $(CH_2)_{3-6}$, wherein $R^{16}$ denotes H; $C_{1-5}$-alkyl, saturated or unsaturated, branched or unbranched, unsubstituted or mono- or poly-substituted;

X represents O, S, SO, $SO_2$ or $NR^{17}$;

$R^{17}$ represents H; $C_{1-5}$-alkyl, saturated or unsaturated, branched or unbranched; $COR^{12}$ or $SO_2R^{12}$, wherein $R^{12}$ denotes H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; or $C_{1-3}$-alkyl-bonded aryl, $C_{3-8}$-cycloalkyl or heteroaryl, in each case mono- or poly-substituted or unsubstituted; $OR^{13}$; $NR^{14}R^{15}$;

in the form of the racemate; of the enantiomers, diastereoisomers, mixtures of the enantiomers or diastereoisomers or of an individual enantiomer or diastereoisomer; of the bases and/or salts of physiologically acceptable acids or cations.

When combining different radicals, for example $R^7$, $R^8$, $R^9$ and $R^{10}$, and when combining radicals on their substituents, for example $OR^{13}$, $SR^{13}$, $SO2R^{13}$ or $COOR^{13}$, a substituent, for example $R^{13}$, for two or more radicals, for example $R^7$, $R^8$, $R^9$ and $R^{10}$, within a substance can have different meanings.

The compounds according to the invention exhibit good binding to the ORL1 receptor, but also to other opioid receptors.

Within the scope of this invention the terms "$C_{1-8}$-alkyl", "$C_{1-5}$-alkyl" and "$C_{1-3}$-alkyl" include acyclic saturated or unsaturated hydrocarbon radicals, which can be branched- or straight-chained as well as unsubstituted or mono- or poly-substituted, having 1, 2, 3, 4, 5, 6, 7 or 8 carbon atoms or having 1, 2, 3, 4 or 5 carbon atoms or 1, 2 or 3 carbon atoms, that is to say $C_{1-8}$-alkanyls, $C_{2-8}$-alkenyls and $C_{2-8}$-alkynyls or $C_{1-5}$-alkanyls, $C_{2-5}$-alkenyls and $C_{2-5}$-alkynyls or $C_{1-3}$-alkanyls, $C_{2-3}$-alkenyls and $C_{2-3}$-alkynyls. Alkenyls contain at least one C—C double bond and alkynyls contain at least one C—C triple bond. Alkyl is advantageously selected from the group comprising methyl, ethyl, n-propyl, 2-propyl, n-butyl, isobutyl, sec-butyl, tert-butyl, n-pentyl, isopentyl, neopentyl, n-hexyl, 2-hexyl; ethylenyl (vinyl), ethynyl, propenyl (—$CH_2CH=CH_2$, —CH=CH—$CH_3$, —C(=$CH_2$)—$CH_3$), propynyl (—CH—C≡CH, —C≡C—$CH_3$), 1,1-dimethylethyl, 1,1-dimethylpropyl, butenyl, butynyl, pentenyl, pentynyl, hexyl, hexenyl, hexynyl, heptyl, heptenyl, heptynyl, octyl, octenyl and octynyl. Particular preference is given within the scope of this invention to methyl, ethyl, n-propyl and n-butyl.

For the purposes of this invention, the expression "cycloalkyl" or "$C_{3-8}$-cycloalkyl" denotes cyclic hydrocarbons having 3, 4, 5, 6, 7 or 8 carbon atoms, it being possible for the hydrocarbons to be saturated or unsaturated (but not aromatic), unsubstituted or mono- or poly-substituted. $C_{3-8}$-Cycloalkyl is advantageously selected from the group containing cyclopropyl, cyclobutyl, cyclopentyl, cyclohexyl, cycloheptyl, cyclooctyl, cyclopentenyl, cyclohexenyl, cycloheptenyl and cyclooctenyl. Particular preference is given within the scope of this invention to cyclobutyl, cyclopentyl and cyclohexyl.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—.

Within the scope of this invention, the term "aryl" denotes carbocyclic ring systems having at least one aromatic ring but without heteroatoms in only one of the rings, inter alia phenyls, naphthyls and phenanthrenyls, fluoranethenyls, fluorenyls, indanyls and tetralinyls. The aryl radicals can also be fused to further saturated, (partially) unsaturated or aromatic ring systems. Each aryl radical can be unsubstituted or mono- or poly-substituted, it being possible for the aryl substituents to be identical or different and to be in any desired and possible position of the aryl. Phenyl or naphthyl radicals are particularly advantageous.

The term "heteroaryl" represents a 5-, 6- or 7-membered cyclic aromatic group which contains at least 1 heteroatom, optionally also 2, 3, 4 or 5 heteroatoms, it being possible for the heteroatoms to be identical or different and for the heterocycle to be unsubstituted or mono- or poly-substituted; in the case of substitution on the heterocycle, the substituents can be identical or different and can be in any desired and possible position of the heteroaryl. The heterocycle can also be part of a bi- or poly-cyclic system. Preferred heteroatoms are nitrogen, oxygen and sulfur. It is preferable for the heteroaryl radical to be selected from the group containing pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl and oxadiazolyl, it being possible for bonding to the compounds of the general structure I to take place via any desired and possible ring member of the heteroaryl group.

In connection with definitions of substituents, "alkyl" denotes "$C_{1-5}$-alkyl" unless "alkyl" is specifically defined further.

Within the scope of this invention, the term "substituted" in connection with "alkyl" and "cycloalkyl" is understood as meaning the substitution of one or more hydrogen radicals by F, Cl, Br, I, —CN, $NH_2$, NH-alkyl, NH-aryl, NH-heteroaryl, NH-cycloalkyl, NH-alkyl-aryl, NH-alkyl-heteroaryl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, $SO_2$-alkyl, $SO_2NH_2$, $SO_3H$, PO(O—$C_{1-6}$-alkyl)$_2$=O, =S, polysubstituted radicals being understood as being radicals that are substituted several times, for example two or three times, either on different atoms or on the same atom, for example three times on the same C atom, as in the case of $CF_3$ or —$CH_2CF_3$, or at different places, as in the case of —CH(OH)—CH=CH—CHCl$_2$. Polysubstitution can be carried out with the same substituent or with different substituents. A substituent can optionally also itself be substituted; accordingly, Oalkyl also includes inter alia —O—$CH_2$—$CH_2$—O—$CH_2$—$CH_2$—OH. It is preferred within the scope of this invention for alkyl or cycloalkyl to be substituted by F, Cl, Br, I, CN, $CH_3$, $C_2H_5$, $NH_2$, $NO_2$, SH, $CF_3$, OH, $OCH_3$, cyclopentyl, cyclohexyl, $OC_2H_5$ or $N(CH_3)_2$, preferably by F, Cl, Br, I, CN, $CH_3$, $C_2H_5$, $NH_2$, $NO_2$, SH, $CF_3$, OH, $OCH_3$, $OC_2H_5$ or $N(CH_3)_2$. It is most particularly preferred for alkyl or cycloalkyl to be substituted by OH, $OCH_3$ or $OC_2H_5$.

In relation to "aryl" or "heteroaryl", "mono- or poly-substituted" is understood within the scope of this invention as meaning the substitution of one or more hydrogen atoms of the ring system one or more times, for example two, three, four or five times, by F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)—$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NHaryl, C(=O)NH-cycloalkyl, C(=O)N(alkyl)$_2$, C(=O)N(alkyl-aryl)$_2$, C(=O) N(alkyl-heteroaryl)$_2$, C(=O)N(cycloalkyl)$_2$, S(O)-alkyl, S(O)-aryl, $SO_2$-alkyl, $SO_2$-aryl, $SO_2NH_2$, $SO_3H$, $CF_3$; alkyl, cycloalkyl, aryl and/or heteroaryl; on one atom or optionally on different atoms (it being possible for a substituent itself to be substituted). Polysubstitution is carried out with the same substituent or with different substituents. It is particularly preferred within the scope of this invention for aryl or heteroaryl to be substituted by F, Cl, Br, I, CN, $CH_3$, $C_2H_5$'$NH_2$, $NO_2$, SH, $CF_3$, OH, $OCH_3$, $OC_2H_5$ or $N(CH_3)_2$.

The term salt is understood as meaning any form of the active ingredient according to the invention in which the active ingredient assumes an ionic form or is charged and is coupled with a counter-ion (a cation or anion) or is in solution. The term is also understood as meaning complexes of the active ingredient with other molecules and ions, especially complexes complexed via ionic interactions. In particular, the term is understood as meaning (and this is also a preferred embodiment of this invention) physiologically acceptable salts, especially physiologically acceptable salts with cations or bases and physiologically acceptable salts with anions or acids or also a salt formed with a physiologically acceptable acid or a physiologically acceptable cation.

The term of the physiologically acceptable salt with anions or acids is understood within the scope of this invention as meaning salts of at least one of the compounds according to the invention—in most cases protonated, for example at the nitrogen—as the cation with at least one anion, which are physiologically acceptable—especially when used in humans and/or mammals. In particular, the term is understood within the scope of this invention as meaning the salt formed with a physiologically acceptable acid, namely salts of the particular active ingredient with inorganic or organic acids which are physiologically acceptable—especially when used in humans and/or mammals. Examples of physiologically acceptable salts of particular acids include salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, acetylsalicylic acid, hippuric acid and/or aspartic acid. The hydrochloride salt, the citrate and the hemicitrate are particularly preferred.

The term of the salt formed with a physiologically acceptable acid is understood within the scope of this invention as meaning salts of the particular active ingredient with inorganic or organic acids which are physiologically acceptable—especially when used in humans and/or mammals. The hydrochloride and the citrate are particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid.

The term of the physiologically acceptable salt with cations or bases is understood within the scope of this invention as meaning salts of at least one of the compounds according to the invention—in most cases of a (deprotonated) acid—as the anion with at least one cation, preferably an inorganic cation, which are physiologically acceptable—especially when used in humans and/or mammals. Particular preference is given to the salts of the alkali metals and alkaline earth metals and also ammonium salts, but especially (mono-) or (di-)sodium, (mono-) or (di-)potassium, magnesium or calcium salts.

The term of the salt formed with a physiologically acceptable cation is understood within the scope of this invention as meaning salts of at least one of the particular compounds as the anion with at least one inorganic cation which is physiologically acceptable—especially when used in humans and/or mammals. Particular preference is given to the salts of the alkali metals and alkaline earth metals and also ammonium salts, but especially (mono-) or (di-)sodium, (mono-) or (di-)potassium, magnesium or calcium salts.

Compounds corresponding to formula I are preferred in which:

$R^1$ and $R^2$ each independently represent H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or unsubstituted or mono- or poly-substituted; or $C_{1-3}$-alkyl-bonded aryl, $C_{3-8}$-cycloalkyl or heteroaryl, in each case mono- or poly-substituted or unsubstituted; or $R^1$ and $R^2$ together represent $CH_2CH_2OCH_2CH_2$, $CH_2CH_2NR^{11}CH_2CH_2$ or $(CH_2)_{3-6}$, wherein
  $R^{11}$ denotes H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; or $C_{1-3}$-alkyl-bonded aryl, $C_{3-8}$-cycloalkyl or heteroaryl, in each case mono- or poly-substituted or unsubstituted;

$R^3$ represents $C_{1-8}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted;

$R^5$ represents =O; H; $C_{1-5}$-alkyl, saturated or unsaturated, branched or unbranched, unsubstituted or mono- or poly-substituted; $COOR^{13}$, $CONR^{13}$, $OR^{13}$; $C_{3-8}$-cycloalkyl, saturated or unsaturated, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted;

$R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted; or $R^5$ and $R^6$ together denote $(CH_2)_n$ where n=2, 3, 4, 5 or 6, wherein individual hydrogen atoms can also be replaced by F, Cl, Br, I, $NO_2$, $CF_3$, $OR^{13}$, CN or $C_{1-5}$-alkyl;

$R^7$, $R^8$, $R^9$ and $R^{10}$ each independently represent H, F, Cl, Br, I, $NO_2$, $CF_3$, $OR^{13}$, $SR^{13}$, $SO_2R^{13}$, $SO_2OR^{13}$, NHC(=O)$NR^{14}R^{15}$, $SO_2NR^{14}R^{15}$, CN, $COOR^{13}$, $NR^{14}R^{15}$; $C_{1-5}$-alkyl, $C_{3-8}$-cycloalkyl, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted; wherein
  $R^{13}$ denotes H; $C_{1-5}$-alkyl, in each case saturated or unsaturated, branched or unbranched, unsubstituted or mono- or poly-substituted; $C_{3-8}$-cycloalkyl, in each case saturated or unsaturated, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted;

$R^{14}$ and $R^{15}$ each independently denote H; $C_{1-5}$-alkyl, in each case saturated or unsaturated, branched or unbranched, unsubstituted or mono- or poly-substituted; or $C_{3-8}$-cycloalkyl, in each case saturated or unsaturated, unsubstituted or mono- or poly-substituted; aryl or heteroaryl, unsubstituted or mono- or poly-substituted; or $C_{1-3}$-alkyl-bonded aryl, $C_{3-8}$-cycloalkyl or heteroaryl, unsubstituted or mono- or poly-substituted; or $R^{14}$ and $R^{15}$ together form $CH_2CH_2OCH_2CH_2$, $CH_2CH_2NR^{16}CH_2CH_2$ or $(CH_2)_{3-6}$, wherein
  $R^{16}$ denotes H; $C_{1-5}$-alkyl saturated or unsaturated, branched or unbranched, unsubstituted or mono- or poly-substituted;

X represents O, S, SO, $SO_2$ or $NR^{17}$;
$R^{17}$ represents H; $C_{1-5}$-alkyl, saturated or unsaturated, branched or unbranched; $COR^{12}$ or $SO_2R^{12}$, wherein
  $R^{12}$ denotes H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; or $C_{1-3}$-alkyl-bonded aryl, $C_{3-8}$-cycloalkyl or heteroaryl, in each case mono- or poly-substituted or unsubstituted; $OR^{13}$; $NR^{14}R^{15}$;

wherein "alkyl substituted" or "cycloalkyl substituted" denotes alkyl or cycloalkyl substituted by F, Cl, Br, I, CN, $CH_3$, $C_2H_5$, $NH_2$, $NO_2$, SH, $CF_3$, OH, $OCH_3$, cyclopentyl, cyclohexyl, $OC_2H_5$ or $N(CH_3)_2$ and "aryl substituted" or "heteroaryl substituted" denotes aryl or heteroaryl substituted by F, Cl, Br, I, CN, $CH_3$, $C_2H_5$, $NH_2$, $NO_2$, SH, $CF_3$, OH, $OCH_3$, $OC_2H_5$ or $N(CH_3)_2$, in the form of the racemate; of the enantiomers, diastereoisomers, mixtures of the enantiomers or diastereoisomers or of an individual enantiomer or diastereoisomer; of the bases and/or salts of physiologically acceptable acids or cations.

In one preferred embodiment of the spirocyclic cyclohexane compounds according to the invention, $R^1$ and $R^2$ each independently represent H, $C_{1-5}$-alkyl, branched or unbranched, saturated or unsaturated, unsubstituted or mono- or poly-substituted, or phenyl or benzyl, unsubstituted or mono- or poly-substituted, or $R^1$ and $R^2$ together represent a ring and denote $(CH_2)_{3-6}$. in particular, $R^1$ and $R^2$ each independently represent H, methyl, ethyl, n-propyl, or together represent —$CH_2CH_2CH_2$— or —$CH_2CH_2CH_2CH_2$—, wherein preferably only one of $R^1$ and $R^2$ denotes H. Particularly preferably, $R^1$ and $R^2$ each independently represent H, $CH_3$ or $C_2H_5$, wherein $R^1$ and $R^2$ do not both represent H, or $R^1$ and $R^2$ form a ring and represent —$CH_2CH_2CH_2$— or —$CH_2CH_2CH_2CH_2$—. Most particularly preferably, $R^1$ and $R^2$ represent H or $CH_3$, wherein $R^1$ and $R^2$ do not simultaneously denote $CH_3$; in particular $R^1$ and $R^2$ represent $CH_3$.

Spirocyclic cyclohexane compounds corresponding to formula I also are preferred in which $R^3$ represents ethyl, n-propyl, 2-propyl, allyl, n-butyl, isobutyl, sec-butyl, tert-butyl, n-pentyl, isopentyl, neopentyl, n-hexyl, methylcyclopentyl, methylcyclohexyl, cyclopentyl or cyclohexyl, in each case unsubstituted or mono- or poly-substituted by OH, $OCH_3$ or $OC_2H_5$. In particular, compounds are preferred in which $R^3$ represents ethyl, n-propyl, 2-propyl, allyl, n-butyl, isobutyl, sec-butyl, tert-butyl, n-pentyl, isopentyl, neopentyl, n-hexyl, cyclopentyl or cyclohexyl, in each case unsubstituted or mono- or poly-substituted by OH, $OCH_3$ or $OC_2H_5$. Substituted cyclohexane compounds corresponding to formula I are particularly preferred in which $R^3$ denotes ethyl, n-propyl or n-butyl, unsubstituted or mono- or poly-substituted by $OCH_3$, OH or $OC_2H_5$, in particular by $OCH_3$.

In one preferred embodiment of the spirocyclic cyclohexane compounds according to the invention, $R^5$ represents H, $CH_3$, COOH, $COOCH_3$, $CH_2O$ phenyl, wherein the phenyl radical can be substituted by F, Cl, Br, I, CN, $CH_3$, $C_2H_5$, $NH_2$, $NO_2$, SH, $CF_3$, OH, $OCH_3$, $OC_2H_5$ or $N(CH_3)_2$, or $CH_2OH$. Substituted cyclohexane compounds in which $R^5$ represents H are particularly preferred.

Substituted cyclohexane compounds corresponding to formula I are also preferred in which $R^6$ can denote H; methyl, ethyl, $CF_3$, benzyl or phenyl, wherein the benzyl or phenyl radical can be substituted by F, Cl, Br, I, CN, $CH_3$, $C_2H_5$, $NH_2$, $NO_2$, SH, $CF_3$, OH, $OCH_3$, $OC_2H_5$ or $N(CH_3)_2$. Spirocyclic cyclohexane compounds are particularly preferred in which $R^6$ denotes H.

Preference is further given to spirocyclic cyclohexane compounds in which $R^7$, $R^8$, $R^9$ and $R^{10}$ each independently denote H; $C_{1-5}$-alkyl, branched or unbranched, unsubstituted or mono- or poly-substituted; F, Cl, Br, I, $CF_3$, OH, $OCH_3$, $NH_2$, COOH, $COOCH_3$, $NHCH_3$, thienyl, pyrimidinyl, pyridyl, $N(CH_3)_2$ or $NO_2$. Preferably one of $R^7$, $R^8$, $R^9$ and $R^{10}$ represents H; $C_{1-5}$-alkyl, branched or unbranched, unsubstituted or mono- or poly-substituted; F, Cl, Br, I, OH, $OCH_3$, COOH, $COOCH_3$, $NH_2$, $NHCH_3$ or $N(CH_3)_2$ or $NO_2$, while the remaining radicals are H, or two of $R^7$, $R^8$, $R^9$ and $R^{10}$ each independently represent H; $C_{1-5}$-alkyl, branched or unbranched, unsubstituted or mono- or poly-substituted; F, Cl, Br, I, OH, $OCH_3$, COOH, $COOCH_3$, $NH_2$, $NHCH_3$ or $N(CH_3)_2$ or $NO_2$, while the remaining radicals are H. Particular preference is given to spirocyclic cyclohexane compounds wherein $R^7$, $R^8$, $R^9$ and $R^{10}$ represent H, F, OH, Cl or $OCH_3$.

Compounds in which X represents O are most particularly preferred. Furthermore, compounds corresponding to formula I in which X represents $NR^{17}$ are most particularly preferred.

Preferred spirocyclic cyclohexane compounds also include those in which $R^{17}$ denotes $COR^{12}$, and $R^{12}$ denotes H; $C_{1-5}$-alkyl; $C_{3-8}$-cycloalkyl; or $C_{1-3}$-alkyl-bonded aryl, $C_{3-8}$-cycloalkyl or heteroaryl, in each case mono- or poly-substituted or unsubstituted; $NR^{14}R^{15}$. In particular, compound are preferred in which $R^{12}$ denotes H; benzyl, phenethyl, phenethenyl; in each case unsubstituted or substituted by $OCH_3$; $CH_3$, 2,2-dimethylpropyl or cyclopentyl.

Most particularly preferred are compounds selected from the group consisting of:

4',9'-dihydro-N,N-dimethyl-4-ethyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-ethyl-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-ethyl-spiro[cyclohexane-1,1'(1'H)-pyrido[3,4-b]indol]-4-amine, 2-hydroxy-1,2,3-propanetricarboxylate 4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-hydroxy-4',9'-dihydro-N,N-dimethyl-4-butyl-spiro[cyclohexane-1,1'(3'H)-pyrano[3,4-b]indol]-4-amine, 2,2,2-trifluoroacetate 6'-hydroxy-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-butyl-spiro[cyclohexane-1,1'(1'H)-pyrido[3,4-b]indol]-4-amine, 2-hydroxy-1,2,3-propanetricarboxylate 2',3',4',9'-tetrahydro-N,N-dimethyl-4-butyl-2'-methylcarbonyl-spiro[cyclohexane-1,1'-(1'H)-pyrido[3,4-b]indol]-4-amine, 2-hydroxy-1,2,3-propanetricarboxylate 2',3',4',9'-tetrahydro-N,N-dimethyl-4-butyl-2'-cyclopentylcarbonyl-spiro[cyclohexane-1,1'(1'H)-pyrido[3,4-b]indol]-4-amine, 2-hydroxy-1,2,3-propanetricarboxylate 2',3',4',9'-tetrahydro-N,N-dimethyl-4-butyl-2'-(2,2)-dimethylpropanecarbonyl-spiro[cyclohexane-1,1'(1'H)-pyrido[3,4-b]indol]-4-amine, 2-hydroxy-1,2,3-propanetricarboxylate 2',3',4',9'-tetrahydro-N,N-dimethyl-4-butyl-2'-(3,4-dimethoxybenzylcarbonyl)-spiro[cyclohexane-1,1'(1'H)-pyrido[3,4-b]indol]-4-amine, 2-hydroxy-1,2,3-propanetricarboxylate 2',3',4',9'-tetrahydro-N,N-dimethyl-4-butyl-2'-ethylaminocarbonyl-spiro[cyclohexane-1,1'(1'H)-pyrido[3,4-b]indol]-4-amine, 2-hydroxy-1,2,3-propanetricarboxylate 2',3',4',9'-tetrahydro-N,N-dimethyl-4-butyl-2'-4-methoxybenzylaminocarbonyl-spiro[cyclohexane-1,1'(1'H)-pyrido[3,4-b]indol]-4-amine 2',3',4',9'-tetrahydro-N,N-dimethyl-4-buty-2'-methyl-spiro[cyclohexane-1,1'(1'H)-pyrido[3,4-b]indol]-4-amine, 2-hydroxy-1,2,3-propanetricarboxylate 6'-fluoro-4',9'-dihydro-N-ethyl-N-methyl-4-butyl-spiro[cyclohexane-1,1'(3'H)-pyrano[3,4-b]indol]-4-amine, 2-hydroxy-1,2,3-propanetricarboxylate 6'-fluoro-4',9'-dihydro-N-benzyl-N-methyl-4-butyl-spiro[cyclohexane-1,1'(3'H)-pyrano[3,4-b]indol]-4-amine 6'-fluoro-4',9'-dihydro-N-phenyl-4-butyl-spiro[cyclohexane-1,1'(3'H)-pyrano[3,4-b]indol]-4-amine 4-butyl-6'-fluoro-4-(N-morpholino)-1',3',4',9'-tetrahydrospiro[cyclohexane-1,1'-pyrano[3,4-b]indole]

4-butyl-6'-fluoro-4-(N-morpholino)-1',3',4',9'-tetrahydrospiro[cyclohexane-1,1'-pyrano[3,4-b]indole]

4',9'-dihydro-N,N-dimethyl-4-methoxypropyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-methoxypropyl-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-(3-methoxypropyl)-spiro[cyclohexane-1,1'(1'H)-pyrido[3,4-b]indol]-4-amine, 2-hydroxy-1,2,3-propanetricarboxylate 4',9'-dihydro-N,N-dimethyl-4-(4-methoxybutyl)-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-(4-methoxybutyl)-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-(4-methoxybutyl)-spiro[cyclohexane-1,1'(1'H)-pyrido[3,4-b]indol]-4-amine, 2-hydroxy-1,2,3-propanetricarboxylate 4',9'-dihydro-N,N-dimethyl-4-cyclopentyl-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-cyclopentyl-spiro[cyclohexane-1,1'(1'H)-pyrido[3,4-b]indol]-4-amine, 2-hydroxy-1,2,3-propanetricarboxylate 4',9'-dihydro-N,N-dimethyl-4-cyclohexyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-cyclohexyl-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-cyclohexyl-spiro[cyclohexane-1,1'(1'H)-pyrido[3,4-b]indol]-4-amine, 2-hydroxy-1,2,3-propanetricarboxylate 2',3',4',9'-tetrahydro-N,N-dimethyl-4-butyl-spiro[cyclohexane-1,1'(1'H)-pyrido[3,4-b]indol]-4-amine, 2-hydroxy-1,2,3-propanetricarboxylate 6'-fluoro-4',9'-dihydro-N,N-dimethyl-4-ethyl-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-(3-methoxypropyl)-spiro[cyclohexane-1,1'(1'H)-pyrido[3,4-b]indol]-4-amine, 2-hydroxy-1,2,3-propanetricarboxylate 6'-fluoro-4',9'-dihydro-N,N-dimethyl-4-methoxypropyl-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-butyl-2'-ethylaminocarbonyl-spiro[cyclohexane-1,1'(1'H)-pyrido[3,4-b]indol]-4-amine 4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 2',3',4',9'-tetrahydro-N,N-dimethyl-4-(4-methoxybutyl)-spiro[cyclohexane-1,1'(1'H)-pyrido[3,4-b]indol]-4-amine, 2-hydroxy-1,2,3-propanetricarboxylate 6'-fluoro-4',9'-dihydro-N-benzyl-4-allyl-spiro[cyclohexane-1,1'(3'H)-pyrano[3,4-b]indol]-4-amine, 2-hydroxy-1,2,3-propanetricarboxylate 6'-fluoro-4',9'-dihydro-N-phenyl-4-allyl-spiro[cyclohexane-1,1'(3'H)-pyrano[3,4-b]indol]-4-amine 6'-fluoro-4',9'-dihydro-N-(4-methoxybenzyl)-4-allyl-spiro[cyclohexane-1,1'(3'H)-pyrano[3,4-b]indol]-4-amine N-{6'-fluoro-4',9'-dihydro-4-butyl-spiro[cyclohexane-1,1'(3'H)-pyrano[3,4-b]indol]-4-yl}-pyrrolidine, 2-hydroxy-1,2,3-propanetricarboxylate N-{6'-fluoro-4',9'-dihydro-4-butyl-spiro[cyclohexane-1,1'(3'H)-pyrano[3,4-b]indol]-4-yl}-piperidine N-{6'-fluoro-4',9'-dihydro-4-butyl-spiro[cyclohexane-1,1'(3'H)-pyrano[3,4-b]indol]-4-yl}-piperidine, 2-hydroxy-1,2,3-propanetricarboxylate N-{6'-fluoro-4',9'-dihydro-4-butyl-spiro[cyclohexane-1,1'(3'H)-pyrano[3,4-b]indol]-4-yl}-n-methylpiperazine, 2-hydroxy-1,2,3-propanetricarboxylate 4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-hydroxy-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-cyclopentylmethyl-spiro[cyclohexane 1,1'(3'H)-pyrano[3,4-b]indol]-4-amine, 2-hydroxy-1,2,3-propanetricarboxylate 2',3',4',9'-tetrahydro-N,N-dimethyl-4-butyl-2'-(2-phenylethenecarbonyl)-spiro[cyclohexane-1,1'(1'H)-pyrido[3,4-b]indol]-4-amine, 2-hydroxy-1,2,3-propanetricarboxylate optionally also in the form of a mixture.

The compounds of the invention act, for example, on the ORL1 receptor, which is relevant in connection with various disorders, so that they are suitable as a pharmaceutical active ingredient in a pharmaceutical composition. Accordingly, the invention further provides pharmaceutical compositions comprising at least one spirocyclic cyclohexane compound according to the invention as well as, optionally, suitable additives and/or auxiliary substances and/or optionally further active ingredients.

In addition to at least one spirocyclic cyclohexane compound according to the invention, the pharmaceutical compositions according to the invention optionally comprise suitable additives and/or auxiliary substances, that is to say also carrier materials, fillers, solvents, diluents, colorings and/or binders, and can be administered as liquid pharmaceutical composition forms in the form of injection solutions, drops or juices, as semi-solid pharmaceutical composition forms in the form of granules, tablets, pellets, patches, capsules, plasters/spray-on plasters or aerosols. The choice of the auxiliary substances etc. and the amounts thereof to be employed depend on whether the pharmaceutical composition is to be administered orally, perorally, parenterally, intravenously, intraperitoneally, intradermally, intramuscularly, intranasally, buccally, rectally or locally, for example to the skin, the mucous membranes or in the eyes. Preparations in the form of tablets, coated tablets, capsules, granules, drops, juices and syrups are suitable for oral administration; solutions, suspensions, easily reconstitutable dry formulations and sprays are suitable for parenteral and topical administration and for inhalatory administration. Spirocyclic cyclohexane compounds according to the invention in a depot, in dissolved form or in a plaster, optionally with the addition of agents which promote penetration through the skin, are suitable preparations for percutaneous administration. Forms of preparation which can be used orally or percutaneously can release the spirocyclic cyclohexane compounds according to the invention in a delayed manner. The spirocyclic cyclohexane compounds according to the invention can also be used in parenteral long-term depot forms, for example implants or implanted pumps. Other further active ingredients known to the person skilled in the art can in principle be added to the pharmaceutical compositions according to the invention.

The amount of active ingredient to be administered to the patients varies according to the weight of the patient, the mode of administration, the indication and the severity of the disorder. From 0.00005 to 50 mg/kg, preferably from 0.001 to 0.5 mg/kg, of at least one spirocyclic cyclohexane compound according to the invention are usually administered.

In a preferred form of the pharmaceutical composition, a spirocyclic cyclohexane compound according to the invention contained therein is present in the form of a pure diastereoisomer and/or enantiomer, in the form of a racemate or in the form of a non-equimolar or equimolar mixture of the diastereoisomers and/or enantiomers.

As noted above, the ORL1 receptor has been identified especially in the occurrence of pain. Spirocyclic cyclohexane compounds according to the invention can accordingly be used in the preparation of a pharmaceutical composition for the treatment of pain, especially of acute, neuropathic or chronic pain.

Accordingly, the invention relates further to the use of a spirocyclic cyclohexane compound according to the invention in the preparation of a pharmaceutical composition for the treatment of pain, especially of acute, visceral, neuropathic or chronic pain.

The invention relates further to the use of a spirocyclic cyclohexane compound according to the invention in the preparation of a pharmaceutical composition for the treatment of anxiety, stress and stress-associated syndromes, depression, epilepsy, Alzheimer's disease, senile dementia, general cognitive dysfunctions, learning and memory disorders (as a nootropic), withdrawal symptoms, alcohol and/or drug and/or pharmaceutical composition abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhoea, cachexia, urinary incontinence or as a muscle relaxant, anticonvulsive or anaesthetic or for co-administration in the case of treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for the treatment of withdrawal symptoms and/or for reducing the addictive potential of opioids.

In one of the above uses it may be preferable for a spirocyclic cyclohexane compound used to be in the form of a pure diastereoisomer and/or enantiomer, in the form of a racemate or in the form of a non-equimolar or equimolar mixture of the diastereoisomers and/or enantiomers.

The invention further provides a method of treating, especially in one of the above-mentioned indications, a non-human mammal or human requiring the treatment of pain, especially chronic pain, by administration of a therapeutically effective dose of a spirocyclic cyclohexane compound according to the invention, or of a pharmaceutical composition according to the invention.

The invention further provides a process for the preparation of the spirocyclic cyclohexane compounds according to the invention, as indicated in the following description and examples. Particularly suitable is a process for the preparation of a spirocyclic cyclohexane compound according to the invention wherein a cyclohexanone compound corresponding to formula E is reacted with an indole compound corresponding to formula F or H.

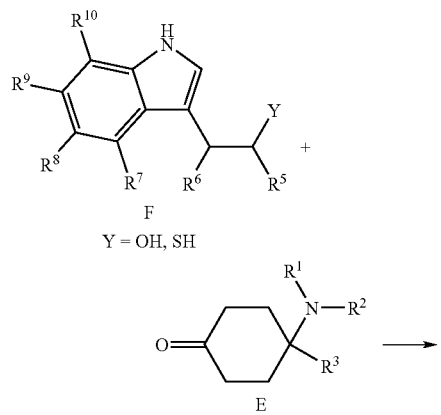

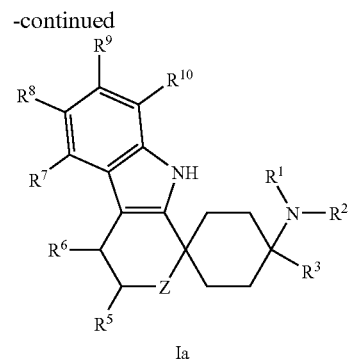

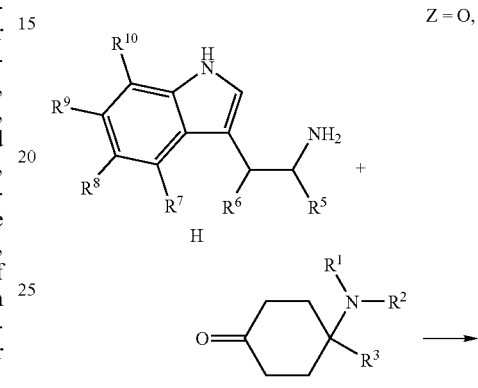

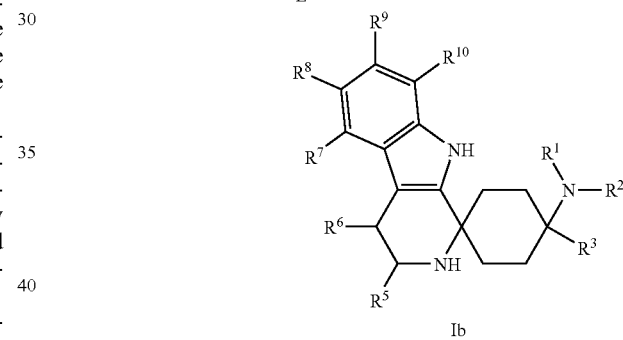

Tryptophols of type F (Y=O) can be reacted in reactions of the Oxa-Pictet-Spengler type, and tryptamines of type H can be reacted in reactions of the Pictet-Spengler type, with ketones, with the addition of at least one suitable reagent from the group acids, acid anhydrides, esters or weakly reacting salts or Lewis acids, to form products of formula I. For X=SH, the reaction takes place analogously. There is preferably used at least one reagent from the group carboxylic acids, phosphoric acids or sulfonic acids or their respective anhydrides, carboxylic acid trialkylsilyl esters, acid-reacting salts, mineral acids or Lewis acids selected from the group consisting of boron trifluoride, indium(III) chloride, titanium tetrachloride, aluminium(III) chloride, or with the addition of at least one transition metal salt, preferably with the addition of at lest one transition metal triflate (transition metal trifluoromethanesulfonate), particularly preferably with the addition of at least one transition metal trifluoromethanesulfonate selected from the group consisting of scandium(III) trifluoromethanesulfonate, ytterbium(III) trifluoromethanesulfonate and indium(III) trifluoromethanesulfonate, optionally with the addition of Celite, with solid-phase-bound reactants or reagents, at elevated or reduced temperature, with or without microwave radiation, optionally in a suitable solvent or solvent mixture, for example chlorinated or unchlorinated, preferably aromatic, hydrocarbons, acetonitrile; in ethereal solvents, preferably in diethyl ether or THF; or in nitromethane, in suitable cases also in alcohols or water.

Particular preference is given to the use of pyridinium paratoluenesulfonate, phosphorus pentoxide in the presence of Celite, boron trifluoride etherate, trifluoroacetic acid, orthotitanic acid tetraisopropyl ester together with trifluoroacetic acid, trifluoromethanesulfonic acid trimethylsilyl ester, trifluoromethanesulfonic acid, methanesulfonic acid, trifluoroacetic acid, acetic acid, phosphoric acid, polyphosphoric acid, polyphosphate ester, p-toluenesulfonic acid, hydrochloric acid HCl gas, sulfuric acid together with acetate buffer, tin tetrachloride.

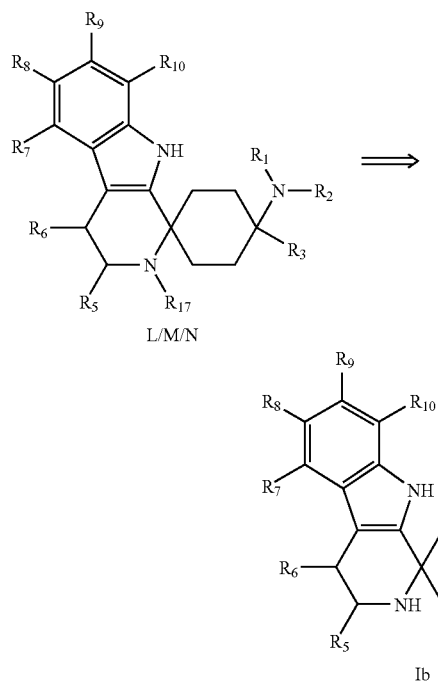

L/M/N

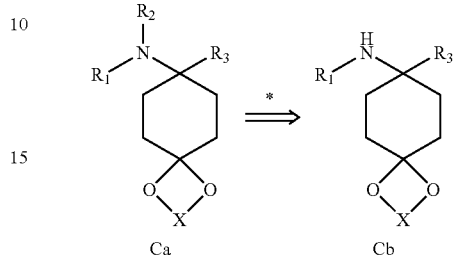

Ib

Secondary amines of type I can be acylated, sulfonylated or carbamoylated according to processes known to the person skilled in the art to give compounds of type L/M/N. These reactions are preferably carried out at elevated temperature, particularly preferably with microwave radiation. Such a method known to the person skilled in the art is the reaction with an anhydride or acid chloride with the addition of a base, for example triethylamine.

Synthesis of the Ketone Structural Units

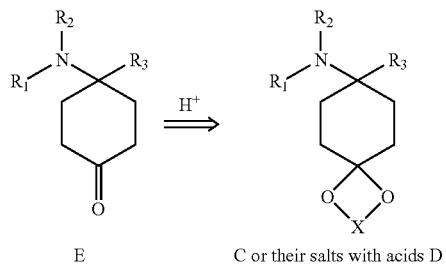

E          C or their salts with acids D

Compounds of formula E can be freed from corresponding acetals C, or from salts D thereof, according to methods known to the person skilled in the art by deprotecting by means of acids. X is selected from the group alkyl, alkyl/alkylidene/alkylidene substituted by aryl or alkyl (saturated/unsaturated).

Aminoacetals Cb having not more than one substituent on the nitrogen atom can be converted according to processes known to the person skilled in the art, for example by reductive amination, into corresponding amino-acetals Ca having one or two further substituents on the nitrogen.

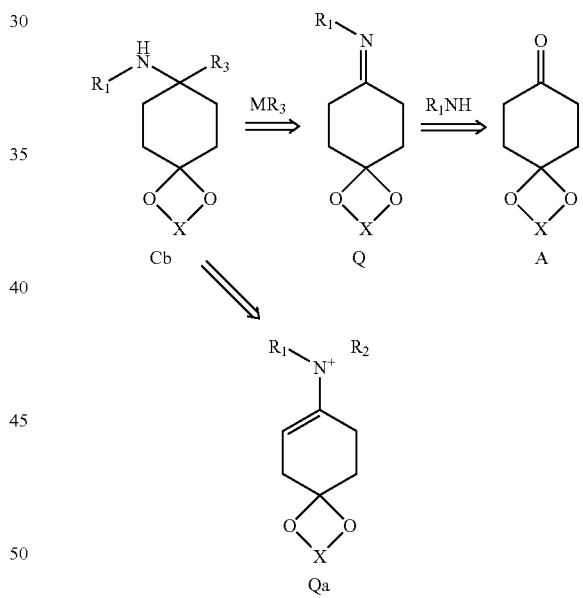

Aminoacetals Cb having not more than one substituent on the nitrogen atom can be obtained according to processes known to the person skilled in the art by addition of carbon nucleophiles to imines Q, preferably organometal compounds in inert solvents, particularly preferably with Grignard reagents or organolithium compounds, preferably in ethers, preferably at temperatures of from −100 to room temperature.

Aminoacetals C having two substituents on the nitrogen atom can also be obtained according to processes known to the person skilled in the art by addition of carbon nucleophiles to salts of enamines Qa, preferably with organometal compounds in inert solvents.

The preparation of imines is known from the literature.

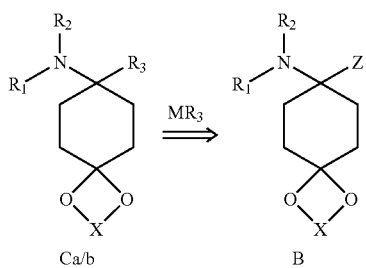

Acetals C can also be obtained by substitution of suitable leaving groups Z in structures of formula B. Suitable leaving groups are preferably cyano groups; 1,2,3-triazol-1-yl groups. Further suitable leaving groups are 1H-benzo[d][1,2,3]triazol-1-yl groups and pyrazol-1-yl groups (Katritzky et al., Synthesis 1989, 66-69).

A particularly preferred route to compounds of structure C is the reaction of aminonitriles B with corresponding organometal compounds, preferably Grignard compounds, preferably in ethers, preferably at room temperature. The organometal compounds are either available commercially or can be prepared by known processes.

A further particularly preferred route to compounds of structure C is the reaction of aminotriazoles B with corresponding organometal compounds, preferably Grignard compounds, preferably in ethers, preferably at room temperature.

The organometal compounds are either available commercially or can be prepared by methods known in the literature.

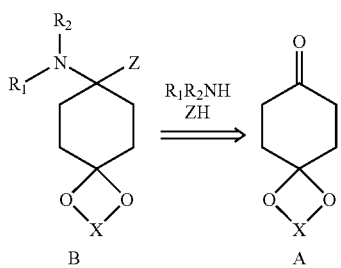

Structures of formula B can be prepared by reaction of ketones A with amines and acidic reactants Z—H. Suitable reactants Z—H are, for example, hydrogen cyanide, 1,2,3-triazole, benzotriazole or pyrazole.

A particularly preferred route to compounds of structure B is the reaction of ketones with metal cyanides and the corresponding amine in the presence of acid, preferably in an alcohol, at temperatures of from −40 to 60° C., preferably at room temperature, with alkali metal cyanides in methanol.

A further particularly preferred route to compounds of structure B is the reaction of ketones with 1,2,3-triazole and the corresponding amine under water-removing conditions, preferably using a water separator at elevated temperature in an inert solvent or using molecular sieve or another drying agent. Structures analogous to B having benzotriazole or pyrazole groups instead of triazole groups can be introduced analogously.

Compounds corresponding to formulas F and H are either available commercially or their preparation is known from the prior art or can be derived from the prior art in a manner that is obvious to the person skilled in the art. The following citations are particularly relevant in this connection: Jirkovsky et al., J. Heterocycl. Chem., 12, 1975, 937-940; Beck et al., J. Chem. Soc. Perkin 1, 1992, 813-822; Shinada et al., Tetrahedron Lett., 39, 1996, 7099-7102; Garden et al., Tetrahedron, 58, 2002, 8399-8412; Lednicer et al., J. Med. Chem., 23, 1980, 424-430; Bandini et al. J. Org. Chem. 67, 15; 2002, 5386-5389; Davis et al., J. Med. Chem. 35, 1, 1992, 177-184; Yamagishi et al., J. Med. Chem. 35, 11, 1992, 2085-2094; Gleave et al.; Bioorg. Med. Chem. Lett. 8, 10, 1998, 1231-1236; Sandmeyer, Helv. Chim. Acta; 2; 1919; 239; Katz et al.; J. Med. Chem. 31, 6, 1988; 1244-1250; Bac et al. *Tetrahedron Lett.* 1988, 29, 2819; Ma et al. *J. Org. Chem.* 2001, 66, 4525; Kato et al., J. Fluorine Chem. 99, 1, 1999, 5-8.

Solubility Tests

The solubility tests were carried out using five compounds according to the invention and five exemplary compounds. The data were acquired with reference to a series of compounds which, apart from the radical on $R^3$, exhibited large similarities so that comparability is ensured. It was found that compounds that carry an alkyl radical on $R^3$ are markedly better soluble than compounds that carry a phenyl or thienyl radical on $R^3$. Surprisingly, even this structural variation brings about an increase in the solubility. The introduction of an OH group at $R^8$, a typical derivatisation (metabolisation) which is carried out by the living organism to increase solubility in order to excrete a compound via the kidneys, did not produce a comparable increase in solubility (compounds V-4 and V-5).

EXAMPLES

The following examples serve to illustrate the invention in further detail but do not limit the general inventive concept. The yields of the prepared compounds are not optimized. All temperatures are uncorrected.

The term "ether" means diethyl ether, "EA" means ethyl acetate, "DCM" means dichloromethane. The term "equivalents" means substance amount equivalents, "m.p." means melting point or melting range, "decomp." means decomposition, "RT" means room temperature, "abs." means absolute (anhydrous), "rac." means racemic, "conc." means concentrated, "min." means minutes, "h" means hours, "d" means days, "vol %" means percent by volume, "wt. %" means percent by weight and "M" is the concentration stated in mol/l.

Silica gel 60 (0.040-0.063 mm) from E. Merck, Darmstadt, was employed as the stationary phase for column chromatography. The thin-layer chromatography analyses were carried out with HPTLC pre-coated plates, silica gel 60 F 254, from E. Merck, Darmstadt. The mixing ratios of mobile phases for chromatographic analyses are always stated in volume/volume.

Ketones

Structural Unit B-1

8-Dimethylamino-1,4-dioxa-spiro[4.5]decane-8-carbonitrile (B-1)

40% aqueous dimethylamine solution (116 ml, 0.92 mol), cyclohexane-1,4-dione monoethyleneketal (30.0 g, 0.192 mol) and potassium cyanide (30.0 g, 0.46 mol) were added, while cooling with ice, to a mixture of 4N hydrochloric acid (50 ml) and methanol (30 ml). The mixture was stirred for 72 h at room temperature; water (80 ml) was added, and then the mixture was extracted with ether (4×100 ml). The residue obtained after concentrating the solution was taken up in dichloromethane (200 ml) and dried overnight with magnesium sulfate. The organic phase was concentrated, and the ketal B-1 was obtained in the form of a white solid.

Yield: 38.9 g (96%)
Melting point: 86-88° C.
$^1$H-NMR (DMSO-d$_6$): 1.57 (2H, m); 1.72 (2H; m); 1.85 (2H, m); 1.99 (2H, m); 2.25 (6H, s); 3.87 (4H, m).
$^{13}$C-NMR (DMSO-d$_6$): 30.02; 31.32; 60.66; 63.77; 106.31; 118.40.

Structural Unit B-2

8-(Ethylmethylamino)-1,4-dioxaspiro[4.5]decane-8-carbonitrile (B-2)

To a mixture of 4 N hydrochloric acid (15 ml, 60 mmol) and methanol (10 ml) there were added, while cooling with ice, first ethylmethylamine (16.0 g, 23 ml, 262 mmol) and water (10 ml) and then 1,4-dioxaspiro[4.5]deca-8-one (9.40 g, 60 mmol) and potassium cyanide (9.20 g, 141 mmol). The reaction mixture was stirred for 5 d at room temperature. Water (100 ml) was then added, and the solution was extracted with diethyl ether (5×50 ml). The combined organic phases were dried with sodium sulfate and concentrated in vacuo.

Yield: 10.8 g (80%), yellow oil
$^1$H-NMR (DMSO-d$_6$): 1.04 (t, 3H, J=7.1 Hz); 1.50-1.59 (m, 2H); 1.68-1.77 (m, 2H); 1.89-1.95 (m, 2H); 1.98-2.06 (m, 2H); 2.23 (s, 3H); 2.42-2.48 (m, 2H, superimposed with the DMSO signal); 3.87 (s, 4H).

Structural Unit E-1

This structural unit was obtained instead of the desired target product. It is clear that D-1 can also be prepared purposively from ethylmagnesium bromide and B-1.

(8-Ethyl-1,4-dioxa-spiro[4.5]dec-8-yl)-dimethylamine (D-1)

A mixture of ethyl bromide (30.0 g, 0.3 mol) and 3-bromopyridine (16.0 g, 0.1 mol) was added dropwise to magnesium powder (10.0 g) in diethyl ether (50 ml). When the Grignard formation was complete, aminonitrile B-1 (10.5 g, 47.6 mmol) in THF (80 ml) was added to the grey solution at 0° C. in the course of 15 min., and the reaction solution was stirred overnight at room temperature. 20% ammonium chloride solution (50 ml) and water (50 ml) were then added to the reaction solution, while cooling with ice. The reaction solution was diluted with diethyl ether (100 ml), the organic phase was separated and the aqueous phase was extracted 2× with Et$_2$O (100 ml). The combined organic phases were washed with water (50 ml) and NaCl solution (50 ml), dried over Na$_2$SO$_4$ and filtered, and the solvent was removed in vacuo. The residue was taken up in 2-butanone (200 ml), and Me$_3$SiCl (10 ml) was added at 0° C. The reaction solution was stirred for 5 h, with the exclusion of moisture, and the resulting solid was filtered out with suction.

Yield: 6.8 g (64%), light-brown solid
$^1$H-NMR (DMSO-d$_6$): 0.94 (3H, t); 1.51-1.60 (2H, m); 1.77-1.86 (8H, m); 2.64 (6H, 2 s); 3.83-3.89 (4H, m).

4-Dimethylamino-4-ethyl-cyclohexanone (E-1)

The hydrochloride D-1 (6.67 g, 0.026 mmol) was dissolved in 6N HCl (40 ml) and stirred overnight at room temperature. The reaction mixture was extracted twice with diethyl ether (100 ml). The mixture was then rendered alkaline with 5N NaOH, while cooling with ice, and extracted again three times with Et$_2$O (100 ml). The combined organic phases were dried over Na$_2$SO$_4$ and filtered, and the solvent was removed in vacuo.

Yield: 4.16 g (92%), brown oil
$^1$H-NMR (DMSO-d$_6$): 0.81 (3H, t); 1.43-1.50 (2H, q); 1.67-1.89 (2H, m); 1.83-1.89 (2H, m); 1.99-2.06 (2H, m); 2.22 (6H, 2 s); 2.39-2.43 (4H, m).
$^{13}$C-NMR (DMSO-d$_6$): 8.71; 21.99; 30.41; 36.17; 37.07; 38.66; 55.53; 210.57.

Structural Unit E-2

Variant 1

(8-Butyl-1,4-dioxa-spiro[4.5]dec-8-yl)-dimethylamine hydrochloride (D-2)

8-Dimethylamino-1,4-dioxa-spiro[4.5]decane-8-carbonitrile B-1 (10.5 g, 50 mmol) was placed in THF (150 ml), under argon and while cooling with ice. In the course of 15 min., 2M butyl-magnesium chloride in THF (62.5 ml, 125 mmol) was added dropwise, and the mixture was stirred for 16 h at room temperature. 20% ammonium chloride solution (37 ml) and water (50 ml) were added to the mixture, while cooling with ice, and extraction with ether (3×50 ml) was carried out. The organic phase was washed with water (1×50 ml) and saturated sodium chloride solution (1×50 ml), and the organic phase was dried with Na$_2$SO$_4$ and concentrated in vacuo. The crude product (2.05 g) was dissolved in ethyl methyl ketone (75 ml); ClSiMe$_3$ (9.5 ml, 75 mmol) was added, while cooling with ice, and stirring was carried out for 6 h at room temperature. The resulting white precipitate was filtered out with suction and dried in vacuo.

Yield: 3.1 g (22%)
$^1$H-NMR (DMSO-d$_6$): 0.91 (3H, t); 1.31 (4H, m); 1.56 (2H, m); 1.75 (8H, m); 2.64 (6H, s); 3.87 (4H, s); 9.87 (1H, s).

Variant 1

4-Butyl-4-dimethylamino-cyclohexanone (E-2)

8-Butyl-1,4-dioxa-spiro[4.5]dec-8-yl)-dimethyl-amine hydrochloride D-2 (3.10 g, 11.1 mmol) was placed in H$_2$O (4.7 ml) and conc. HCl (7 ml) and stirred for 24 h at room temperature. The mixture was extracted with ether (1×15 ml), and the aqueous phase was rendered alkaline with 5N NaOH, while cooling with ice, and extracted with dichloromethane (3×20 ml). The organic phase was dried over Na$_2$SO$_4$ and concentrated in vacuo.

Yield: 1.96 g (89%), oil
$^1$H-NMR (DMSO-d$_6$): 0.88 (3H, t); 1.23 (4H, m); 1.40 (2H, m); 1.68 (2H, m); 1.91 (2H, m); 2.31 (2H, m); 2.22 (6H, s); 2.42 (2H, m).
$^{13}$C-NMR (DMSO-d$_6$): 13.91; 23.21; 26.06; 29.53; 31.07; 37.04; 38.88; 55.36; 210.37.

Variant 2

(8-Butyl-1,4-dioxa-spiro[4.5]dec-8-yl)-dimethylamine hydrochloride (D-2)

2M n-butylmagnesium chloride solution in THF (228 ml, 0.456 mol) was slowly added under argon, while cooling with an ice/sodium chloride mixture, to a solution of aminonitrile B-1 (38.3 g, 0.182 mol) in abs. tetrahydrofuran (420 ml). The reaction temperature was not to exceed 10° C. during the addition. The mixture was then stirred for 16 h at room temperature. A clear brown solution formed. For working up of the reaction mixture, saturated ammonium chloride solution (150 ml) was added dropwise, while cooling with ice (0 to 10° C.). A white solid formed and was dissolved by addition of water (about 250 ml). The reaction mixture was extracted with diethyl ether (4×100 ml). The organic phase was washed with water (100 ml) and saturated NaCl solution (100 ml), dried and concentrated. There remained a yellow oil (44.5 g) which, as well as containing the desired butyl compound, also contained the nitrile starting material. The crude product was dissolved in ethyl methyl ketone (275 ml); ClSiMe$_3$ (32 ml, 0.245 mol) was added, while cooling with ice, and stirring was carried out at room temperature in an open flask. The hydrochloride D-2 was separated by filtering several times at 2-hour intervals. After a reaction time of 6-8 h, the hydrochloride D-2 could be isolated in the form of a white solid in a yield of 82% (41.8 g).

Variant 2

4-Butyl-4-dimethylamino-cyclohexanone (E-2)

The hydrochloride D-2 (41.8 g, 0.15 mmol) was dissolved in water (78 ml), and 37% hydrochloric acid (100 ml, 1.2 mol) was added, with stirring and while cooling with ice. The clear reaction mixture was stirred for 7 days at room temperature. When the hydrolysis was complete, the reaction mixture was extracted with diethyl ether (2×70 ml). The organic extracts were discarded. The aqueous phase was rendered alkaline with 5N sodium hydroxide solution (about 250 ml), while cooling with ice, and stirred vigorously. The solution was extracted with diethyl ether (3×100 ml). The combined organic extracts were washed with water (2×70 ml), dried and concentrated. The ketone E-2 was obtained in the form of a light-brown oil in a yield of 96% (28.4 g). The yield of ketone E-2—based on the ketal used in the first stage—was 75%.

Structural Unit E-3

1-Chloro-4-methoxy-butane

Sodium hydride (24.0 g, 1.0 mol) and iodomethane (142 g, 1.0 mol) were placed in abs. THF (350 ml). Under argon and while cooling with ice, a solution of 4-chlorobutan-1-ol (54 g, 0.5 mol) in abs. THF (50 ml) was added dropwise in the course of 1.5 h, whereupon slight gas formation occurred. The mixture was stirred for 24 h at room temperature. 20% NH$_4$Cl solution (130 ml) was added dropwise to the reaction solution. The organic phase was separated and dried over Na$_2$SO$_4$, and the drying agent was filtered out. The organic phase was distilled under normal pressure.

Boiling point: 150-162° C.
Yield: 10.4 g (17%)
$^1$H-NMR (DMSO-d$_6$): 1.93 (2H, m); 3.23 (3H; s); 3.44 (2H, t); 3.66 (2H, t).

[8-(4-Methoxy-butyl)-1,4-dioxa-spiro[4.5]dec-8-yl]-dimethyl-amine (C-3)

A solution of 1-chloro-4-methoxy-butane (8.19 g, 66.8 mmol) in abs. ether (12 ml) was added, under an argon atmosphere and with intermittent heating, to magnesium (1.62 g, 66.8 mmol) and I$_2$ in abs. diethyl ether (25 ml). The mixture was stirred for 1 h under reflux until the magnesium had largely dissolved. While cooling with ice, a solution of 8-dimethylamino-1,4-dioxa-spiro[4.5]decane-8-carbonitrile B-1 (10.5 g, 50.1 mmol) in abs. THF (40 ml) was added dropwise. A viscous precipitate formed, and further abs. THF (20 ml) was added for the purpose of better mixing. The mixture was stirred for 24 h at room temperature. NH$_4$Cl solution (20%, 80 ml) and water (100 ml) were added to the mixture, while cooling with ice, the organic phase was separated and the aqueous phase was extracted with ether (3×100 ml). The combined organic phases were washed with saturated NaCl solution (80 ml) and water (80 ml), dried over Na$_2$SO$_4$ and concentrated in vacuo. The crude product was purified by flash chromatography with chloroform/methanol (50:1 ⇨ 20:1 ⇨ 9:1).

Yield: 6.44 g (59%), yellow oil
$^{13}$C-NMR (DMSO-d$_6$): 19.81; 27.10; 29.26; 30.34; 35.79; 37.48; 57.76: 63.72; 64.07; 71.35; 106.46.

4-Dimethylamino-4-(4-methoxy-butyl)-cyclohexanone (E-3)

[8-(4-Methoxy-butyl)-1,4-dioxa-spiro[4.5]dec-8-yl]-dimethyl-amine (C-3) (6.44 g, 23.7 mmol) was dissolved in water (9.3 ml); conc. HCl (14.6 ml) was added, and the mixture was stirred for 4 d at room temperature. The reaction mixture was washed with ether (2×50 ml). Then the solution was rendered alkaline with 5N NaOH and extracted with dichloromethane (3×50 ml). The combined organic phases were washed with water (50 ml), dried over Na$_2$SO$_4$ and filtered, and the solvent was removed in vacuo.

Yield: 4.91 g (91%), yellow oil
$^{13}$C-NMR (DMSO-d$_6$): 20.56; 29.75; 29.83; 30.98; 36.92; 37.06; 55.40: 57.73; 71.76; 210.39.

Structural Unit E-4

1-Chloro-3-methoxy-propane

3-Methoxypropan-1-ol (47.1 g, 50 ml, 0.523 mol) was dissolved in pyridine (41.3 g, 42.6 ml, 0.523 mol); the solution was cooled to 10° C. and thionyl chloride (93.3 g, 56.9 ml, 0.784 mol) was added dropwise at 10-30° C., with vigorous stirring. A solid precipitate formed, and the mixture was then stirred for a further 3 h at 65° C. The mixture was poured onto a mixture of ice (130 g) and conc. HCl (26 ml). The aqueous solution was extracted with ether (2×20 ml), and the combined organic phases were washed with K$_2$CO$_3$ solution. On addition of the drying agent K$_2$CO$_3$, vigorous gas formation was observed and the solution was therefore allowed to stand overnight. The drying agent was removed, and the organic phase was washed with K$_2$CO$_3$ solution until the reaction was alkaline. The organic phase was separated, washed with water and dried over K$_2$CO$_3$, filtered and distilled at normal pressure. Boiling point: 113° C.

Yield: 41.2 g (72%), colorless liquid
$^1$H-NMR (DMSO-d$_6$): 1.93 (2H, m); 3.23 (3H; s); 3.44 (2H, t); 3.66 (2H, t).

[8-(3-Methoxy-propyl)-1,4-dioxa-spiro[4.5]dec-8-yl]-dimethyl-amine (C-4)

A solution of 1-chloro-3-methoxy-propane (10.0 g, 92 mmol) in abs. ether (15 ml) was added dropwise, under an argon atmosphere and with intermittent heating, to magnesium (10.0 g, 92 mmol) and I$_2$ in abs. diethyl ether (30 ml). Then the mixture was stirred under reflux for 60 min., following which the magnesium had not dissolved completely.

While cooling with ice, a solution of 8-dimethylamino-1,4-dioxa-spiro[4.5]decane-8-carbonitrile B-1 (9.68 g, 46 mmol) in abs. THF (30 ml) was added dropwise. A viscous precipitate formed, and 100 ml of THF were then added for the purpose of better mixing. The mixture was stirred for 24 h at room temperature. 20% NH$_4$Cl solution (100 ml) and water (120 ml) were added to the mixture, while cooling with ice, the organic phase was separated and the aqueous phase was extracted with ether (3×120 ml). The combined organic phases were washed with saturated NaCl solution (120 ml) and water (120 ml), dried over Na$_2$SO$_4$ and concentrated in vacuo. The crude yield was 10.8 g of brown oil. 9.8 g of crude product were purified by flash chromatography with CHCl$_3$/MeOH (50:1 ⇨ 20:1 ⇨ 9:1).

Yield: 8.11 g (75%), yellow oil
$^1$H-NMR (DMSO-d$_6$): 1.44 (8H, m); 1.62 (4H; m); 2.25 (6H, s); 3.21 (3H, s); 3.31 (2H, m); 3.82 (4H, s).
$^{13}$C-NMR (DMSO-d$_6$): 23.99; 26.52; 28.87; 29.88; 36.97; 55.24: 57.67; 63.40; 72.62; 108.07.

4-Dimethylamino-4-(3-methoxy-propyl)-cyclohexanone (E-4)

The amine C-4 (8.11 g, 31.5 mmol) was dissolved in water (12 ml); while cooling with ice, conc. HCl (19.5 ml) was added and the whole was stirred for 3 days at room temperature. The reaction mixture was washed with ether (2×75 ml). Then the solution was rendered alkaline with 5N NaOH and extracted with dichloromethane (3×75 ml). The combined organic phases were washed with water (75 ml), dried over Na$_2$SO$_4$ and filtered, and the solvent was removed in vacuo.

Yield: 6.03 g (90%), yellow oil
$^1$H-NMR (DMSO-d$_6$): 1.44 (4H, m); 1.68 (2H; m); 1.88 (2H, m); 2.00 (1H, m); 2.05 (1H, m); 2.20 (6H, s); 2.41 (2H, m); 3.22 (3H, s); 3.28 (2H, m).
$^{13}$C-NMR (DMSO-d$_6$): 24.01; 26.34; 30.88; 36.15; 37.06; 55.26: 57.70; 72.55; 210.39.

Structural Unit E-5

(8-Cyclohexyl-1,4-dioxa-spiro[4.5]dec-8-yl)-dimethyl-amine (C-5)

2M cyclohexyl-magnesium chloride solution in ether (62.5 ml, 125 mmol) was added dropwise at 5-10° C., in the course of 15 min., under argon and while cooling with ice, to a solution of the aminonitrile B-1 (10.5 g, 50 mmol) in abs. THF (150 ml), and the whole was then stirred overnight at room temperature. For working up of the reaction mixture, 20% ammonium chloride solution (50 ml) and water (50 ml) were added, while cooling with ice, and extraction with ether (3×100 ml) was carried out. The organic phase was washed with water and saturated sodium chloride solution, dried over sodium sulfate and concentrated in vacuo. The residue that remained was purified by flash chromatography with CHCl$_3$/MeOH (20:1).

: 1.18 g (9%), colorless oil
$^1$H-NMR (DMSO-d$_6$): 1.05 (6H, m); 1.43 (5H; m); 1.61 (8H, m), 2.35 (6H, s); 3.86 (4H, s).

4-Cyclohexyl-4-dimethylamino-cyclohexanone (E-5)

6N hydrochloric acid (7 ml) was added to (8-cyclohexyl-1,4-dioxa-spiro[4.5]dec-8-yl)-dimethyl-amine (C-5) (1.18 g, 4.41 mmol), and the mixture was stirred overnight at room temperature. When the hydrolysis was complete, the reaction mixture was extracted with ether (2×10 ml), the aqueous solution was rendered alkaline with 5N sodium hydroxide solution, while cooling with ice, the reaction mixture was extracted with dichloromethane (3×20 ml), and the organic phase was dried over sodium sulfate and concentrated in vacuo. The crude product (637 mg) was purified by flash chromatography with CHCl$_3$/MeOH (9:1).

Yield: 366 mg (37%), colorless oil
$^1$H-NMR (DMSO-d$_6$): 1.08 (5H, m); 1.68 (8H; m); 1.99 (4H, m); 2.29 (2H, s), 2.41 (6H, s).

Structural Unit E-6

(8-Cyclopentyl-1,4-dioxa-spiro[4.5]dec-8-yl)-dimethyl-amine (C-6)

2M cyclopentyl-magnesium bromide solution in ether (62.5 ml, 125 mmol) was added dropwise at 5-10° C., in the course of 15 min., under argon and while cooling with ice, to a solution of the aminonitrile B-1 (10.5 g, 50 mmol) in abs. THF (150 ml), and the whole was then stirred for 72 h at room temperature. For working up of the reaction mixture, 20% ammonium chloride solution (50 ml) and water (50 ml) were added, while cooling with ice, and extraction with ether (3×100 ml) was carried out. The organic phase was washed with water and saturated sodium chloride solution, dried over sodium sulfate and concentrated in vacuo. The residue that remained was separated by flash chromatography with CHCl$_3$/MeOH (40: ⇨ 20:1). Because the desired product was still not clean, a further column chromatography with CHCl$_3$/MeOH (40:1) was carried out.

Yield: 692 mg (5%), colorless oil
$^1$H-NMR (DMSO-d$_6$): 1.23 (2H, m); 1.46 (9H; m); 1.69 (4H, m); 2.04 (1H, m); 2.23 (6H, s); 3.86 (4H, s).

4-Cyclopentyl-4-dimethylamino-cyclohexanone (E-6)

6N hydrochloric acid (5 ml) was added to the ketal C-6 (0.68 g, 2.68 mmol), and the mixture was stirred overnight at room temperature. When the hydrolysis was complete, the reaction mixture was extracted with ether (2×20 ml), the aqueous solution was rendered alkaline with 5N sodium hydroxide solution, while cooling with ice, extraction with dichloromethane (3×10 ml) was carried out, and the organic phase was dried over sodium sulfate and concentrated in vacuo.

: 424 mg (76%), colorless oil
$^1$H-NMR (DMSO-d$_6$): 1.28 (2H, m); 1.54 (8H; m); 1.99 (4H, m); 2.14 (1H, m); 2.29 (6H, s).
$^{13}$C-NMR (DMSO-d$_6$): 24.58; 28.13; 29.24; 36.07; 37.79; 42.97; 57.07; 210.67.

Structural Unit E-7

(8-Butyl-1,4-dioxaspiro[4.5]dec-8-yl)ethylmethylamine (C-7)

A solution of B-2 (3.50 g, 15.6 mmol) in tetrahydrofuran (50 ml) was added dropwise at 0° C., under argon, to a 2 M solution of butylmagnesium chloride in tetrahydrofuran (20 ml, 40 mmol), and the mixture was stirred overnight at room temperature. Saturated ammonium chloride solution (60 ml) was then added carefully to the reaction mixture, while cooling with ice, the pH value was corrected to 10 with sodium hydroxide solution, and extraction with diethyl ether (3×50 ml) was carried out. The combined organic phases were dried with sodium sulfate and concentrated in vacuo. The crude product was reacted further without being purified.

4-Butyl-4-(ethylmethylamino)cyclohexanone (E-7)

First water (2.5 ml) and then concentrated hydrochloric acid (2.5 ml) were added to a solution of C-7 (4.43 g, 17.3 mmol) in acetone (15 ml), and the mixture was stirred over the weekend at room temperature. Then the reaction mixture was rendered alkaline (pH 10) with 2 M potassium carbonate solution, extraction with diethyl ether (3×40 ml) was carried out, and the combined organic phases were dried with sodium sulfate and concentrated in vacuo. The crude product was purified by means of flash chromatography (200 g, 20×5.7 cm) with cyclohexane/ethyl acetate (2:1).

Yield: 2.08 g (57%), yellow oil $^1$H-NMR (DMSO-$d_6$): 0.87 (t, 3H, J=7.0 Hz); 1.00 (t, 3H, J=7.0 Hz); 1.20-1.29 (m, 4H); 1.38-1.42 (m, 2H); 1.63-1.71 (m, 2H); 1.92-2.00 (m, 4H); 2.20 (s, 3H); 2.36-2.47 (m, 4H).

Structural Unit E-8

Benzylmethyl-[8-(4H-[1,2,3]triazin-1-yl)-1,4-dioxaspiro[4.5]dec-8-yl]amine

A solution of 1,4-dioxaspiro[4.5]decan-8-one (3.9 g, 25 mmol), N-benzylmethylamine (3.32 g, 3.54 ml, 27.5 mmol) and 1,2,3-triazole (2.07 g, 30 mmol) in toluene (40 ml) was heated for 8 h under reflux in a water separator (Dean-Stark). After cooling to room temperature, the reaction solution was directly used further.

Benzyl-(8-butyl-1,4-dioxaspiro[4.5]dec-8-yl)methylamine (D-8)

The reaction solution of benzylmethyl-[8-(4H-[1,2,3]triazin-1-yl)-1,4-dioxaspiro-[4.5]dec-8-yl]amine (20 ml, about 25 mmol) was added dropwise at 0° C., under a stream of argon, to a 2 M solution of n-butylmagnesium chloride in tetrahydrofuran (50 ml, 100 mmol). The mixture was warmed to room temperature and stirred for 2 h and then poured into saturated ammonium chloride solution (60 ml). The phases were separated; the aqueous phase was extracted with diethyl ether (3×30 ml), and the combined organic phases were dried with sodium sulfate and concentrated in vacuo. The crude product was taken up in dichloromethane, the insoluble constituents were filtered out, the filtrate was concentrated in vacuo again, and the residue (6.31 g) was purified by flash chromatography (400 g, 20×7.6 cm) with cyclohexane/ethyl acetate (9:1).

Yield: 3.4 g (43% over two stages), colorless oil $^1$H-NMR (DMSO-$d_6$): 0.90 (t, 3H, J=6.8 Hz); 1.18-1.33 (m, 4H); 1.36-1.47 (m, 4H); 1.51-1.59 (m, 2H); 1.70-1.93 (m, 4H); 2.03 (3H, s); 3.57 (s, 2H); 3.85 (s, 4H); 7.15-7.25 (m, 1H); 7.27-7.36 (m, 4H).

4-(Benzylmethylamino)-4-butylcyclohexanone (E-8)

Water (10 ml) and 37% hydrochloric acid (14.1 ml) were added to a solution of D-8 (3.40 g, 10.7 mmol) in acetone (70 ml), and the mixture was stirred for 5.5 h at room temperature. Saturated potassium carbonate solution was then slowly added dropwise to the mixture until the pH reached 10. The mixture was extracted with diethyl ether (4×40 ml), and the combined organic phases were dried with sodium sulfate and concentrated in vacuo.

Yield: 2.3 g (74%), yellowish oil $^1$H-NMR (DMSO-$d_6$): 0.91 (t, 3H, J=6.74 Hz); 1.20-1.37 (m, 5H); 1.48-1.59 (m, 2H); 1.78 (dt, 2H, J=13.7 and 5.5 Hz); 2.00-2.17 (m, 4H); 2.09 (s, 3H); 2.50-2.60 (m, 1H); 3.66 (s, 2H); 7.12-7.26 (m, 1H); 7.26-7.38 (m, 4H).

Structural Unit E-9

1,4-Dioxaspiro[4.5]dec-8-ylidene)-(4-methoxybenzyl)amine

4 Å molecular sieve (20 g) and 4-methoxybenzylamine (11.8 g, 83 mmol) were added to a solution of 1,4-dioxaspiro[4.5]decan-8-one (10.0 g, 64 mmol) in dichloromethane (100 ml). The suspension was stirred for 16 h at room temperature and then filtered, and the filtrate was used in the next stage without being worked up further.

$^1$H-NMR (300 MHz, $CDCl_3$): 1.81 (t, J=6.3 Hz, 2H); 1.89 (t, J=6.3 Hz, 2H); 2.50 (t, J=6.3 Hz, 4H); 3.74 (s, 3H); 3.95 (s, 4H); 4.45 (s, 2H); 6.83 (d, J=8.6 Hz, 2H); 7.18 (d, J=8.6 Hz, 2H).

$^{13}$C-NMR (100 MHz, $CDCl_3$): 25.0; 34.0; 34.8; 36.2; 53.8; 55.1; 64.3; 108.3; 113.7; 128.0; 128.6; 158.2; 171.2.

(8-Allyl-1,4-dioxaspiro[4.5]dec-8-yl)-(4-methoxybenzyl)amine (C-9)

A 1 M solution of allylmagnesium bromide (100 ml, 100 mmol) in diethyl ether was added dropwise to a solution of 1,4-dioxaspiro[4.5]dec-8-ylidene)-(4-methoxy-benzyl) amine (17.6 g, 64 mmol) in dichloromethane (120 ml), and the reaction mixture was stirred for 4 h at room temperature. Then the mixture was poured onto saturated ammonium chloride solution (100 ml), while cooling with ice, and extraction with dichloromethane (3×40 ml) was carried out. The combined organic phases were dried with sodium sulfate and concentrated in vacuo. The residue was purified by flash chromatography (400 g, 20×7.6 cm) with chloroform/methanol (10:0.1).

Yield: 10.8 g (53%), brown oil $^1$H-NMR (300 MHz, $d_6$-DMSO): 1.30 (br s, 1H); 1.42 (t, J=11.5 Hz, 4H); 1.51-1.64 (m, 2H); 1.72-1.86 (m, 2H); 2.18 (d, J=7.3 Hz, 2H); 3.51 (s, 2H); 3.72 (s, 3H); 3.83 (s, 4H); 4.99-5.16 (m, 2H); 5.76-5.93 (m, 1H); 6.82-6.89 (m, 2H); 7.24 (m, 2H).

$^{13}$C-NMR (100 MHz, $d_6$-DMSO): 29.9; 32.1; 41.8; 44.3; 52.6; 54.9; 63.4; 108.3; 113.4; 117.2; 128.9; 133.6; 134.8; 157.9.

4-Allyl-4-(4-methoxybenzylamino)cyclohexanone (E-9)

Concentrated hydrochloric acid (0.5 ml) was added to a solution of (8-allyl-1,4-dioxaspiro[4.5]dec-8-yl)-(4-methoxybenzyl)amine (C-9) (1.0 g, 3.15 mmol) in acetone (10 ml) and water (0.5 liter), and the mixture was stirred for 16 h at room temperature. Then saturated sodium hydrogen carbonate solution (40 ml) was added to the solution, and extraction with dichloromethane (3×40 ml) was carried out. The combined organic phases were dried with sodium sulfate and concentrated in vacuo.

Yield: 864 mg (100%), brown oil $^1$H-NMR (400 MHz, $d_6$-DMSO): 1.64 (dt, J=13.2, 4.6 Hz, 2H); 1.89 (d, J=13.0 Hz, 2H); 2.04 (d, J=14.9 Hz, 2H); 2.30 (d, J=7.2 Hz, 2H); 2.45-2.63 (m, 2H); 3.61 (s, 2H); 3.72 (s, 3H); 5.12 (dd, J=13.1, 11.2 Hz, 2H); 5.90 (dt, J=17.1, 7.3 Hz, 1H); 6.86 (d, J=8.3 Hz, 2H); 7.28 (d, J=8.2 Hz, 2H). The NH signal could not be identified.

$^{13}$C-NMR (100 MHz, d$_6$-DMSO): −3.1; −0.9; 4.4; 7.4; 15.7; 17.9; 76.4; 80.5; 92.1; 96.4; 97.5; 120.9; 174.1.

Structural Unit E-10

Phenyl-(1,4-dioxaspiro[4.5]dec-8-ylidene)amine

The corresponding N-phenyl-substituted ketone E-10 was synthesised analogously to the synthesis of the ketone E-13. Analogously to the synthesis of benzyl-(1,4-dioxaspiro[4.5]dec-8-ylidene)amine (see structural unit E-13), 1,4-dioxaspiro[4.5]decan-8-one was reacted quantitatively with aniline, with the removal of water, to give the imine phenyl-(1,4-dioxaspiro[4.5]dec-8-ylidene)amine.

(8-Allyl-1,4-dioxaspiro[4.5]dec-8-yl)-phenyl-amine (C-10)

In the subsequent reaction of phenyl-(1,4-dioxaspiro[4.5]dec-8-ylidene)amine with allylmagnesium bromide (analogously to C-13), the desired (8-allyl-1,4-dioxaspiro[4.5]dec-8-yl)-phenyl-amine (C-10) could be isolated in a good yield.

4-Allyl-4-phenylaminocyclohexanone (E-10)

Concentrated hydrochloric acid (0.5 ml) was added to a solution of C-10 (333 mg, 1.22 mmol) in acetone (10 ml) and water (0.5 ml), and the mixture was stirred for 2 d at room temperature. Saturated sodium hydrogen carbonate solution (40 ml) was then added to the reaction mixture, and extraction with dichloromethane (3×40 ml) was carried out. The combined organic phases were dried with sodium sulfate and concentrated in vacuo.

Yield: 285 mg (100%), colorless crystals
Melting point: 76-78° C.
$^1$H-NMR (400 MHz, d$_6$-DMSO): 1.78 (dt, J=13.0, 4.6 Hz, 2H); 2.06-2.29 (m, 4H); 2.49 (m, 4H); 5.00 (dd, J=10.1, 1.9 Hz, 2H); 5.30 (s, 1H); 5.65-5.87 (m, 1H); 6.58 (t, J=7.2 Hz, 1H); 6.82 (dd, J=8.5 Hz, 2H); 7.07 (m, 2H).
$^{13}$C-NMR (100 MHz, d$_6$-DMSO): 34.5; 36.3; 41.0; 53.8; 115.3; 116.4; 117.5; 128.7; 134.3; 147.2; 210.4.

Structural Unit E-11

Variant 1

(1,4-Dioxaspiro[4.5]dec-8-ylidene)phenylimine

A solution of 1,4-dioxaspiro[4.5]deca-8-one (5.46 g, 35 mmol) and aniline (3.35 g, 3.28 ml, 36 mmol) in toluene (100 ml) was heated for 15 h in a water separator which was additionally charged with anhydrous sodium sulfate (2 g). In order to monitor the conversion, a sample was removed and concentrated in vacuo, and a $^1$H-NMR spectrum in DMSO was immediately measured. When the reaction was complete, the reaction solution was concentrated in vacuo and the residue was dissolved in anhydrous tetrahydrofuran.
$^1$H-NMR (DMSO-d$_6$): 1.70 (t, 2H, J=6.7 Hz); 1.86-1.94 (m, 2H); 2.21 (t, 2H, J=6.8 Hz); 2.35 (t, 2H, J=7.0 Hz); 3.91-3.94 (m, 4H); 6.67-6.71 (m, 2H); 6.96-7.04 (m, 1H); 7.24-7.31 (m, 2H).

Variant 2

(1,4-Dioxaspiro[4.5]dec-8-ylidene)phenylimine

4 Å molecular sieve (12.5 g) and aniline (3.80 g, 3.73 ml, 40.8 mmol) were added to a solution of 1,4-dioxaspiro[4.5]decan-8-one (6.20 g, 39.6 mmol) in dichloromethane (65 ml), and the mixture was stirred over the weekend at room temperature. In order to monitor the conversion, a sample was removed and concentrated in vacuo, and a $^1$H-NMR spectrum in CDCl$_3$ was immediately recorded. When the reaction was complete, the reaction mixture was filtered and the filtrate was concentrated in vacuo.
$^1$H-NMR (CDCl$_3$): 1.76 (t, 2H, J=6.6 Hz); 1.93-2.05 (m, 2H); 2.35 (t, 2H, J=6.7 Hz); 2.64 (t, 2H, J=6.6 Hz); 3.96-4.02 (m, 4H); 6.71 (d, 2H, J=7.8 Hz); 7.05 (t, 1H, J=7.2 Hz); 7.29 (t, 2H, J=7.9 Hz).

Variant 1

(8-Butyl-1,4-dioxaspiro[4.5]dec-8-yl)phenylamine (C-11) and 4-butyl-4-phenyl-aminocyclohexanone (E-11)

A solution of (1,4-dioxaspiro[4.5]dec-8-ylidene)phenylimine (17 mmol) in anhydrous tetrahydrofuran was added dropwise at 0° C., under argon, to a 1.6 M solution of n-butyllithium in n-hexane (27 ml, 42 mmol). Then the reaction mixture was slowly warmed to room temperature and stirred overnight. Water (40 ml) was then added to the reaction mixture, while cooling with ice, and extraction with diethyl ether (3×50 ml) was carried out. The combined organic phases were concentrated in vacuo and the residue was purified by means of flash chromatography (100 g, 20×4.0 cm) with cyclohexane/ethyl acetate (9:1) and 1% triethylamine.

C-11:
Yield: 645 mg (13%), brown oil
$^1$H-NMR (DMSO-d$_6$): 0.78 (t, 3H, J=6.8 Hz); 1.17-1.22 (m, 4H); 1.42-1.71 (m, 8H); 1.94-2.03 (m, 2H); 3.83 (s, 4H); 4.93 (s, 1H); 6.49 (t, 1H, J=7.3 Hz); 6.71 (d, 2H, J=8.0 Hz); 7.01 (t, 2H, J=7.8 Hz).
E-11:
Yield: 1.01 g (24%), brown oil
$^1$H-NMR (DMSO-d$_6$): 0.78 (t, 3H, J=7.0 Hz); 1.12-1.30 (m, 4H); 1.57-1.87 (m, 4H); 2.04-2.15 (m, 2H); 2.19-2.31 (m, 2H); 2.40-2.60 (m, 2H, superimposed with the DMSO signal); 5.25 (s, 1H); 6.55 (t, 1H, J=7.2 Hz); 6.77 (d, 2H, J=8.6 Hz); 7.00-7.09 (m, 2H).

In addition, a mixture of C-11 and E-11 (816 mg, about 20%) was also obtained.

Variant 2

(8-Butyl-1,4-dioxaspiro[4.5]dec-8-yl)phenylamine (C-11)

A solution of (1,4-dioxaspiro[4.5]dec-8-ylidene)phenylimine (39.6 mmol) in anhydrous tetrahydrofuran was added dropwise at 0° C., under argon, to a 1.6 M solution of n-butyllithium in n-hexane (63 ml, 98 mmol). Then the reaction mixture was warmed slowly to room temperature and stirred overnight. Water (40 ml) was then added to the reaction mixture, while cooling with ice, and extraction with diethyl ether (3×50 ml) was carried out. The combined organic phases were dried with sodium sulfate and concentrated in vacuo, and the residue was purified by means of flash chromatography (100 g, 20×4.0 cm) with cyclohexane/ethyl acetate (9:1) and 1% triethylamine.

Yield: 2.83 g (25%), brown oil

4-Butyl-4-phenylaminocyclohexanone (E-11)

Water (2.5 ml) and concentrated hydrochloric acid (2.5 ml) were added to a solution of C-11 (645 mg, 2.23 mmol) in acetone (15 ml), and the mixture was stirred over the weekend at room temperature. Then the reaction mixture was rendered alkaline (pH 10) with potassium carbonate solution, extraction with diethyl ether (3×30 ml) was carried out, and the combined organic phases were dried with sodium sulfate and concentrated in vacuo.

Yield: 547 mg (100%); brown oil $^{1}$H-NMR (DMSO-$d_{6}$): 0.78 (t, 3H, J=7.0 Hz); 1.16-1.26 (m, 4H); 1.65-1.78 (m, 4H); 2.04-2.13 (m, 2H); 2.21-2.29 (m, 2H); 2.42-2.58 (2H, superimposed with the DMSO signal); 5.25 (s, 1H); 6.55 (t, 1H, J=7.2 Hz); 6.77 (d, 2H, J=7.7 Hz); 7.03 (d, 2H, J=7.3 Hz); 7.07 (d, 2H, J=7.3 Hz).

Structural Unit E-12

4-(8-Butyl-1,4-dioxaspiro[4.5]dec-8-yl)morpholine (C-12)

In a thoroughly heated flask, a solution of morpholine (4.79 g, 4.8 ml, 55 mmol), 1,4-dioxaspiro[4.5]dec-8-one (7.8 g, 50 mmol) and 1,2,3-triazole (4.14 g, 60 mmol) in toluene (50 ml) was heated under reflux for 7 hours in a water separator. The solution was cooled to 0° C. and then a 2 M solution of n-butylmagnesium chloride in tetrahydrofuran (100 ml, 200 mmol) was added dropwise, under argon, in such a manner that the internal temperature remained below 30° C. The reaction mixture was stirred for 2 h at room temperature and then added dropwise, while cooling with ice-water, to 20% ammonium chloride solution (120 ml). The organic phase was separated, and the aqueous phase was extracted with ethyl acetate (3×100 ml). The combined organic phases were washed with 2 N sodium hydroxide solution (100 ml) and water (100 ml), dried with sodium sulfate and concentrated in vacuo. The crude product (7.67 g) was purified by flash chromatography (400 g, 20×7.5 cm) with ethyl acetate/cyclohexane (1:2).

Yield: 3.86 g (27%), colorless oil $^{1}$H-NMR (CDCl$_{3}$): 0.88 (t, J=6.9 Hz, 3H); 1.14-1.73 (m, 12H); 1.88 (dt, J=12.6, 3.4 Hz, 2H); 2.44-2.61 (m, 4H); 3.56-3.73 (m, 4H); 3.93 (m, 4H).

4-Butyl-4-morpholin-4-ylcyclohexanone (E-12)

6 M hydrochloric acid (5 ml) was added to a solution of C-12 (3.40 g, 12 mmol) in acetone (20 ml). After 24 h, further 6 M hydrochloric acid (2.5 ml) was added to the reaction solution, stirring was carried out for a further 20 h at room temperature, and then the mixture was rendered alkaline (pH ~10) with 25% potassium carbonate solution and extracted with diethyl ether (3×25 ml). The combined organic phases were dried with sodium sulfate and concentrated in vacuo. The crude product (2.7 g) was purified by flash chromatography (200 g, 20×5.6 cm) with ethyl acetate/cyclohexane (1:4).

Yield: 2.18 g (76%), colorless oil $^{1}$H-NMR (CDCl$_{3}$): 0.90 (t, 3H, J=7.0 Hz); 1.09-2.23 (m, 12H); 2.55 (dd, 2H, J=14.3, 5.8 Hz); 2.59-2.65 (m, 4H); 3.67-3.73 (m, 4H).

Structural Unit E-13

Benzyl-(1,4-dioxaspiro[4.5]dec-8-ylidene)amine

4 Å molecular sieve (20 g) and benzylamine (8.90 g, 83 mmol) were added to a solution of 1,4-dioxaspiro[4.5]decan-8-one (10.0 g, 64 mmol) in dichloromethane (100 ml), and the reaction mixture was stirred for 16 h at room temperature. The suspension was then filtered and the filtrate was concentrated in vacuo.

Yield: 15.6 g (99%), yellowish oil $^{1}$H-NMR (300 MHz, CDCl$_{3}$): 1.83 (t, J=6.3 Hz, 2H); 1.92 (t, J=6.6 Hz, 2H); 2.53 (s, 4H); 3.98 (s, 4H); 4.54 (s, 2H); 7.25 (m, 5H).

$^{13}$C-NMR (100 MHz, CDCl$_{3}$): 25.6; 34.2; 34.9; 36.3; 54.6; 64.4; 108.0; 126.6; 127.9; 128.4; 140.2; 171.7.

(8-Allyl-1,4-dioxaspiro[4.5]dec-8-yl)-benzyl-amine (C-13)

A 1 M solution of allylmagnesium bromide (127 ml, 127 mmol) was added dropwise to a solution of benzyl-(1,4-dioxaspiro[4.5]dec-8-ylidene)amine (15.6 g, 63.7 mmol) in dichloromethane (120 ml), and the reaction mixture was stirred for 72 h at room temperature. The mixture was then poured carefully onto saturated ammonium chloride solution (100 ml), while cooling with ice, and extraction with dichloromethane (3×40 ml) was carried out. The combined organic phases were dried with sodium sulfate and concentrated in vacuo, and the residue was purified by flash chromatography (400 g, 20×7.6 cm) with chloroform/methanol (10:0.2).

Yield: 5.92 g (32%), brown oil $^{1}$H-NMR (300 MHz, $d_{6}$-DMSO): 1.25-1.52 (m, 4H); 1.53-1.66 (m, 2H); 1.74-1.87 (m, 2H); 2.20 (d, J=7.4 Hz, 2H); 3.59 (s, 2H); 3.83 (s, 4H); 4.89-5.19 (m, 2H); 5.86 (tdd, J=14.9, 10.4, 7.3 Hz, 1H); 7.20 (t, J=7.0 Hz, 1H); 7.20-7.35 (m, 4H).

$^{13}$C-NMR (100 MHz, $d_{6}$-DMSO): 29.9; 32.0; 41.9; 44.9; 52.7; 63.4; 63.4; 108.3; 117.2; 126.3; 127.8; 127.9; 134.8; 141.8.

4-Allyl-4-benzylaminocyclohexanone (E-13)

Concentrated hydrochloric acid (2 ml) was added to a solution of C-13 (500 mg, 1.74 mmol) in acetone (20 ml) and water (2 ml), and the mixture was stirred for 16 h at room temperature. Then sodium hydrogen carbonate solution (40 ml) was added to the reaction mixture, and extraction with ethyl acetate (3×40 ml) was carried out. The combined organic phases were dried with sodium sulfate and concentrated in vacuo.

Yield: 423 mg (100%), brown oil $^{1}$H-NMR (300 MHz, $d_{6}$-DMSO): 1.64 (dt, J=13.2, 4.9 Hz, 2H); 1.75-1.97 (m, 2H); 2.04 (dd, J=14.8, 3.4 Hz, 2H); 2.31 (d, J=7.3 Hz, 2H); 2.46-2.65 (m, 2H); 3.68 (s, 2H); 5.03-5.20 (m, 2H); 5.81-6.00 (m, 1H); 7.14-7.26 (m, 1H); 7.26-7.35 (m, 2H); 7.39 (m, 2H). The NH signal could not be identified.

$^{13}$C-NMR (100.4 MHz, $d_{6}$-DMSO): 33.8; 36.4; 41.4; 45.0; 52.8; 117.2; 117.5; 126.4; 127.9; 134.5; 141.5; 211.1.

Structural Unit E-14

1-(8-Pyrrolidin-1-yl-1,4-dioxaspiro[4.5]dec-8-yl)-1H-[1,2,3]triazole

Pyrrolidine (1.95 g, 2.29 ml, 27.5 mmol), 1,2,3-triazole (2.07 g, 30 mmol) and 4 Å molecular sieve (7.14 g) were added to a solution of 1,4-dioxaspiro[4.5]decan-8-one (3.9 g, 25 mmol) in toluene (40 ml). The mixture was stirred for 7 h at 90° C. Then the solution was decanted and immediately reacted further.

1-(8-Butyl-1,4-dioxaspiro[4.5]dec-8-yl)pyrrolidine (C-14)

The triazole compound just prepared (about 6.9 g, 25 mmol) in toluene (38 ml) was added dropwise, under argon and while cooling with ice, to a 2 M solution of n-butylmagnesium chloride (25 ml, 50 mmol) in tetrahydrofuran. The reaction mixture was stirred overnight at room temperature and then poured into saturated ammonium chloride solution (60 ml). The phases were separated and the aqueous phase was extracted with diethyl ether (3×70 ml). The combined organic phases were dried with sodium sulfate and concentrated in vacuo, and the residue (12 g) was purified by flash chromatography (400 g, 20×7.6 cm) with ethyl acetate/methanol (9:1).

Yield: 2.70 g (40% over two stages), brown oil (C-14)

$^1$H-NMR (DMSO-$d_6$): 0.87 (t, 3H, J=7.1 Hz); 1.12-1-29 (m, 4H); 1.30-1.45 (m, 4H); 1.46-1.60 (m, 4H); 1.61-1.75 (m, 6H); 1.93 (t, 1H, J=7.1 Hz); 2.36 (t, 1H, J=7.0 Hz), 2.58 (br s, 2H), 3.83 (s, 4H).

4-Butyl-4-pyrrolidin-1-yl-cyclohexanone (E-14)

Water (10.0 ml) and 37% hydrochloric acid (14.0 ml) were added to a solution of C-14 (2.70 g, 10.1 mmol) in acetone (100 ml), and the mixture was stirred overnight at room temperature. 4 M sodium hydroxide solution was then slowly added dropwise to the mixture until the pH reached 10. The mixture was extracted with diethyl ether (4×40 ml), and the combined organic phases were dried with sodium sulfate and concentrated in vacuo. The crude product (2.6 g) was purified by flash chromatography (260 g, 30×5.6 cm) with ethyl acetate/methanol (9:1).

Yield: 1.06 g (47%), brown oil (E-14)

$^1$H-NMR (DMSO-$d_6$): 0.88 (t, 3H, J=6.7 Hz); 1.14-1.34 (m, 4H); 1.40-1.50 (m, 2H); 1.62-1.88 (m, 8H); 2.04 (dt, 2H, J=15.0, 3.9 Hz); 2.42 (ddd, 2H, J=6.3, 11.8, 15.5 Hz); 2.63 (t, 4H, J=6.0 Hz).

Structural Unit E-15

4-(8-[1,2,3]Triazol-1-yl-1,4-dioxaspiro[4.5]dec-8-yl)piperidine

In a thoroughly heated flask, 4 Å molecular sieve was added to a solution of piperidine (1.87 g, 2.17 ml, 22 mmol), 1,4-dioxaspiro[4.5]dec-8-one (3.12 g, 20 mmol) and 1,2,3-triazole (1.66 g, 24 mmol) in toluene (20 ml), and the mixture was stirred for 7 h under reflux at 104° C. This solution was then decanted off from the molecular sieve. The molecular sieve was washed with toluene and filtered out. The combined liquid phases were reacted further as a 0.6 M solution.

4-(8-Butyl-1,4-dioxaspiro[4.5]dec-8-yl)piperidine (C-15)

In a thoroughly heated flask, a 0.6 M solution of the triazole compound just prepared in toluene (18 ml, 11 mmol) was added dropwise at 0° C., in the course of 1 h, under argon, to a 2 M solution of n-butylmagnesium chloride in tetrahydrofuran (22 ml, 44 mmol). The mixture was stirred for 2 h at room temperature and then added dropwise, while cooling with ice-water, to 20% ammonium chloride solution (24 ml). The organic phase was separated, and the aqueous phase was extracted with diethyl ether (4×20 ml). The combined organic phases were washed with 2 N sodium hydroxide solution (30 ml) and water (20 ml), dried with sodium sulfate and concentrated in vacuo. The crude product (1.9 g) was purified by flash chromatography (100 g, 22×4 cm) with ethyl acetate/cyclohexane (1:2).

Yield: 1.03 g (33%), colorless oil (C-15)

$^1$H-NMR (DMSO-$d_6$): 0.86 (t, 3H, J=6.9 Hz); 1.09-1.52 (m, 16H); 1.60-1.79 (m, 4H); 2.44 (br s, 4H), 3.82 (s, 4H).

4-Butyl-4-piperidin-4-ylcyclohexanone (E-15)

6 M hydrochloric acid (5 ml) was added to a solution of C-15 (1.0 g, 3.6 mmol) in acetone (15 ml). The reaction solution was stirred for 6 d at room temperature, then rendered alkaline (pH ~9) with 25% potassium carbonate solution and extracted with diethyl ether (3×20 ml). The combined organic phases were dried with sodium sulfate and concentrated in vacuo.

Yield: 860 mg (100%), colorless oil (E-15)

$^1$H-NMR (DMSO-$d_6$): 0.87 (t, 3H, J=6.9 Hz); 1.06-1.54 (m, 14H); 1.54-1.74 (m, 3H); 1.88-2.07 (m, 4H); 2.21-2.46 (m, 3H).

Structural Unit E-16

1-Methyl-4-(8-[1,2,3]triazol-1-yl-1,4-dioxaspiro[4.5]dec-8-yl)piperazine

In a thoroughly heated flask, a solution of N-methylpiperazine (2.60 g, 2.88 ml, 26 mmol), 1,4-dioxaspiro[4.5]decan-8-one (3.90 g, 25 mmol) and 1,2,3-triazole (1.87 g, 27 mmol) in toluene (25 ml) was heated for 6 h under reflux in a water separator. The reaction solution was then transferred to a closable measuring cylinder and the crude product was used further in.

1-(8-Butyl-1,4-dioxaspiro[4.5]dec-8-yl)-4-methylpiperazine (C-16)

A 2 M n-butylmagnesium chloride solution in tetrahydrofuran (15 ml, 30 mmol) was added dropwise, under argon, to a solution of the triazole compound just prepared (12.5 mmol) in toluene (12 ml) in such a manner that the internal temperature remained below 24° C. When the addition was complete, the reaction mixture was stirred for 2 h at room temperature and then cooled to 0° C. and added dropwise to a 20% ammonium chloride solution (50 ml); the aqueous phase was extracted with diethyl ether (3×40 ml), and the combined organic phases were washed with 2 N sodium hydroxide solution (70 ml) and water (70 ml), dried with sodium sulfate and concentrated in vacuo.

The crude product C-16 (3.57 g) was reacted further.

4-Butyl-4-(4-methylpiperazin-1-yl)cyclohexanone (E-16)

First water (2.5 ml) and then concentrated hydrochloric acid (2.5 ml) were added to a solution of C-16 (3.57 g, 12.0 mmol) in acetone (15 ml), and the mixture was stirred over the weekend at room temperature. Then the reaction mixture was rendered alkaline (pH 10) with 2 M potassium carbonate solution and extracted with diethyl ether (3×40 ml), and the combined organic phases were dried with sodium sulfate and concentrated in vacuo. The crude product was purified by means of flash chromatography (200 g, 20×5.7 cm) with methanol.

Yield: 2.04 g (67%), yellow oil (E-16)

$^1$H-NMR (DMSO-$d_6$): 0.87 (t, 3H, J=7.0 Hz); 1.16-1.28 (m, 4H); 1.37-1.43 (m, 2H); 1.66 (dt, 2H, J=13.5, 4.5 Hz); 1.90-2.02 (m, 4H); 2.15 (s, 3H); 2.28-2.43 (m, 6H); 2.53-2.57 (m, 4H).

$^{13}$C-NMR: 13.9; 23.2; 26.3; 31.0 (2C); 31.9; 36.1 (2C); 44.0 (2C); 45.7; 55.5; 55.8; 210.4.

Structural Unit E-17

8-(Cyclopentylmethyl)-N,N-dimethyl-1,4-dioxaspiro[4.5]decan-8-amine

A solution of iodomethylcyclopentane (31.5 g, 150 mmol) in abs. ether (150 ml) was added dropwise to a mixture of magnesium (3.64 g, 150 mmol) in abs. ether (30 ml) in such a manner that the ether boiled slightly. Then the reaction solution was boiled under reflux for 30 min. and cooled to RT, and a solution of 8-dimethylamino-1,4-dioxa-spiro[4.5]decane-8-carbonitrile B-1 (10.5 g, 50 mmol) in abs. THF (100 ml) was added dropwise. The reaction solution began to boil and a white solid precipitated. Boiling was carried out for 6 h under reflux, followed by stirring overnight at RT. For working up of the reaction mixture, 20% NH$_4$Cl solution (200 ml) was added, while cooling with ice, and extraction with ether (3×100 ml) was carried out. The organic phase was dried over Na$_2$SO$_4$ and concentrated in vacuo. The residue that remained was purified by flash chromatography with EA/EtOH (20:1).
13.4 g (100%)
$^1$H-NMR (DMSO-d$_6$): 1.04 (2H, m); 1.37 (4H, m); 1.45-1.78 (17H, m); 2.13 (6H, s); 3.62 (4H, s).

4-Cyclopentylmethyl-4-dimethylamino-cyclohexanone (E-17)

5% sulfuric acid (600 ml) was added at room temperature to (8-cyclopentylmethyl-1,4-dioxa-spiro[4.5]dec-8-yl)-dimethyl-amine (13.4 g, 50 mmol), and the mixture was stirred for 3 d at RT. The reaction mixture was extracted with ether (2×50 ml). Then the aqueous phase was rendered alkaline with 5N NaOH, while cooling with an ice bath, and extraction with dichloromethane (3×50 ml) was carried out. The organic phase was dried over Na$_2$SO$_4$ and concentrated to dryness in vacuo.
Yield: 8.46 g (76%), colorless crystals.
$^1$H-NMR (DMSO-d$_6$): 1.04 (2H, m); 1.48 (6H, m); 1.83 (5H, m); 1.93 (4H, m); 2.20 (6H, s); 2.44 (2H, m).
$^{13}$C-NMR (DMSO-d$_6$): 24.7; 31.7; 34.6; 35.4; 36.1; 36.2; 36.9; 55.9; 210.4.

Indole Structural Units

F & H

Structural Unit F-1

Tryptophol (F-1) (CAS.: 526-55-6), available commercially

Structural Unit F-2

(5-Fluoro-3-hydroxy-2-oxo-2,3-dihydro-1H-indol-3-yl)acetic acid ethyl ester[1]

5-Fluoristatin (10 mmol) was dissolved in a mixture of ethanol/pyridine/acetic acid (50 ml, 15:5:2); ethyl potassium malonate (1.87 g, 11 mmol) was added, and the mixture was heated for 14 h at reflux. The progress of the reaction was monitored by means of TLC (eluant:ethyl acetate/hexane 1:1). For working up, the solvent mixture was distilled off in vacuo. The residue was taken up in ethyl acetate (50 ml) and extracted by shaking with water (50 ml). After phase separation, the aqueous phase was extracted twice with ethyl acetate (30 ml each time). The combined organic phases were washed with 2N HCl (50 ml), dried over Na$_2$SO$_4$ and concentrated to 20 ml in vacuo. Hexane was added to the solution until crystallisation of the desired product began. In order to complete the crystallisation, the mixture was cooled for 12 h at 10° C. The solid was filtered out with suction and dried in vacuo.
Yield: 89%.

[1]S. J. Garden, R. B. da Silva, A. C. Pinto, Tetrahedron 2002, 58, 8399-8412 (especially page 8406).

2-(5-Fluoro-1H-indol-3-yl)ethanol (F-2)[2]

The resulting aldol product (10 mmol) was dissolved in absolute THF (20 ml), under an Ar atmosphere. BH$_3$×THF (40 ml, 1 M solution, 40 mmol) was then added to the mixture, while cooling with a water bath, and stirring was carried out for 14 h at room temperature. The progress of the reaction was monitored by means of TLC. When the reaction was complete, the reaction solution was added to a mixture of ethyl acetate (50 ml) and H$_2$O (50 ml). After phase separation, the aqueous phase was extracted twice with ethyl acetate (30 ml each time). The combined organic phases were dried over Na$_2$SO$_4$ and concentrated in vacuo. The residue was filtered over silica gel with ethyl acetate. The product (F-2) obtained after removal of the solvent was in most cases in the form of a sufficiently pure oil and crystallised spontaneously. Purification by column chromatography on silica gel was carried out where necessary. Yield 95%.

[2]S. J. Garden, R. B. da Silva, A. C. Pinto, Tetrahedron 2002, 58, 8399-8412.

Structural Unit F-3

3-(2-Hydroxy-ethyl)-1H-indole (F-3)

LiAlH$_4$ (1.99 g, 52.3 mmol) was placed in abs. THF (60 ml), under argon, and (5-hydroxy-1H-indol-3-yl)-acetic acid (5.00 g, 26.2 mmol) in abs. THF (100 ml) was added in the course of 30 min. The mixture was boiled for 3 h under reflux. For working up, THF (10 ml) and H$_2$O (4 ml) were added to the mixture, while cooling with ice, and stirring was carried out for 30 min. The mixture was filtered over Celite and rinsed with dichloromethane (150 ml), and the filtrate was concentrated in vacuo.
Yield: 2.17 g (47%)
$^1$H-NMR (DMSO-d$_6$): 2.74 (2H, m); 3.60 (3H, m); 6.58 (1H, m); 6.78 (1H, s); 6.99 (1H, s); 7.08 (1H, d); 10.5 (1H, bs).

Example AA-1

4',9'-Dihydro-N,N-dimethyl-4-ethyl-spiro[cyclohexane-1,1'(3'H)-pyrano[3,4-b]indol]-4-amine, 2-hydroxy-1,2,3-propanetricarboxylate (2:1) (one of two possible diastereoisomers)

Tryptophol F-1 (484 mg, 3.00 mmol) and ketone E-1 (507 mg, 3.00 mmol) were dissolved in dichloromethane (25 ml), and methanesulfonic acid (316 mg, 3.30 mmol) was added. The reaction solution was stirred overnight at room temperature. Methanesulfonic acid (316 mg, 3.30 mmol) was added again and stirring was carried out for a further 3 h. The reaction solution was rendered alkaline with 1N NaOH, the organic phase was separated, and the aqueous phase was extracted three times with dichloromethane (15 ml). The combined organic phases were dried over Na$_2$SO$_4$ and filtered, and the solvent was removed under reduced pressure. The crude product was purified by column chromatography with CHCl$_3$/EtOH (10:1).

Yield: 672 mg (72%); white solid $^1$H-NMR (DMSO-d$_6$): 0.85 (3H, t); 1.23-1.75 (8H, br. m); 2.14 (2H, br. m); 2.28 (6H, br. s); 2.01 (6H, s); 2.66 (2H, t); 3.89 (2H, t); 6.93 (1H, t); 7.01 (1H, t); 7.29-7.37 (2H, 2 d); 10.80 (br, 1H).

The corresponding citrate was formed from the spiroether just prepared (0.66 g, 2.11 mmol) in hot EtOH (10 ml) and citric acid (405 mg, 2.11 mmol) dissolved in hot EtOH (2 ml). Stirring was carried out for 2 h at room temperature. The resulting solid AA-1 was filtered out with suction and dried.

Yield: 889 mg (82%), white solid (AA-1)

Melting point: 240-242° C.

$^1$H-NMR (DMSO-d$_6$): 0.89 (3H, t); 1.53 (2H, m); 1.62 (4H, br. t); 1.67 (2H, br. t); 2.12 (2H, br. t); 2.55 (6H, s); 2.57-2.70 (4H, m); 3.90 (2H, t); 6.97 (1H, t); 7.05 (1H, t); 7.35-7.39 (2H, 2 d); 10.73 (1H, br).

$^{13}$C-NMR (DMSO-d$_6$): 8.86; 22.15; 23.47; 25.22; 37.17; 44.19; 59.08; 71.23; 72.07; 99.65; 105.28; 111.35; 117.62; 118.39; 120.65; 126.38; 135.61; 139.04; 171.84.

Example AA-2

6'-Fluoro-4',9'-dihydro-N,N-dimethyl-4-ethyl-spiro [cyclohexane-1,1'(3'H)-pyrano[3,4-b]indol]-4-amine, 2-hydroxy-1,2,3-propanetricarboxylate (1:1) (less polar diastereoisomer)

4-Dimethylamino-4-ethyl-cyclohexanone E-1 (600 mg, 3.55 mmol) and 5-fluoro-tryptophol F-2 (852 mg, 3.55 mmol) were placed, under argon, in abs. CH$_2$Cl$_2$ (15 ml), and then methanesulfonic acid (250 µl, 3.89 mmol) was added. The mixture was stirred for 72 h at room temperature; 1N NaOH was added until the reaction was alkaline, and extraction with CH$_2$Cl$_2$ (3×20 ml) was carried out. The organic phase was dried over Na$_2$SO$_4$ and concentrated in vacuo. The residue was purified by flash chromatography with CHCl$_3$/MeOH (20:1, 4:1, 1:1+1% TEA).

The resulting less polar cyclization product (164 mg, 0.496 mmol) was dissolved in hot ethanol (5 ml), and citric acid (90 mg, 0.496 mmol) dissolved in hot ethanol was added. The mixture was cooled to room temperature, and the resulting precipitate AA-2 was filtered out with suction and dried in vacuo.

Yield: 124 mg (7%) (AA-2)

Melting point: 233-236° C.

$^1$H-NMR (DMSO-d$_6$): 0.88 (3H, t); 1.47 (2H, m); 1.53-1.87 (8H, m); 2.05 (2H, t); 2.48 (6H, m); 2.60 (4H, m); 3.91 ((2H, t); 6.83 (1H, m); 7.12 (1H, m); 7.35 (1H, m); 10.74 (1H, s).

Example AA-3

2',3',4',9'-Tetrahydro-N,N-dimethyl-4-ethyl-spiro [cyclohexane-1,1'(1'H)-pyrido-[3,4-b]indol]-4-amine, 2-hydroxy-1,2,3-propanetricarboxylate (1:1) (one of two possible diastereoisomers)

Tryptamine H-1 (528 mg, 3.30 mmol) and ketone E-1 (507 mg, 3.30 mmol) were dissolved in methanol (15 ml) and stirred overnight. The methanol was removed under reduced pressure, the residue was taken up in dichloroethane (15 ml), and trifluoroacetic acid (494 mg, 3.30 mmol) was added. The reaction solution was stirred for 72 h at room temperature and rendered alkaline with 1N NaOH, the organic phase was separated, and the aqueous phase was extracted three times with dichloromethane (15 ml). The combined organic phases were dried over NaSO$_4$ and filtered, and the solvent was removed under reduced pressure. The crude product was purified by column chromatography with CHCl$_3$/MeOH (1:4).

Yield: 265 mg (26%), white solid $^1$H-NMR (DMSO-d$_6$): 0.85 (3H, t); 1.32-1.48 (6H, br. m); 1.82 (2H, br. t); 2.11 (2H, br. t); 2.25 (6H, s); 2.53 (2H, t); 2.96 (2H, t); 6.78 (2H, dt); 6.95 (1H, dt); 7.29 (2H, d); 10.49 (br, 1H).

$^{13}$C-NMR (DMSO-d$_6$): 9.25; 22.87; 23.47; 26.21; 30.66; 38.66; 51.31; 55.49; 106.23; 110.85; 116.94; 117.64; 119.76; 126.77; 135.35; 144.85.

The corresponding citrate was formed from the spiroamine just prepared (0.25 g, 0.80 mmol) in hot EtOH (10 ml) and citric acid (0.15 g, 0.80 mmol) dissolved in hot EtOH (1 ml). Stirring was carried out for 2 h at room temperature. The resulting solid AA-3 was filtered out with suction and dried.

Yield: 347 mg (86%), white solid

Melting point. 228-230° C.

$^1$H-NMR (DMSO-d$_6$): clean, but very broad signals, therefore no allocation.

$^{13}$C-NMR (DMSO-d$_6$): 9.01; 23.77; 25.62; 28.83; 37.09; 44.23; 55.47; 71.23; 105.42; 111.22; 117.64; 118.52; 121.22; 125.82; 135.76; 171.01.

Example AA-4

4',9'-Dihydro-N,N-dimethyl-4-butyl-spiro[cyclohexane-1,1'(3'H)-pyrano[3,4-b]-indol]-4-amine, 2-hydroxy-1,2,3-propanetricarboxylate (1:1) (one of two possible diastereoisomers)

The cyclohexanone ??? E-2 (394 mg, 2 mmol) and tryptophol F-1 (322 mg, 2 mmol) were placed, under argon, in abs. CH$_2$Cl$_2$ (15 ml). Methanesulfonic acid (142 µl, 2.2 mmol) was then added and stirring was carried out for 24 h at room temperature. In order to work up the reaction mixture, 1N NaOH was added, and extraction with CH$_2$Cl$_2$ (3×15 ml) was carried out. The organic phase was dried over Na$_2$SO$_4$ and concentrated in vacuo. The residue was purified by flash chromatography with CHCl$_3$/MeOH (9:1) and then recrystallised from ethanol.

Yield: 330 mg (49%)

The NMR spectra of the free base were evaluated because the spectra of the citrate were poorly resolved.

$^1$H-NMR (DMSO-d$_6$): 0.91 (3H, t); 1.25 (6H, m); 1.55 (4H, m); 1.73 (2H, m); 2.11 (2H, m); 2.26 (6H, s); 2.66 (2H, t); 3.91 (2H, t); 6.98 (2H, m); 7.32 (2H, m); 10.72 (1H, s).

$^{13}$C-NMR (DMSO-d$_6$): 14.04; 18.50; 22.18; 23.37; 26.61; 26.99; 29.93; 30.79; 37.24; 55.14; 55.97; 58.75; 71.99; 104.90; 111.21; 117.41; 118.19; 120.33; 126.42; 135.81; 139.74.

The corresponding citrate was formed from the spiroether just prepared (150 mg, 0.44 mmol), which was dissolved in hot ethanol (5 ml) and to which citric acid (84 mg, 0.44 mmol) dissolved in hot ethanol (1 ml) was added. The solution was then cooled to room temperature and stirred for 2 h. The resulting white precipitate AA-4 was filtered out with suction and dried in vacuo.

Yield: 180 mg (77%) (AA-4)

Melting point: 210-214° C.

Example AA-5

6'-Fluoro-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate (2:1) (one of two possible diastereoisomers)

4-Butyl-4-dimethylamino-cyclohexanone E-2 (394 mg, 2 mmol) and 5-fluoro-tryptophol F-2 (482 mg, 2 mmol) were placed, under argon, in abs. $CH_2Cl_2$ (15 ml), and then trifluoromethanesulfonic acid (194 µl, 2.2 mmol) was added. The mixture was stirred for 72 h at room temperature. For working up, 1N NaOH was added to the solution, and extraction with $CH_2Cl_2$ (3×15 ml) was carried out. The organic phase was dried over $Na_2SO_4$ and concentrated in vacuo. The residue was purified by flash chromatography with $CHCl_3$/MeOH (9:1 to 1:1). For further purification, the product was recrystallised from ethanol.

Yield: 119 mg (16%)

The NMR spectra of the free base were evaluated because the spectra of the citrate were poorly resolved.

$^1$H-NMR (DMSO-$d_6$): 0.90 (3H, t); 1.19 (6H, m); 1.54 (4H, m); 1.67 (2H, m); 2.12 (2H, m); 2.24 (6H, s); 2.59 (2H, t); 3.88 (2H, t); 6.83 (1H, m); 7.12 (1H, m); 7.28 (1H, m); 10.85 (1H, s).

$^{13}$C-NMR (DMSO-$d_6$): 14.03; 18.49; 22.10; 23.36; 26.59; 26.93; 29.87; 30.74; 37.22; 55.12; 55.97; 58.69; 72.01; 102.16; 102.39; 105.39; 108.00; 108.26; 111.90; 111.99; 126.55; 126.65; 132.43; 141.93; 155.56; 157.85.

The corresponding citrate was formed from the spiroether just prepared. This spiro compound (119 mg, 0.33 mmol) was dissolved in hot ethanol (5 ml), and citric acid (63 mg, 0.33 mmol) dissolved in hot ethanol was added. The mixture was cooled to room temperature, and the resulting white precipitate (AA-5) was filtered out with suction and dried in vacuo.

Yield: 106 mg (58%) (AA-5)

Melting point: 217-220° C.

Example AA-6

6'-Fluoro-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate (1:1) (one of two possible diastereoisomers)

Example AA-6 was prepared analogously to Example AA-5. In the citrate precipitation, however, the citrate was isolated instead of the hemicitrate. E-2 (4.0 g/20.3 mmol) and fluorotryptophol F-2 (4.89 g/20.3 mmol) were placed, under argon, in abs. $CH_2Cl_2$ (50 ml). Then methanesulfonic acid (1.44 ml/22.33 mmol) was added and the mixture was stirred for 48 h at room temperature. For working up, 1N NaOH was added to the mixture, and vigorous stirring was carried out for 10 min. The phases were separated, and the aqueous phase was extracted with $CH_2Cl_2$ (1×30 ml), whereupon a solid precipitated, which was filtered out with suction and recrystallized from ethanol. The organic phase was dried over $Na_2SO_4$ and concentrated in vacuo. The residue was likewise recrystallized from ethanol. Both solids were target product.

Yield: 1.9 g (26%)

The resulting cyclization product (1.0 g, 2.77 mmol) was dissolved in hot ethanol (5 ml). Citric acid (0.528 g, 2.77 mmol) dissolved in hot ethanol was added. The mixture was cooled to room temperature, whereupon a white precipitate formed. The precipitate (AA-6) was filtered out with suction and dried in vacuo.

Yield: 1.5 g (98%) (AA-6)

Example AA-7

6'-Hydroxy-4',9'-dihydro-N,N-dimethyl-4-butyl-spiro[cyclohexane-1,1'(3'H)-pyrano[3,4-b]indol]-4-amine, 2,2,2-trifluoroacetate (1:1) (one of two possible diastereoisomers)

3-(2-Hydroxy-ethyl)-1H-indole F-3 (620 mg, 3.49 mmol) and ketone E-2 (680 mg, 3.49 mmol) were placed, under argon, in abs. $CH_2Cl_2$ (100 ml); TMS triflate (686 µl, 3.55 mmol) in $CH_2Cl_2$ (2 ml) was added, while cooling with ice, and the mixture was stirred for 30 min. at room temperature. The mixture was stirred for a further 16 h at room temperature. For working up, $H_2O$ (22 ml) and $K_2CO_3$ (490 mg, 3.55 mmol) were added and stirring was carried out for 20 min. at room temperature. The phases were separated. The aqueous phase was extracted with dichloromethane (2×20 ml). The organic phase was dried over $Na_2SO_4$ and concentrated in vacuo. The resulting cyclization product (100 mg, 0.273 mmol) was dissolved in hot ethanol (5 ml). Citric acid (52 mg, 0.273 mmol) dissolved in hot ethanol was added. The mixture was cooled to room temperature, whereupon a white precipitate formed. The precipitate AA-7 was dried in vacuo.

Yield: 48 mg (31%), according to NMR no citrate signals are present

Note: Trifluoroacetic acid was probably carried in by mistake, so that a trifluoroacetic acid salt was obtained instead of the desired citrate.

Yield: 109 mg (9%) (AA-7)

Melting point: 265-269° C.

1H-NMR (DMSO-d6): 0.94 (3H, t); 1.29 (4H, m); 1.60 (2H, m); 1.81 (4H, t); 1.96 (2H, t); 2.40 (4H, m); 2.59 (6H, m); 3.87 (2H; t); 6.55 (1H, d); 6.70 (1H, s); 7.04 (1H, d); 8.54 (1H, s); 9.45 (1H, bs): 10.98 (1H, bs).

13C-NMR (DMSO-d6): 13.77; 22.14; 22.70; 24.86; 26.07; 29.10; 30.94; 37.12; 59.36; 66.16; 70.51; 101.97; 104.52; 110.81; 111.05; 126.74; 129.56; 138.88; 150.28 (free base).

Example AA-8

6'-Hydroxy-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate (2:3) (one of two possible diastereoisomers)

3-(2-Hydroxy-ethyl)-1H-indole F-3 (2.68 g, 15.09 mmol) and ketone E-2 (2.94 g, 15.09 mmol) were placed, under argon, in abs. $CH_2Cl_2$ (100 ml); the triflate (2.96 ml, 15.34 mmol) in $CH_2Cl_2$ (5 ml) was added, while cooling with ice, and stirring was carried out for 30 min. at room temperature. The mixture was stirred for a further 16 h at room temperature. For working up, $H_2O$ (110 ml) and $K_2CO_3$ (2.45 g) were added and stirring was carried out for 20 min. at room temperature. The phases were separated. The aqueous phase was extracted with dichloromethane (2×20 ml). The organic phase was dried over $Na_2SO_4$ and concentrated in vacuo. The residue was purified by flash chromatography with $CHCl_3$/MeOH (9:1) and recrystallised from ethyl acetate.

Yield: 476 mg (9%)

The resulting spiroether (471 mg, 1.32 mmol) was dissolved in hot ethanol (5 ml). Citric acid (245 mg, 1.32 mmol) dissolved in hot ethanol was added. The mixture was cooled to room temperature, whereupon a white precipitate did not form. The mixture was concentrated to dryness in vacuo.

Yield: 524 mg (72%) (AA-8)

Example AA-9

2',3',4',9'-Tetrahydro-N,N-dimethyl-4-butyl-spiro
[cyclohexane-1,1'(1'H)-pyrido[3,4-b]indol]-4-amine,
2-hydroxy-1,2,3-propanetricarboxylate (1:1) (less
polar diastereoisomer)

Tryptamine H-1 (2.43 g, 15.2 mmol) and the ketone E-2 (3.0 g, 15.2 mmol) were dissolved in abs. methanol (90 ml), and the solution was stirred for 25 h at room temperature, under argon. The reaction mixture was then concentrated. The residue was dissolved in abs. 1,2-dichloroethane (150 ml); trifluoroacetic acid (10.4 ml, 15.5 g, 136 mmol) was added quickly and stirring was carried out for 3 d at room temperature. 1N sodium hydroxide solution (130 ml) was added to the brown solution, while cooling with ice, and the mixture was stirred for 20 min. at room temperature. The phases of the solution were separated. The aqueous phase was extracted with 1,2-dichloroethane (2×70 ml). The organic phases were combined, washed with water (50 ml), dried and concentrated. Methanol (60 ml) was added to the oily brown residue, which caused crystallization. The suspension was stirred for a further 10 min. The colorless crystals were filtered out with suction and washed with methanol (60 ml) (1.28 g). This was the pure, less polar spiroamine. The filtrate was concentrated; methanol (50 ml) was again added to the resulting brown solid, and the mixture was stirred for 1 h in an ice bath. After filtration with suction and washing with cold methanol (20 ml), 673 mg of the less polar spiroamine were obtained. The filtrate was concentrated and the residue (2.4 g) was separated by chromatography [silica gel 60 (130 g); methanol (500 ml), methanol/triethylamine (100:1, 1.5 liters)]. The less polar spiroamine was obtained together with impurities (1.02 g). Cold methanol (10 ml) was added to this fraction, and filtration with suction was carried out. The resulting solid (332 mg) was pure non-polar product. The less polar spiroamine was obtained in an overall yield of 44% (2.28 g) with a melting point of 180-182° C. The more polar spiroamine was obtained in a further fraction in a yield of 12% (622 mg) with a melting point of 93-96° C.

The resulting less polar spiroamine (92 mg, 0.27 mmol) was dissolved in hot ethanol (5 ml). Citric acid (51 mg, 0.27 mmol) dissolved in hot ethanol was added. The mixture was cooled to room temperature, whereupon a white precipitate formed. The precipitate AA-9 was filtered out and dried in vacuo.

Yield: 58 mg (40%) (AA-9)

Example AA-10

2',3',4',9'-Tetrahydro-N,N-dimethyl-4-butyl-2'-methylcarbonyl-spiro[cyclo-hexane-1,1'(1'H)-pyrido[3,4-b]indol]-4-amine, 2-hydroxy-1,2,3-propane-tricarboxylate (1:1) (less polar diastereoisomer)

Acetyl chloride (0.126 ml, 139 mg, 1.77 mmol) was dissolved in abs. dichloromethane (5 ml), under argon, and the free base of the less polar spiroamine AA-9 (200 mg, 0.59 mmol), dissolved in dichloromethane (15 ml), was added at room temperature, in the course of 30 min. After 15 min., a precipitate was visible, which had dissolved again at the end of the addition. After a reaction time of 30 min., a precipitate formed again. Stirring was carried out for a further 21 h at room temperature. For working up, water (10 ml) and 1N sodium hydroxide solution (5 ml) were added to the colorless mixture, and stirring was carried out for 1 h. The phases were separated. The aqueous phase was extracted with dichloromethane (20 ml). The combined organic phases were washed with water (20 ml), dried and concentrated. A beige-colored oil (277 mg) was obtained and was separated by chromatography [silica gel 60 (35 g); ethyl acetate/methanol (20:1, 300 ml)].

Yield: 56% (125 mg)

Melting point: 163-166° C.

The resulting less polar amide (125 mg, 0.327 mmol) was dissolved at 50° C. in ethanol (5 ml), and an ethanolic solution (3 ml) of citric acid (70 mg, 0.36 mmol) was added. After a reaction time of 3 h at room temperature, the colorless citrate AA-10 was separated by filtration and washed with ethanol (2×3 ml). The less polar amide was obtained in the form of the citrate in a yield of 63% (118 mg) with a melting point of 220-222° C.

Example AA-11

2',3',4',9'-Tetrahydro-N,N-dimethyl-4-butyl-2'-cyclopentylcarbonyl-spiro[cyclohexane-1,1'(1'H)-pyrido
[3,4-b]indol]-4-amine, 2-hydroxy-1,2,3-propanetricarboxylate (2:1) less polar diastereoisomer Cyclopentanecarboxylic acid chloride (0.215 ml, 234 mg, 1.77 mmol) was dissolved in abs. dichloromethane (5 ml), under argon, and the less polar spiroamine (less polar free base of AA-9, 200 mg, 0.59 mmol), dissolved in dichloromethane (15 ml), was added, at room temperature, in the course of 45 min. Stirring was carried out for a further 1.5 h at room temperature. For working up, water (10 ml) and 1N sodium hydroxide solution (5 ml) were added to the colorless mixture, and stirring was carried out for 1 h. The phases were separated. The aqueous phase was extracted with dichloromethane (20 ml). The combined organic phases were washed with water (20 ml), dried and concentrated. A beige-colored oil (325 mg) was thereby obtained and was separated by chromatography [silica gel 60 (40 g); ethyl acetate (350 ml)]. The amide was isolated in the form of a colorless hygroscopic solid in a yield of 87% (222 mg).

The resulting amide (186 mg, 0.427 mmol) was dissolved at 60° C. in ethanol (8 ml), and an ethanolic solution (3 ml) of citric acid (90 mg, 0.47 mmol) was added. Precipitation began immediately. After a reaction time of 2 h at room temperature, the colorless citrate AA-11 was separated by filtration and washed with ethanol (2×3 ml). The less polar amide was obtained in the form of the citrate in a yield of 69% (183 mg) with a melting point of 228-230° C.

Example AA-12

2',3',4',9'-Tetrahydro-N,N-dimethyl-4-butyl-2'-(2,2)-dimethylpropanecarbonyl-spiro[cyclohexane-1,1'
(1'H)-pyrido[3,4-b]indol]-4-amine, 2-hydroxy-1,2,3-propanetricarboxylate (1:1) (less polar
diastereoisomer)

3,3-Dimethylbutyric acid chloride (0.246 ml, 238 mg, 1.77 mmol) was dissolved, under argon, in abs. dichloromethane (5 ml), and the free base of the less polar spiroamine AA-9 (200 mg, 0.59 mmol), dissolved in dichloromethane (15 ml), was added, at room temperature, in the course of 30 min. After a reaction time of 24 h, water (10 ml) and 1N sodium hydroxide solution (5 ml) were added to the yellow reaction solution, and stirring was carried out for 1 h. The phases were separated. The aqueous phase was extracted with dichloromethane (20 ml). The combined organic phases were washed with water (20 ml), dried and concentrated. A beige-colored oil (322 mg) was thereby obtained and was separated by chromatography [silica gel 60 (40 g); ethyl acetate (250 ml), ethyl acetate/methanol (4:1, 400 ml), methanol (300 ml)]. The amide was obtained in the form of a colorless oil in a yield of only 7% (40 mg).

The acylation was repeated as described above. The reaction solution remained colorless. However, the reaction stopped after only 1.5 h. After separation of the reaction mixture by chromatography [silica gel 60 (40 g); ethyl acetate (250 ml)], the amide was obtained in a yield of 78% (200 mg) in the form of a colorless solid with a melting point of 220-222° C.

The resulting less polar amide (230 mg, 0.525 mmol) was dissolved at 50° C. in ethanol (8 ml), and an ethanolic solution (4 ml) of citric acid (111 mg, 0.578 mmol) was added. After a reaction time of 16 h at room temperature, the colorless citrate was separated by filtration and washed with ethanol (2×3 ml). The less polar spiroamine AA-12 was obtained in the form of the citrate in a yield of 66% (219 mg) with a melting point of 216-218° C.

Example AA-13

2',3',4',9'-Tetrahydro-N,N-dimethyl-4-butyl-2'-(3,4-dimethoxybenzylcarbonyl)-spiro[cyclohexane-1,1' (1'H)-pyrido[3,4-b]indol]-4-amine, 2-hydroxy-1,2,3-propanetricarboxylate (1:1) (less polar diastereoisomer)

3,4-Dimethoxyphenylacetyl chloride (380 mg, 1.77 mmol) was dissolved in abs. dichloromethane (5 ml), under argon, and the free base of the less polar spiroamine AA-9 (200 mg, 0.59 mmol), dissolved in dichloromethane (15 ml), was added, at room temperature, in the course of 50 min. A precipitate immediately formed. Stirring was carried out for a further 1.5 h at room temperature. For working up, water (10 ml) and 1N sodium hydroxide solution (5 ml) were added to the mixture, and stirring was carried out for 1 h. The phases were separated. The aqueous phase was extracted with dichloromethane (20 ml). The combined organic phases were washed with water (20 ml), dried and concentrated. A beige-colored oil (357 mg) was thereby obtained and was separated by chromatography [silica gel 60 (40 g); ethyl acetate (250 ml), ethyl acetate/methanol (8:1, 200 ml)]. The amide was isolated in the form of a colorless solid in a yield of 75% (230 mg) with a melting point of 135-140° C.

The resulting less polar amide (216 mg, 0.417 mmol) was dissolved at 60° C. in ethanol (11 ml), and an ethanolic solution (3 ml) of citric acid (89 mg, 0.46 mmol) was added. After a reaction time of 5 h at room temperature, the colorless citrate was separated by filtration and washed with ethanol (2×3 ml). The less polar amide was obtained in the form of the citrate AA-13 in a yield of 92% (270 mg) with a melting point of 188-190° C.

Example AA-14

2',3',4',9'-Tetrahydro-N,N-dimethyl-4-butyl-2'-ethylaminocarbonyl-spiro[cyclohexane-1,1'(1'H)-pyrido [3,4-b]indol]-4-amine, 2-hydroxy-1,2,3-propanetricarboxylate (1:1) (less polar diastereoisomer, sum of rotamers about 95%)

The free base of the less polar spiroamine AA-9 (204 mg, 0.6 mmol) was suspended in abs. acetonitrile (30 ml), and ethyl isocyanate (0.052 ml, 47 mg, 0.66 mmol) was added. The reaction mixture was heated for 6 h at reflux. The clear solution was concentrated. The oily residue was taken up in diethyl ether (20 ml) and washed with water (5 ml). After drying and concentration, the less polar urea was obtained in the form of a colorless solid in a yield of 57% (139 mg) with a melting point of 154-158° C.

The resulting less polar urea (139 mg, 0.4 mmol) was dissolved in ethanol (10 ml), and an ethanolic solution (5 ml) of citric acid (85 mg, 0.44 mmol) was added. After a reaction time of 20 h at room temperature, the colorless citrate was separated by filtration. Because the product had an oily consistency, it was washed with diethyl ether (2×3 ml). It was not possible to obtain further product from the filtrate. The less polar urea was obtained in the form of the citrate AA-14 in a yield of 38% (90 mg) with a melting point of 215-231° C.

Example AA-15

2',3',4',9'-Tetrahydro-N,N-dimethyl-4-butyl-2'-4-methoxybenzylaminocarbonyl-spiro[cyclohexane-1, 1'(1'H)-pyrido[3,4-b]indol]-4-amine (more polar diastereoisomer)

4-Methoxybenzyl isocyanate (0.75 mmol) was dissolved in abs. acetonitrile (30 ml); triethylamine (0.07 ml, 511 mg, 5 mmol) and the free base of the less polar spiroamine AA-9 (170 mg, 0.5 mmol) were added. The reaction mixture was heated for 6 h at boiling, the reaction solution becoming clear. Because no reaction was detectable by TLC, heating was carried out for a further 7 h under reflux. The mixture was concentrated. Diethyl ether was added to the solid colorless residue, and the suspension was stirred for 15 min. and then filtered out with suction. The less polar urea AA-15 was obtained in a yield of 92% (200 mg).

Example AA-16

2',3',4',9'-Tetrahydro-N,N-dimethyl-4-butyl-2'-methyl-spiro[cyclohexane-1,1'(1'H)-pyrido[3,4-b]indol]-4-amine, 2-hydroxy-1,2,3-propanetricarboxylate (1:1) (less polar diastereoisomer)

Water (0.04 ml) was added to the free base of the less polar spiroamine AA-9 (200 mg, 0.59 mmol), and the mixture was dissolved at 0° C. in 95% formic acid (0.6 ml, 732 mg, 15.9 mmol). At that temperature, 37% aqueous formaldehyde solution (0.46 ml, 178 mg, 5.9 mmol) was added, stirring was carried out for 10 min. in an ice bath, and the mixture was warmed for 1 h at 10° C. Water (5 ml) and 1N sodium hydroxide solution (15 ml) were added to the beige-colored solution, while cooling with ice. The cloudy mixture was stirred for 30 min. at room temperature; dichloromethane (20 ml) was added and stirring was carried out for a further 30 min. The phases were separated. The aqueous phase was extracted with dichloromethane (15 ml). The combined organic phases were washed with water (15 ml), dried and concentrated. The residue (225 mg) was a beige-colored oil which was separated by chromatography [silica gel 60 (40 g); ethyl acetate (250 ml)]. The spiroamine was obtained in the form of a colorless solid in a yield of 25% (51 mg).

The resulting less polar spiroamine (51 mg, 0.144 mmol) was dissolved at 60° C. in ethanol (2 ml), and an ethanolic solution (2 ml) of citric acid (64 mg, 0.316 mmol) was added. After a reaction time of 6 h, the citrate 5/6 was filtered out with suction in the form of a colorless solid and washed with ethanol (2×2 ml) and diethyl ether (2×5 ml). The less polar spiroamine was obtained in the form of the hygroscopic citrate AA-16 in a yield of 47% (37 mg).

Example AA-17

6'-Fluoro-4',9'-dihydro-N-ethyl-N-methyl-4-butyl-spiro[cyclohexane-1,1'(3'H)-pyrano[3,4-b]indol]-4-amine, 2-hydroxy-1,2,3-propanetricarboxylate (1:1) (one of two possible diastereoisomers)

Trifluoromethanesulfonic acid (450 mg, 265 µl, 3 mmol) was added, while cooling with ice, to a solution of E-7 (500 mg, 2 mmol) and 5-fluorotryptophol F-2 (430 mg, 2.4 mmol) in anhydrous dichloromethane (25 ml), and stirring was carried out overnight at room temperature. 0.5 N sodium hydroxide solution (10 ml) was then added to the reaction mixture, stirring was carried out for 2 h at room temperature, the organic phase was separated, and the aqueous phase was extracted with dichloromethane (2×20 ml). The combined organic phases were dried with sodium sulfate and concentrated in vacuo. The crude product was purified by means of flash chromatography (100 g, 20×4.0 cm) with cyclohexane/ethyl acetate (9:1) and 1% triethylamine.

Yield: 469 mg (53%), white solid
Melting point: 112-121° C.
$^1$H-NMR (DMSO-$d_6$): 0.89 (t, 3H, J=6.8 Hz); 1.13 (t, 3H, J=6.9 Hz); 1.18-1.33 (m, 4H); 1.51-1.58 (m, 4H); 1.65-1.73 (m, 2H); 1.65-1.73 (m, 2H); 2.04-2.13 (m, 2H); 2.22 (s, 3H); 2.40-2.48 (m, 2H); 2.62 (t, 2H, J=5.3 Hz); 3.88 (t, 2H, J=5.3 Hz); 6.80-6.88 (m, 1H); 7.11 (dd, 1H, J=9.8, 2.3 Hz); 7.31 (dd, 1H, J=8.8, 4.6 Hz); 10.67 (s, 1H).
$^{13}$C-NMR: 14.0; 14.9; 20.0; 22.1; 23.4; 26.6; 27.3 (2C); 29.9 (2C); 32.7; 42.5; 56.1; 58.6; 72.1; 102.3 (d, J=23 Hz); 105.4 (d, J=4 Hz); 108.2 (d, J=26 Hz); 111.9 (d, J=10 Hz); 126.1 (d, J=10 Hz); 132.4; 141.9; 156.7 (d, J=231).

Citric acid (232 mg, 1.21 mmol) in isopropanol (5 ml) was added to the prepared spiroether (366 mg, 0.98 mmol) in hot isopropanol (60 ml). The resulting precipitate AA-17 was filtered out and dried.

Yield: 203 mg (37%), white solid AA-17
Melting point: 206-209° C.
$^1$H-NMR (DMSO-$d_6$): 0.86 (t, 3H, J=6.9 Hz); 1.12-1.29 (m, 7H); 1.31-1.81 (m, 6H); 1.98-2.09 (m, 2H); 2.36 (s, 3H); 2.46-2.69 (m, 10H); 3.85 (t, 2H, J=5.4 Hz); 6.82 (dt, 1H, J=9.3, 2.6 Hz); 7.09 (dd, 1H, J=9.8, 2.4 Hz); 7.30 (dd, 1H, J=8.7, 4.6 Hz); 10.55 (s, 1H).

Example AA-18

6'-Fluoro-4',9'-dihydro-N-benzyl-N-methyl-4-butyl-spiro[cyclohexane-1,1'(3'H)-pyrano[3,4-b]indol]-4-amine (one of two possible diastereoisomers)

Trifluoromethanesulfonic acid (346 mg, 204 µl, 2.30 mmol) was added, while cooling with ice, to a solution of E-8 (500 mg, 1.73 mmol) and 2-(5-fluoro-1H-indol-3-yl)ethanol F-2 (311 mg, 1.73 mmol) in anhydrous dichloromethane (30 ml), and stirring was carried out overnight at room temperature. 0.5 M sodium hydroxide solution (17 ml) was then added to the reaction mixture and stirring was carried out for 1 h at room temperature. The phases were separated, the aqueous phase was extracted with dichloromethane (3×20 ml), and the combined organic phases were dried with sodium sulfate and concentrated in vacuo. The crude product (954 mg) was purified by means of flash chromatography (100 g, 20×3.6 cm) with cyclohexane/ethyl acetate (9:1).

Yield: 424 mg (56%), amorphous white solid AA-18
Melting point: 58-62° C.

$^1$H-NMR (DMSO-$d_6$): 0.97 (t, 3H, J=6.79 Hz); 1.38-1.49 (m, 6H); 1.77-1.87 (m, 4H); 1.88-1.96 (m, 4H); 2.10 (s, 3H); 2.63 (t, 2H, J=5.2 Hz); 3.62 (s, 2H); 3.89 (t, 2H, J=5.2 Hz); 6.87 (dt, 1H, J=9.1 and 2.5 Hz); 7.13 (dd, 2H, J=9.8 and 2.4 Hz); 7.24-7.35 (m, 5H); 11.03 (s, 1H).
$^{13}$C-NMR (DMSO-$d_6$): 14.3; 22.1; 23.1; 25.1; 25.4; 26.3; 30.4; 31.5; 34.1; 53.4; 56.5; 58.8; 71.7; 102.4 (d, J=23 Hz); 105.6 (d, J=5 Hz); 108.3 (d, J=26 Hz); 111.6 (d, J=11 Hz); 126.2; 126.6 (d, J=10 Hz); 127.8; 128.=; 132.2; 141.7; 141.9; 156.7 (d, J=231 Hz).

Example AA-19

6'-Fluoro-4',9'-dihydro-N-phenyl-4-butyl-spiro[cyclohexane-1,1'(3'H)-pyrano[3,4-b]indol]-4-amine (one of two possible diastereoisomers)

Trifluoromethanesulfonic acid (300 mg, 177 µl, 2.0 mmol) was added as quickly as possible, at 10° C., to a solution of E-11 (368 mg, 1.5 mmol) and 2-(5-fluoro-1H-indol-3-yl) ethanol F-2 (269 mg, 1.5 mmol) in anhydrous dichloromethane, and stirring was carried out overnight at room temperature. In order to monitor the conversion, a sample (0.5 ml) was removed and washed with 0.5 N sodium hydroxide solution, and the organic phase was dried with sodium sulfate. When the reaction was complete, 0.5 N sodium hydroxide solution (10 ml) was added to the reaction mixture, stirring was carried out for 2 h at room temperature, the organic phase was separated, the aqueous phase was extracted with dichloromethane (2×20 ml), and the combined organic phases were dried with sodium sulfate and concentrated in vacuo. The crude product was then purified by means of flash chromatography (18 g, 20×2.0 cm) with cyclohexane/ethyl acetate (9:1) and 1% triethylamine.

Yield: 327 mg (54%), white solid AA-19
Melting point: 150-162° C.
$^1$H-NMR (DMSO-$d_6$): 0.87 (t, 3H, J=6.9 Hz); 1.25-1.35 (m, 4H); 1.77-1.97 (m, 10H); 2.64 (t, 2H, J=5.2 Hz); 3.90 (t, 2H, J=5.3 Hz); 4.92 (s, 1H); 6.50 (t, 1H, J=7.1 Hz); 6.75 (d, 2H, J=7.9 Hz); 6.83-6.90 (m, 1H); 7.02 (t, 2H, J=7.8 Hz); 7.14 (dd, 1H, J=9.8, 2.5 Hz); 7.30 (dd, 1H, J=8.7, 4.6 Hz); 11.03 (s, 1H).
$^{13}$C-NMR: 14.2; 22.0; 22.7; 25.1; 30.7; 30.9; 31.1; 54.0; 58.8; 71.6; 102.5 (d, J=23 Hz); 105.6 (d, J=5 Hz); 108.3 (d, J=26 Hz); 111.6 (d, J=11 Hz); 115.2; 126.6 (d, J=10 Hz); 128.5; 132.2; 141.6; 147.5; 156.7 (d, J=237 Hz).

Example AA-20

4-Butyl-6'-fluoro-4-(N-morpholino)-1',3',4',9'-tetrahydrospiro[cyclohexane-1,1'-pyrano[3,4-b]indole] (less polar diastereoisomer)

Trifluoromethanesulfonic acid (400 mg, 236 µl, 2.66 mmol) was added dropwise, while cooling with ice-water, to a solution of E-12 (479 mg, 2 mmol) and 2-(5-fluoro-1H-indol-3-yl)ethanol F-2 (358 mg, 2 mmol) in dichloromethane (50 ml). The reaction mixture was stirred for 20 h at room temperature, then 0.5 M sodium hydroxide solution (20 ml) was added, followed by stirring for 3 h at room temperature. The organic phase was separated, the aqueous phase was extracted with dichloromethane (3×20 ml), and the combined organic phases were washed with sodium chloride solution (50 ml), dried with sodium sulfate and concentrated in vacuo.

The isomer mixture (815 mg) was separated by flash chromatography (100 g, 22×4 cm) with ethyl acetate/cyclohexane (1:3).

Fraction 1: non-polar diastereoisomer, AA-20
Yield: 259 mg (32%), white solid
Melting point: >250° C.
$^1$H-NMR (CDCl$_3$): 0.92 (t, 3H, J=6.5 Hz); 1.19-2.10 (m, 14H); 2.58-2.65 (m, 4H); 2.75 (t, 2H, J=5.3 Hz); 3.75-3.81 (m, 4H); 3.99 (t, 2H, J=5.4 Hz); 6.91 (dt, 1H, J=8.8, 1.8 Hz); 7.12 (dd, 1H, J=9.5, 2.5 Hz); 7.30-7.26 (m, 1H), 7.55 (s, 1H).
$^{13}$C-NMR (CDCl$_3$): 14.1; 22.5; 23.8; 26.7 (2C); 26.9; 30.3 (2C); 33.4; 45.1 (2C); 56.1; 59.6; 68.5 (2C); 72.3; 103.3 (d, J=23 Hz); 107.5 (d, J=4 Hz); 109.7 (d, J=26 Hz); 111.3 (d, J=10 Hz); 127.6 (d, J=10 Hz); 132.1; 141.2; 157.9 (d, J=235 Hz).

Fraction 2: more polar diastereoisomer, see Example AA-21
Yield: 335 mg (42%), white solid
Melting point: 238-241° C.
$^1$H-NMR (CDCl$_3$): 0.98 (t, 3H, J=6.4 Hz); 1.30-2.05 (m, 14H); 2.63-2.68 (m, 4H); 2.75 (t, 2H, J=5.3 Hz); 3.68-3.72 (m, 4H); 3.99 (t, 2H, J=5.4 Hz); 6.90 (dt, 1H, J=9.3, 2.4 Hz); 7.12 (dd, 1H, J=9.4, 2.0 Hz); 7.24 (dd, 1H, J=8.8, 4.3 Hz); 7.63 (s, 1H).
$^{13}$C-NMR (CDCl$_3$): 14.4; 22.4; 23.6; 25.3; 25.6 (2C); 30.7; 32.4 (2C); 45.7 (2C); 56.4; 59.6; 68.2 (2C); 71.9; 103.4 (d, J=24 Hz); 107.8; 109.8 (d, J=27 Hz); 111.3 (d, J=9 Hz); 127.5; 132.1; 140.7; 158.0 (d, J=234 Hz).

Example AA-21

4-Butyl-6'-fluoro-4-(N-morpholino)-1',3',4',9'-tetrahydrospiro[cyclohexane-1,1'-pyrano[3,4-b]indole] (more polar diastereoisomer)

The more polar diastereoisomer obtained in Example AA-20 is taken further as Example AA-21.
AA-21 (More Polar Diastereoisomer)
Yield: 335 mg (42%), white solid
Melting point: 238-241° C.
$^1$H-NMR (CDCl$_3$): 0.98 (t, 3H, J=6.4 Hz); 1.30-2.05 (m, 14H); 2.63-2.68 (m, 4H); 2.75 (t, 2H, J=5.3 Hz); 3.68-3.72 (m, 4H); 3.99 (t, 2H, J=5.4 Hz); 6.90 (dt, 1H, J=9.3, 2.4 Hz); 7.12 (dd, 1H, J=9.4, 2.0 Hz); 7.24 (dd, 1H, J=8.8, 4.3 Hz); 7.63 (s, 1H).
$^{13}$C-NMR (CDCl$_3$): 14.4; 22.4; 23.6; 25.3; 25.6 (2C); 30.7; 32.4 (2C); 45.7 (2C); 56.4; 59.6; 68.2 (2C); 71.9; 103.4 (d, J=24 Hz); 107.8; 109.8 (d, J=27 Hz); 111.3 (d, J=9 Hz); 127.5; 132.1; 140.7; 158.0 (d, J=234 Hz).

Example AA-22

4',9'-Dihydro-N,N-dimethyl-4-methoxypropyl-spiro[cyclohexane-1,1'(3'H)-pyrano[3,4-b]indol]-4-amine, 2-hydroxy-1,2,3-propanetricarboxylate (1:1) (one of two possible diastereoisomers)

The ketone E-4 (275 mg, 1.26 mmol) and tryptophol F-1 (206 mg, 1.26 mmol) were dissolved in abs. dichloromethane (10 ml); methanesulfonic acid (0.13 ml, 2.05 mmol) was added, under argon, and stirring was carried out for 20 h at room temperature. After addition of 1N NaOH (10 ml) and CH$_2$Cl$_2$ (20 ml), stirring was carried out for a further 10 min., the phases were separated, the aqueous phase was extracted twice with CH$_2$Cl$_2$, the combined organic phases were washed with water and dried over Na$_2$SO$_4$, and the solution was concentrated in vacuo. The residue that remained was purified by flash chromatography with CHCl$_3$/MeOH (20:1).
Yield: 327 mg (73%)
In the reaction with a molar amount of citric acid in ethanol, the citrate AA-22 precipitated in the form of a solid.
Yield: 281 mg (AA-22)
Melting point: 207-208° C.
$^1$H-NMR (DMSO-d$_6$): 1.35-1.56 (8H, m); 1.71 (2H; t); 2.14 (2H, t); 2.26 (6H, s); 2.64 (2H, t); 3.25 (3H, s); 3.36 (2H s); 3.89 (2H, t); 6.95 (2H, m); 7.32 (2H, m); 10.72 (1H, bs), free base.
$^{13}$C-NMR (DMSO-d$_6$): 22.13; 24.27; 25.80; 27.78; 29.26; 37.16; 44.12; 57.81; 59.09: 71.16; 72.18; 105.25; 111.38; 117.58; 118.35; 120.62; 126.36; 135.63; 138.96; 171.95; 177.09, citrate.

Example AA-23

6'-Fluoro-4',9'-dihydro-N,N-dimethyl-4-methoxypropyl-spiro[cyclohexane-1,1'(3'H)-pyrano[3,4-b]indol]-4-amine, 2-hydroxy-1,2,3-propanetricarboxylate (1:1) (less polar diastereoisomer)

The ketone E-4 (426 mg, 2 mmol) and 5-fluoro-tryptophol F-1 (362 mg, 2 mmol) were dissolved in abs. dichloromethane (10 ml); methanesulfonic acid (0.14 ml, 2.2 mmol) was added, under argon, and stirring was carried out for 24 h at room temperature. After addition of 1N NaOH (10 ml), the phases were separated, the aqueous phase was extracted with CH$_2$Cl$_2$ (3×10 ml), the combined organic phases were washed with water (10 ml) and dried over Na$_2$SO$_4$, and the solution was concentrated in vacuo. The residue that remained was purified by flash chromatography with CHCl$_3$/MeOH (20:1 pure methanol).
Yield: 408 mg (54%) less polar compound
218 mg (29%) more polar compound
In the reaction of the less polar compound with a molar amount of citric acid in ethanol, the citrate precipitated in the form of a colorless solid.
Yield: 384 mg, non-polar compound AA-23
Melting point: 210-213° C.
$^1$H-NMR (DMSO-d$_6$): 1.52 (4H, m); 1.70 (4H, m); 1.83 (2H; m); 2.14 (2H, m); 2.60-2.73 (12H, m); 3.25 (3H, s); 3.35 (2H m); 3.89 (2H, t); 6.83 (1H, m); 7.13 (1H, m); 7.36 (1H, m); 10.91 (1H, bs).

Example AA-24

2',3',4',9'-Tetrahydro-N,N-dimethyl-4-(3-methoxypropyl)-spiro[cyclohexane-1,1'(1'H)-pyrido[3,4-b]indol]-4-amine, 2-hydroxy-1,2,3-propanetricarboxylate (1:1) (less polar diastereoisomer)

The ketone E-4 (426 mg, 2 mmol) and tryptamine H-1 (320 mg, 2 mmol) were dissolved in abs. methanol (10 ml), and stirring was carried out for 20 h at room temperature. The solvent was then removed in vacuo, the residue was dissolved in DCE (20 ml), trifluoroacetic acid (2 ml) was added, and stirring was carried out for 5 h at room temperature. After addition of 1N NaOH (10 ml) and CH$_2$Cl$_2$ (10 ml), stirring was carried out for a further 20 min., the phases were separated, the aqueous phase was extracted with CH$_2$Cl$_2$ (2×10 ml), the combined organic phases were washed with water (10 ml) and dried over Na$_2$SO$_4$, and the solution was concentrated in vacuo. The residue that remained was purified by flash chromatography with CHCl$_3$/MeOH (9:1 without triethylamine ⇨ 4:1+1% triethylamine).

Yield: 350 mg (49%) less polar compound, contaminated with starting ketone 321 mg (45%) more polar compound, contaminated In the reaction of the non-polar compound with a molar amount of citric acid in ethanol, the citrate AA-24 precipitated in the form of a colorless solid.

Yield: 264 mg, non-polar diastereoisomer AA-24 (clean)

Melting point: 247-248° C.

$^1$H-NMR (DMSO-d$_6$): 1.44-1.55 (4H, m); 1.79 (6H; m); 2.33-2.63 (12H, m); 2.86 (2H, m); 3.25 (3H, s); 3.38 (4H m); 7.00 (1H, m); 7.07 (1H, m); 7.39 (2H, m); 11.04 (1H, bs).

Example AA-25

4',9'-Dihydro-N,N-dimethyl-4-(4-methoxybutyl)-spiro[cyclohexane-1,1'(3'H)-pyrano[3,4-b]indol]-4-amine, 2-hydroxy-1,2,3-propanetricarboxylate (1:1) (one of two possible diastereoisomers)

The ketone E-3 (455 mg, 2 mmol) and tryptophol F-1 (326 mg, 2 mmol) were dissolved in abs. dichloromethane (10 ml); methanesulfonic acid (0.14 ml, 2.2 mmol) was added, under argon, and stirring was carried out for 24 h at room temperature. After addition of 1N NaOH (15 ml) and CH$_2$Cl$_2$ (25 ml), stirring was carried out for a further 10 min., then the phases were separated, the aqueous phase was extracted twice with CH$_2$Cl$_2$ (10 ml), the combined organic phases were washed with water (10 ml) and dried over Na$_2$SO$_4$, and the solution was concentrated in vacuo. The residue that remained was purified by flash chromatography with CHCl$_3$/MeOH (20:1).

Yield: 687 mg (93%)

In the reaction with a molar amount of citric acid in ethanol, the citrate AA-25 precipitated in the form of a colorless solid.

Yield: 152 mg, white solid

Melting point: 214-215° C.

$^1$H-NMR (DMSO-d$_6$): 1.33 (2H, m); 1.51 (4H; m); 1.75 (4H, m) 1.95 (2H, t); 2.14 (2H, t); 2.66 (10H, m); 3.31 (3H, s); 3.36 (2H t); 3.90 (2H, s); 6.98 (2H, m); 7.38 (2H, m); 10.88 (1H, bs), citrate.

$^{13}$C-NMR (DMSO-d$_6$): 21.04; 22.16; 26.93; 29.90; 30.23; 30.91; 37.19; 55.17; 57.74; 58.75; 71.85; 104.91; 111.18; 117.41; 118.18; 120.33; 126.40; 135.81; 139.71, free base.

Example AA-26

6'-Fluoro-4',9'-dihydro-N,N-dimethyl-4-(4-methoxybutyl)-spiro[cyclohexane-1,1'(3'H)-pyrano[3,4-b]indol]-4-amine, 2-hydroxy-1,2,3-propanetricarboxylate (1:1) (more polar diastereoisomer)

The ketone E-3 (426 mg, 2 mmol) and 5-fluoro-tryptophol F-2 (362 mg, 2 mmol) were dissolved in abs. dichloromethane (10 ml); methanesulfonic acid (0.14 ml, 2.2 mmol) was added, under argon, and stirring was carried out for 24 h at room temperature. After addition of 1N NaOH (10 ml) reaction of the solution), the phases were separated, the aqueous phase was extracted with CH$_2$Cl$_2$ (3×10 ml), the combined organic phases were washed with water (10 ml) and dried over Na$_2$SO$_4$, and the solution was concentrated in vacuo. The residue that remained was separated by flash chromatography with CHCl$_3$/MeOH (20:1).

Yield: 613 mg (79%)

In the reaction with a molar amount of citric acid in ethanol, the citrate AA-26 precipitated in the form of a colorless solid.

Melting point: 216-218° C.

$^1$H-NMR (DMSO-d$_6$): 1.12 (2H, m); 1.50 (4H; m); 1.68 (4H, m) 1.86 (2H, t); 2.06 (2H, t); 2.56 (10H, m); 3.22 (3H, s); 3.34 (5H m); 3.87 (2H, s); 4.34 (1H, bs); 6.81 (1H, t); 7.11 (1H, m); 7.34 (1H, m); 10.81 (1H, bs), citrate.

$^{13}$C-NMR (DMSO-d$_6$): 21.04; 22.08; 26.88; 29.84; 30.23; 30.86; 37.10; 55.16; 57.74; 58.69; 71.84; 72.00; 102.16; 102.38; 105.37; 108.00; 111.89; 111.98; 126.65; 132.44; 141.91; 155.56; 157.85, free base.

Example AA-27

2',3',4',9'-Tetrahydro-N,N-dimethyl-4-(4-methoxybutyl)-spiro[cyclohexane-1,1'(1'H)-pyrido[3,4-b]indol]-4-amine, 2-hydroxy-1,2,3-propanetricarboxylate (1:1) (less polar diastereoisomer)

The ketone E-3 (455 mg, 2 mmol) and tryptamine H-1 (320 mg, 2 mmol) were dissolved in abs. methanol (10 ml) and stirring was carried out for 20 h at room temperature. The solvent was then removed in vacuo, the residue was dissolved in DCE (20 ml), trifluoroacetic acid (2 ml) was added, and stirring was carried out for 5 h at room temperature. After addition of 1N NaOH (10 ml) and CH$_2$Cl$_2$ (10 ml), stirring was carried out for a further 30 min., the phases were separated, the aqueous phase was extracted with CH$_2$Cl$_2$ (2×10 ml), the combined organic phases were washed with water (10 ml) and dried over Na$_2$SO$_4$, and the solution was concentrated in vacuo. The residue that remained was purified by flash chromatography with CHCl$_3$/MeOH (9:1 without triethylamine ~4:1+1% triethylamine).

Yield: 273 mg (37%), less polar compound 335 mg (48%), more polar compound, contaminated In the reaction of the non-polar diastereoisomer with a molar amount of citric acid in ethanol, the citrate AA-27 precipitated in the form of a colorless solid.

Yield: 204 mg, non-polar diastereoisomer AA-27

Melting point: 236-240° C.

$^1$H-NMR (DMSO-d$_6$): 1.40 (2H, m); 1.63 (4H, m); 1.80-2.08 (8H; m); 2.52-266 (10H, m); 3.12 (2H, t); 3.26 (3H s); 3.41 (2H, m); 6.94 (1H, m); 7.06 (1H, m); 7.37 (2H, m); 10.86 (1H, bs).

Example AA-28

4',9'-Dihydro-N,N-dimethyl-4-cyclopentyl-spiro[cyclohexane-1,1'(3'H)-pyrano-[3,4-b]indol]-4-amine, 2-hydroxy-1,2,3-propanetricarboxylate (2:1) (one of two possible diastereoisomers)

The ketone E-6 (235 mg, 1.1 mmol) and tryptophol F-1 (180 mg, 1.12 mmol) were dissolved in abs. dichloromethane (5 ml); methanesulfonic acid (0.1 ml, 1.5 mmol) was added, under argon, and stirring was carried out for 20 h at room temperature. After addition of 1N NaOH (5 ml) and CH$_2$Cl$_2$ (10 ml), stirring was carried out for a further 10 min., the phases were separated, the aqueous phase was extracted twice with CH$_2$Cl$_2$, the combined organic phases were washed with water and dried (Na$_2$SO$_4$), and the solution was concentrated in vacuo. The residue that remained was purified by flash chromatography with CHCl$_3$/MeOH (20:1).

Yield: 361 mg, substance mixture obtained, in the reaction with a molar amount of citric acid in ethanol, the citrate AA-28 precipitated in the form of a colorless solid.

Yield: 302 mg (50%), 1 diastereoisomer AA-28

Melting point: 200-202° C.

$^1$H-NMR (DMSO-d$_6$): 1.35 (6H, m); 1.61 (8H, m); 1.98 (3H, m); 2.36 (8H, m); 2.84 (1H, m); 2.59 (2H; s); 3.74 (2H, m); 6.83 (2H, m); 7.23 (2H, m); 10.63 (1H, s).

$^{13}$C-NMR (DMSO-d$_6$): 22.10; 23.87; 24.67; 28.15; 29.42; 38.26; 42.72; 43.46; 59.14; 71.29; 72.08; 105.32; 111.24; 117.64; 118.41; 120.71; 126.36; 135.51; 138.91; 171.40; 175.86.

Example AA-29

2',3',4',9'-Tetrahydro-N,N-dimethyl-4-cyclopentyl-spiro[cyclohexane-1,1'(1'H)-pyrido[3,4-b]indol]-4-amine, 2-hydroxy-1,2,3-propanetricarboxylate (1:1) (one of two possible diastereoisomers)

The ketone E-6 (209 mg, 1.0 mmol) and tryptamine H-1 (160 mg, 1.0 mmol) were dissolved in abs. methanol (10 ml) and stirred for 20 h at room temperature. Then the solvent was removed in vacuo, the residue was dissolved in dichloroethane (10 ml), trifluoroacetic acid (1.0 ml) was added, and stirring was carried out for 5 d at room temperature. After addition of 1N NaOH (10 ml) and CH$_2$Cl$_2$ (10 ml), stirring was carried out for a further 20 min., the phases were separated, the aqueous phase was extracted twice with CH$_2$Cl$_2$, the combined organic phases were washed with water and dried (Na$_2$SO$_4$), and the solution was concentrated in vacuo. The residue that remained was purified by flash chromatography with CHCl$_3$/MeOH (20:1). In the reaction with a molar amount of citric acid in ethanol, the citrate AA-29 precipitated in the form of a colorless solid.

Yield: 226 mg (64%) 1 diastereoisomer AA-29
Citrate: melting point: 229-230° C.
Because the NMR spectra of the citrate were poorly resolved, the NMR spectra of the free base have been given.
$^1$H-NMR (DMSO-d$_6$): 1.43 (12H, m); 1.80 (2H, t); 2.07 (3H, m); 2.35 (6H, s); 2.55 (2H, m); 3.00 (2H, t); 3.37 (1H, bs); 6.96 (2H, m); 7.30 (2H, m); 10.55 (1H, s).
$^{13}$C-NMR (DMSO-d$_6$): 22.53; 24.57; 24.81; 28.04; 30.72; 37.85; 38.66; 43.97; 52.07; 57.12; 106.26; 111.00; 117.20; 117.90; 120.09; 126.89; 135.59; 141.62.

Example AA-30

4',9'-Dihydro-N,N-dimethyl-4-cyclohexyl-spiro[cyclohexane-1,1'(3'H)-pyrano[3,4-b]indol]-4-amine, 2-hydroxy-1,2,3-propanetricarboxylate (2:1) (one of two possible diastereoisomers)

The ketone E-5 (175 mg, 0.78 mmol) and tryptophol F-1 (126 mg, 0.78 mmol) were dissolved in abs. dichloromethane (5 ml); methanesulfonic acid (0.07 ml, 1.1 mmol) was added, under argon, and stirring was carried out for 72 h at room temperature. After addition of 1N NaOH (5 ml) and CH$_2$Cl$_2$ (10 ml), stirring was carried out for a further 10 min., the phases were separated, the aqueous phase was extracted twice with CH$_2$Cl$_2$, the combined organic phases were washed with water and dried (Na$_2$SO$_4$), and the solution was concentrated in vacuo. The residue that remained was purified by flash chromatography with CHCl$_3$/MeOH (20:1). In the reaction with a molar amount of citric acid in ethanol, the citrate AA-30 precipitated in the form of a colorless solid.

Yield: 110 mg (39%) 1 diastereoisomer AA-30
Citrate: melting point: 230-231° C.
$^1$H-NMR (DMSO-d$_6$): 1.10 (6H, m); 1.77 (12H, m); 2.07 (2H, m); 2.66 (10H; m); 3.88 (2H, m); 6.97 (2H, m); 7.36 (2H, m); 10.72 (1H, s).
$^{13}$C-NMR (DMSO-d$_6$): 22.16; 24.64; 26.00; 28.77; 30.09; 43.01; 43.62; 59.01; 71.52; 72.16; 105.20; 111.24; 117.59; 118.35; 120.61; 126.43; 135.64; 139.26; 171.56; 176.14.

Example AA-31

6'-Fluoro-4',9'-dihydro-N,N-dimethyl-4-cyclohexyl-spiro[cyclohexane-1,1'(3'H)-pyrano[3,4-b]indol]-4-amine, 2-hydroxy-1,2,3-propanetricarboxylate (1:1) (one of two possible diastereoisomers)

The ketone E-5 (137 mg, 0.61 mmol) and 5-fluoro-tryptophol F-2 (109 mg, 0.61 mmol) were dissolved in abs. dichloromethane (4 ml); methanesulfonic acid (0.065 ml, 1.0 mmol) was added, under argon, and stirring was carried out for 48 h at room temperature. After addition of 1N NaOH (5 ml) and CH$_2$Cl$_2$ (10 ml), stirring was carried out for a further 20 min., the phases were separated, the aqueous phase was extracted twice with CH$_2$Cl$_2$, the combined organic phases were washed with water and dried (Na$_2$SO$_4$), and the solution was concentrated in vacuo. The residue that remained was purified by flash chromatography with CHCl$_3$/MeOH (20:1). In the reaction with a molar amount of citric acid in ethanol, the citrate AA-31 precipitated in the form of a colorless solid.

Yield: 172 mg (73%), 1 diastereoisomer AA-31
Citrate: melting point: 204-205° C.
$^1$H-NMR (DMSO-d$_6$): 1.11 (6H, m); 1.43 (2H, m); 1.56 (4H, m); 1.77 (6H, m); 2.06 (2H, m); 2.57 (7H; m); 3.00 (2H, m); 6.90 (1H, m); 6.98 (1H, m); 7.30 (2H, m); 10.51 (1H, s).
$^{13}$C-NMR (DMSO-d$_6$): 22.04; 24.57; 25.97; 26.58; 28.72; 30.04; 38.38; 43.25; 58.93; 71.52; 72.11; 102.35; 102.58; 105.64; 108.52; 112.03; 126.56; 132.21; 171.32; 175.49.

Example AA-32

2',3',4',9'-Tetrahydro-N,N-dimethyl-4-cyclohexyl-spiro[cyclohexane-1,1'(1'H)-pyrido[3,4-b]indol]-4-amine, 2-hydroxy-1,2,3-propanetricarboxylate (1:1) (one of two possible diastereoisomers)

The ketone E-5 (175 mg, 0.78 mmol) and tryptamine H-1 (125 mg, 0.78 mmol) were dissolved in abs. methanol (8 ml) and stirred for 20 h at room temperature. Then the solvent was removed in vacuo, the residue was dissolved in dichloroethane (10 ml), trifluoroacetic acid (0.8 ml) was added, and stirring was carried out for 4 h at room temperature. After addition of 1N NaOH (5 ml) and CH$_2$Cl$_2$ (10 ml), stirring was carried out for a further 20 min., the phases were separated, the aqueous phase was extracted twice with CH$_2$Cl$_2$, the combined organic phases were washed with water and dried (Na$_2$SO$_4$), and the solution was concentrated in vacuo. The residue that remained was purified by flash chromatography with CHCl$_3$/MeOH (9:1).

Yield: 160 mg (56%) 1 diastereoisomer
Citrate: melting point: 228-229° C.
NMR spectra of the free base:
$^1$H-NMR (DMSO-d$_6$): 1.13 (6H, m); 1.72 (10H, m); 1.97 (2H, m); 2.59 (10H; m); 3.88 (2H, m); 6.86 (1H, t); 7.14 (1H, m); 7.32 (1H, m); 10.74 (1H, s).
$^{13}$C-NMR (DMSO-d$_6$): 22.58; 25.06; 26.32; 26.81; 28.85; 31.26; 38.22; 45.32; 51.91; 57.69; 72.11; 106.30; 110.97; 117.22; 117.91; 120.10; 126.94; 135.58; 141.69
The resulting spiroether (140 mg, 0.38 mmol) was dissolved in hot ethanol (4 ml), and a solution of citric acid (73 mg, 0.38 mmol) in ethanol (2 ml) was added. After standing for 2 hours in a refrigerator, the resulting solid AA-32 was filtered out with suction and dried in vacuo.

Yield: 160 mg (75%) (AA-32)
Melting point: 228-229° C.

Example AA-33

2',3',4',9'-Tetrahydro-N,N-dimethyl-4-butyl-spiro[cyclohexane-1,1'(1'H)-pyrido-[3,4-b]indol]-4-amine, 2-hydroxy-1,2,3-propanetricarboxylate (1:1) (more polar diastereoisomer)

The more polar spiroether prepared in Example AA-9 (90 mg, 0.26 mmol) was dissolved in hot ethanol (5 ml). Citric acid (48 mg, 0.26 mmol) dissolved in hot ethanol was added. The mixture was cooled to room temperature, whereupon a white precipitate formed. The precipitate was filtered out and dried in vacuo.

Yield: 89 mg (75%) (AA-33)

Example AA-34

6'-Fluoro-4',9'-dihydro-N,N-dimethyl-4-ethyl-spiro[cyclohexane-1,1'(3'H)-pyrano[3,4-b]indol]-4-amine, 2-hydroxy-1,2,3-propanetricarboxylate (1:1) (more polar diastereoisomer)

The free base of the polar spiroether from Example AA-2 (142 mg, 0.429 mmol) was dissolved in hot ethanol (5 ml), and citric acid (78 mg, 0.429 mmol) dissolved in hot ethanol was added. The mixture was cooled to room temperature and concentrated in vacuo.

Yield: 212 mg (11%) (AA-34)

Melting point: 72-75° C.

$^1$H-NMR (DMSO-$d_6$): 1.05 (3H, t); 1.64 (2H, m); 1.94 (6H, m); 2.48 (2H, m); 2.55 (6H, s); 3.89 (2H, t); 6.87 (1H, m); 7.14 (1H, m); 7.29 (1H, m); 11.04 (1H, s).

Example AA-35

2',3',4',9'-Tetrahydro-N,N-dimethyl-4-(3-methoxypropyl)-spiro[cyclohexane-1,1'(1'H)-pyrido[3,4-b]indol]-4-amine, 2-hydroxy-1,2,3-propanetricarboxylate (1:1) (more polar diastereoisomer, purity <95%)

The ketone E-4 (426 mg, 2 mmol) and tryptamine H-1 (320 mg, 2 mmol) were dissolved in abs. methanol (10 ml) and stirred for 20 h at room temperature. Then the solvent was removed in vacuo, the residue was dissolved in DCE (20 ml), trifluoroacetic acid (2 ml) was added, and stirring was carried out for 5 h at room temperature. After addition of 1N NaOH (10 ml) and CH$_2$Cl$_2$ (10 ml), stirring was carried out for a further 20 min., the phases were separated, the aqueous phase was extracted with CH$_2$Cl$_2$ (2×10 ml), the combined organic phases were washed with water (10 ml) and dried over Na$_2$SO$_4$, and the solution was concentrated in vacuo. The residue that remained was purified by flash chromatography with CHCl$_3$/MeOH (9:1 without triethylamine ⇒ 4:1+1% triethylamine).

Yield: 350 mg (49%) less polar compound, contaminated with starting ketone 321 mg (45%) polar compound, contaminated In the reaction of the polar compound with a molar amount of citric acid in ethanol, the citrate AA-35 precipitated in the form of a colorless solid.

Yield: 267 mg, polar diastereoisomer AA-35

Melting point: 228-229° C.

$^1$H-NMR (DMSO-$d_6$): 1.65 (4H, m); 1.88 (4H; m); 2.05 (4H, m); 2.47-2.59 (10H, m); 2.69 (2H, t); 3.18 (2H, t); 3.30 (3H s); 3.43 (2H, m); 6.97 (1H, m); 7.07 (1H, m); 7.33 (2H, m); 10.95 (1H, bs).

Example AA-36

6'-Fluoro-4',9'-dihydro-N,N-dimethyl-4-methoxypropyl-spiro[cyclohexane-1,1'(3'H)-pyrano[3,4-b]indol]-4-amine, 2-hydroxy-1,2,3-propanetricarboxylate (1:1) (more polar diastereoisomer)

The ketone E-4 (426 mg, 2 mmol) and 5-fluoro-tryptophol F-2 (362 mg, 2 mmol) were dissolved in abs. dichloromethane (10 ml); methanesulfonic acid (0.14 ml, 2.2 mmol) was added, under argon, and stirring was carried out for 24 h at room temperature. After addition of 1N NaOH (10 ml), the phases were separated, the aqueous phase was extracted with CH$_2$Cl$_2$ (3×10 ml), the combined organic phases were washed with water (10 ml) and dried over Na$_2$SO$_4$, and the solution was concentrated in vacuo. The residue that remained was separated by flash chromatography with CHCl$_3$/MeOH (20:1 ⇒ pure methanol).

Yield: 408 mg (54%) less polar compound 218 mg (29%) polar compound

In the reaction of the polar compound with a molar amount of citric acid in ethanol, no precipitate formed; the solution was therefore concentrated and a white, amorphous solid AA-36 was obtained.

Yield: 239 mg, polar compound, AA-36

$^1$H-NMR (DMSO-$d_6$): 1.65 (4H, m); 1.97 (8H; m); 2.56-2.68 (12H, m); 3.31 (3H, s); 3.45 (2H m); 3.89 (2H, t); 6.88 (1H, m); 7.17 (1H, m); 7.32 (1H, m); 11.06 (1H, bs).

Example AA-37

2',3',4',9'-Tetrahydro-N,N-dimethyl-4-butyl-2'-ethylaminocarbonyl-spiro[cyclohexane-1,1'(1'H)-pyrido[3,4-b]indol]-4-amine (more polar diastereoisomer)

The more polar spiroamine (free base from AA-9, 133 mg, 0.39 mmol) was suspended in abs. acetonitrile (30 ml), and ethyl isocyanate (0.034 ml, 31 mg, 0.43 mmol) was added. The reaction mixture was heated for 1.5 h at reflux. After cooling to room temperature, a colorless solid crystallised out. After filtration with suction, the more polar urea AA-37 was obtained in a yield of 46% (74 mg) with a melting point of 182-184° C.

Example AA-38

4',9'-Dihydro-N,N-dimethyl-4-butyl-spiro[cyclohexane-1,1'(3'H)-pyrano[3,4-b]-indol]-4-amine, 2-hydroxy-1,2,3-propanetricarboxylate (1:1) (more polar diastereoisomer)

Ketone E-2 (2.0 g/10.15 mmol) and tryptophol F-1 (1.63 g/10.15 mmol) were placed in abs. dichloromethane (70 ml), under argon, and then methanesulfonic acid (720 µl/11.16 mmol) was added. The mixture was stirred for 24 h at room temperature. For working up, 1N NaOH was added to the mixture and extraction with dichloromethane (3×15 ml) was carried out. The organic phase was dried over Na$_2$SO$_4$ and concentrated in vacuo. The residue was purified by flash chromatography with CHCl$_3$/MeOH (9:1, 1:1).

Yield: Fraction 1: Less polar diastereoisomer 2.18 g (contaminated with tryptophol)

Fraction 2: More polar diastereoisomer 862 mg (25%)

Fraction 2 (862 mg, 2.52 mmol) was dissolved in hot ethanol (5 ml). Citric acid (480 mg, 2.52 mmol) dissolved in hot ethanol was added. The mixture was cooled to room temperature, whereupon a white precipitate formed. The precipitate AA-38 was filtered out and dried in vacuo.

Yield: 476 mg (35%), polar AA-38

Example AA-39

2',3',4',9'-Tetrahydro-N,N-dimethyl-4-(4-methoxybutyl)-spiro[cyclohexane-1,1'(1'H)-pyrido[3,4-b]indol]-4-amine, 2-hydroxy-1,2,3-propanetricarboxylate (1:1) (more polar diastereoisomer)

The ketone E-3 (455 mg, 2 mmol) and tryptamine H-1 (320 mg, 2 mmol) were dissolved in abs. methanol (10 ml) and stirred for 20 h at room temperature. Then the solvent was removed in vacuo, the residue was dissolved in DCE (20 ml), trifluoroacetic acid (2 ml) was added, and stirring was carried out for 5 h at room temperature. After addition of 1N NaOH (10 ml) and $CH_2Cl_2$ (10 ml), stirring was carried out for a further 30 min., the phases were separated, the aqueous phase was extracted with $CH_2Cl_2$ (2×10 ml), the combined organic phases were washed with water (10 ml) and dried over $Na_2SO_4$, and the solution was concentrated in vacuo. The residue that remained was purified by flash chromatography with $CHCl_3$/MeOH (9:1 without triethylamine r 4:1+1% triethylamine).

Yield: 273 mg (37%), less polar compound 335 mg (48%), polar compound, contaminated In the reaction of the polar diastereoisomer with a molar amount of citric acid in ethanol, the citrate AA-39 precipitated in the form of a colorless solid.

Yield: 223 mg, polar diastereoisomer AA-39

Melting point: 202-204° C.

$^1$H-NMR (DMSO-$d_6$): 1.41 (4H, m); 1.53 (2H, m); 1.73 (6H; m); 2.31-2.61 (10H, m); 2.84 (2H, m); 3.35 (7H, m); 7.01 (1H, m); 7.09 (1H, m); 7.41 (2H, m); 10.95 (1H, bs).

Example AA-40

6'-Fluoro-4',9'-dihydro-N-benzyl-4-allyl-spiro[cyclohexane-1,1'(3'H)-pyrano-[3,4-b]indol]-4-amine, 2-hydroxy-1,2,3-propanetricarboxylate (2:1) (one of two possible diastereoisomers)

Trifluoromethanesulfonic acid (328 mg, 556 µl, 2.18 mmol) was added at room temperature to a solution of E-13 (398 mg, 1.64 mmol) and 2-(5-fluoro-1H-indol-3-yl)ethanol F-2 (293 mg, 1.64 mmol) in absolute dichloromethane (20 ml), and stirring was carried out for 16 h at room temperature. 0.5 M sodium hydroxide solution (10 ml) was then added to the reaction solution, and stirring was carried out for 2 h at room temperature. The phases were separated and the aqueous phase was extracted with dichloromethane (3×30 ml). The combined organic phases were dried with sodium sulfate and concentrated in vacuo.

Yield: 649 mg (98%), slightly yellowish solid

Melting point: 45-48° C.

$^1$H-NMR (300 MHz, $d_6$-DMSO): 1.49-1.73 (m, 6H); 1.84 (t, J=6.8 Hz, 1H); 2.08 (dd, J=15.5, 11.7 Hz, 2H); 2.21 (d, J=7.0 Hz, 2H); 2.63 (t, J=5.3 Hz, 2H); 3.67 (d, J=6.4 Hz, 2H); 3.88 (t, J=5.2 Hz, 2H); 4.95-5.16 (m, 2H); 5.94 (m, 1H); 6.79-6.90 (m, 1H); 7.13 (dd, J=9.9, 2.5 Hz, 1H); 7.19-7.41 (m, 4H); 7.49 (d, J=7.0 Hz, 2H); 10.86 (s, 1H).

$^{13}$C-NMR (100 MHz, $d_6$-DMSO): 22.1; 29.3; 29.7; 38.9; 43.7; 45.1; 52.4; 58.8; 71.8; 102.4 (d, J=23 Hz); 105.4; 108.2 (d, J 26 Hz); 111.7; 116.8; 126.4; 126.7; 127.9; 128.1; 132.1; 135.1; 141.8; 142.0; 156.4 (d, J=231 Hz).

A solution of citric acid (142 mg, 0.74 mmol) in isopropanol (1.2 ml) was added at 70° C. to one of the resulting spiroethers (300 mg, 0.74 mmol) in isopropanol. The product precipitated at a low temperature in the form of the hemicitrate AA-40.

Yield: 389 mg (100%), colorless crystals AA-40

Melting point: 133° C.

$^1$H-NMR (300 MHz, $d_6$-DMSO): 1.58-1.80 (m, 6H); 1.96-2.18 (m, 2H); 2.32 (d, J=7.2 Hz, 2H); 2.57 (d, J=15.2 Hz, 1H); 2.65 (dd, J=12.8, 9.5 Hz, 3H); 3.84 (s, 2H); 3.88 (t, J=5.2 Hz, 2H); 4.34 (s, 1H); 5.09-5.21 (m, 2H); 5.95 (tdd, J=17.3, 10.0, 7.2 Hz, 1H); 6.80-6.92 (m, 1H); 7.14 (dd, J=9.9, 2.5 Hz, 1H); 7.24-7.45 (m, 4H); 7.49-7.57 (m, 2H); 10.72 (s, 1H).

$^{13}$C-NMR (100 MHz, $d_6$-DMSO): 22.0; 28.6; 29.5; 38.8; 42.9; 43.5; 45.0; 54.5; 58.9; 71.5; 71.8; 102.4 (d, J=23 Hz); 105.6; 108.3 (d, J=23 Hz); 111.8; 117.8; 126.7; 127.0; 128.2; 128.8; 132.0; 134.2; 141.7; 156.3 (d, J=231 Hz); 171.3; 175.8.

Example AA-41

6'-Fluoro-4',9'-dihydro-N-phenyl-4-allyl-spiro[cyclohexane-1,1'(3'H)-pyrano-[3,4-b]indol]-4-amine (one of two possible diastereoisomers)

Trifluoromethanesulfonic acid (342 mg, 580 µl, 2.28 mmol) was added at room temperature to a solution of E-10 (277 mg, 1.14 mmol) and 2-(5-fluoro-1H-indol-3-yl)ethanol F-2 (170 mg, 1.14 mmol) in absolute dichloromethane (20 ml), and stirring was carried out for 16 h at room temperature. 0.5 M sodium hydroxide solution (10 ml) was then added to the reaction solution, and stirring was carried out for 2 h at room temperature. The phases were separated and the aqueous phase was extracted with dichloromethane (3×30 ml). The combined organic phases were dried with sodium sulfate and concentrated in vacuo, and the residue was purified by flash chromatography (200 g, 20×5.6 cm) with cyclohexane/ethyl acetate (5:1→3:2).

AA-41:

Yield: 296 mg (66%), colorless solid

Melting point: 52-54° C.

$^1$H-NMR (300 MHz, $d_6$-DMSO): 1.60-2.14 (m, 8H); 2.64 (t, J=5.1 Hz, 2H); 2.77 (d, J=6.8 Hz, 2H); 3.90 (t, J=5.1 Hz, 2H); 4.98 (s, 1H); 5.11 (dd, J=13.7, 2.6 Hz, 2H); 5.73-5.91 (m, 1H); 6.53 (t, J=7.2 Hz, 1H); 6.80 (d, J=7.7 Hz, 2H); 6.87 (dd, J=9.6, 2.6 Hz, 1H); 7.04 (t, J=7.9 Hz, 2H); 7.15 (dd, J=9.9, 2.6 Hz, 1H); 7.30 (dd, J=8.7 Hz, 1H); 11.06 (s, 1H).

$^{13}$C-NMR (100 MHz, $d_6$-DMSO): 22.0; 30.4; 30.9; 35.4; 54.0; 58.9; 71.4; 102.5 (d, J=23 Hz); 105.6; 108.3 (d, J=26 Hz); 111.6; 115.5; 115.9; 117.1; 126.6; 128.5; 132.1; 135.1; 141.5; 147.1; 155.7 (d, J=230 Hz).

Example AA-42

6'-Fluoro-4',9'-dihydro-N-(4-methoxybenzyl)-4-allyl-spiro[cyclohexane-1,1'(3'H)-pyrano[3,4-b]indol]-4-amine (one of two possible diastereoisomers)

Trifluoromethanesulfonic acid (600 mg, 4.0 mmol) was added at room temperature to a solution of E-9 (843 mg, 3.08 mmol) and 2-(5-fluoro-1H-indol-3-yl)ethanol F-2 (552 mg, 3.08 mmol) in absolute dichloromethane (30 ml), and stirring was carried out for 72 h at room temperature. Further trifluoromethanesulfonic acid (300 mg, 2.0 mmol) was then added, and stirring was carried out again for 16 h. 0.5 M sodium hydroxide solution (10 ml) was then added to the reaction solution, and stirring was carried out for 2 h at room temperature. The phases were separated and the aqueous phase was extracted with dichloromethane (3×30 ml). The combined organic phases were dried with sodium sulfate and concentrated in vacuo.

Yield: 1.32 g (99%), yellowish solid AA-42
Melting point: 54-56° C.
$^1$H-NMR (400 MHz, d$_6$-DMSO): 1.50 (d, J=11.9 Hz, 2H); 1.72 (m, 4H); 1.91 (d, J=14.4 Hz, 2H); 2.55 (d, J=5.0 Hz, 2H); 2.64 (t, J=5.0 Hz, 2H); 3.63 (d, J=2.9 Hz, 2H); 3.72 (s, 3H); 3.88 (dd, J=5.2, 4.8 Hz, 2H); 5.18 (m, 3H); 5.88-6.04 (m, 1H); 6.80-6.93 (m, 4H); 7.08-7.17 (m, 1H); 7.27 (m, 2H); 11.01 (s, 1H).
$^{13}$C-NMR (100 MHz, d$_6$-DMSO): 22.0; 30.4; 31.1; 35.3; 44.1; 53.2; 54.9; 58.8; 71.8; 102.4 (d, J=23 Hz); 105.6; 108.2 (d, J=25 Hz); 108.5; 111.6; 113.4; 116.9; 126.6; 129.1; 132.1; 133.9; 135.5; 141.7; 156.3 (d, J=233 Hz).

Example AA-43

N-{6'-Fluoro-4',9'-dihydro-4-butyl-spiro[cyclohexane-1,1'(3'H)-pyrano[3,4-b]-indol]-4-yl}-pyrrolidine, 2-hydroxy-1,2,3-propanetricarboxylate (1:1) (one of two possible diastereoisomers)

Trifluoromethanesulfonic acid (949 mg, 552 µl, 6.3 mmol) was added, under argon and while cooling with ice, to a solution of E-14 (1.06 g, 4.7 mmol) and 2-(5-fluoro-1H-indol-3-yl)ethanol F-2 (854 mg, 4.7 mmol) in anhydrous dichloromethane (60 ml), and stirring was carried out for 1 d at room temperature. Further trifluoromethanesulfonic acid (300 mg, 173 µl, 2.0 mmol) was then added, and stirring was carried out again for 1 d at room temperature. 0.5 M sodium hydroxide solution (48 ml) was then added to the reaction mixture, and stirring was carried out for 20 min. The phases were separated, the aqueous phase was extracted with dichloromethane (2×20 ml), and the combined organic phases were dried with sodium sulfate The crude product (1.8 g) was purified by flash chromatography (180 g, 20×5.6 cm) with chloroform/methanol (95:5).

: 370 mg (19%), yellowish solid (fraction 1)

The product was present in the form of the hydrochloride. The hydrogen chloride presumably comes from the chloroform used for chromatography.

$^1$H-NMR (CDCl$_3$): 0.97 (t, 3H, J=6.8 Hz), 1.35-1.41 (m, 4H); 1.46-1.52 (m, 2H); 1.57 (d, 2H, J=14.6 Hz), 1.89-1.98 (m, 4H); 2.22 (dt, 2H, J=14.6, 6.0 Hz), 2.35-2.45 (m, 2H); 2.72 (t, 2H, J=5.3 Hz), 2.78 (dt, 2H, J=14.6, 3.5 Hz); 3.10 (dt, 2H, J=13.0, 6.9 Hz), 3.63 (dt, 2H, J=12.2 and 6.6 Hz), 3.92 (t, 2H, J=5.3 Hz), 6.81 (dt, 1H, J=9.2 and 2.5 Hz), 7.06 (dd, 1H, J=9.7, 2.4 Hz), 7.37 (dd, 1H, J=8.8, 4.5 Hz); 10.36 (br s, 1H); 11.04 (s, 1H).
$^{13}$C-NMR (CDCl$_3$): 13.9; 22.6; 23.4; 25.1; 26.6; 27.0; 29.5; 32.6; 48.2; 60.3; 66.5; 71.0; 102.4 (d, J=23 Hz); 106.1 (d, J=4 Hz); 109.2 (d, J=10 Hz); 112.4 (d, J=10 Hz); 126.3 (d, J=10 Hz); 132.4; 139.8; 157.5 (d, J=233 Hz).

In addition, contaminated product (fraction 2, 322 mg, 17%) and unreacted ketone (fraction 3, 227 mg, 23%) were also obtained.

The $^1$H-NMR spectrum of the crude product mixture showed that only one diastereoisomer and the alkene had formed, but the latter was not isolated.

A solution of fraction 1 (350 mg, 0.83 mmol) in chloroform (20 ml) was washed with sodium hydrogen carbonate solution, and the organic phase was dried with sodium sulfate and concentrated in vacuo.

Yield: 204 mg (70%), amorphous yellowish solid
Melting point: 70° C.
$^1$H-NMR (CDCl$_3$): 0.93 (t, 3H, J=6.7 Hz), 1.21-1.38 (m, 4H); 1.38-1.42 (m, 2H); 1.48 (d, 2H, J=12.8 Hz); 1.74 (d, 2H, J=12.8 Hz); 1.74-1.84 (m, 4H); 1.88 (dt, 2H, J=13.5, 2.9 Hz); 2.04 (dt, 2H, J=13.2, 3.2 Hz); 2.69 (t, 4H, J=5.8 Hz); 2.74 (t, 2H, J=5.4 Hz); 3.99 (t, 2H, J=5.4 Hz); 6.87 (dt, 1H, J=9.1, 2.5 Hz); 7.11 (dd, 1H, J=9.5, 2.4 Hz); 7.23 (dd, 1H, J=8.7, 4.3 Hz); 7.90 (s, 1H).
$^{13}$C-NMR (CDCl$_3$): 14.2; 22.5; 24.0; 24.1; 24.8; 27.0; 28.6; 30.8; 31.1; 44.1; 54.7; 59.7; 72.4; 103.2 (d, J=24 Hz); 107.1 (d, J=5 Hz); 109.4 (d, J=26 Hz); 111.2 (d, J=10 Hz); 127.6 (d, J=10 Hz); 132.0; 141.7; 157.8 (d, J=234 Hz).

A hot solution of citric acid (90 mg, 0.46 mmol) in ethanol (1.2 ml) was added to a solution of the yellow solid just obtained (free base of fraction 1) (180 mg, 0.46 mmol) in hot ethanol (15 ml). A white precipitate formed, which was filtered out after cooling.

: 137 mg (50%), white solid (AA-43)
Melting point: 198-199° C.
$^1$H-NMR (DMSO-d$_6$): 0.92 (t, 3H, J=6.7 Hz); 1.20-1.40 (m, 4H); 1.44-1.64 (m, 4H); 1.71 (br d, 2H, J=12.7 Hz); 1.90 (br s, 6H); 2.12 (br t, 2H, J=12.7 Hz); 2.57 (d, 2H, J=15.0 Hz); 2.63 (t, 2H, J=4 Hz); 2.66 (d, 2H, J=15.0 Hz); 3.07 (br s, 4H); 3.89 (t, 2H, J=5.1 Hz); 6.87 (dt, 1H, J=9.1, 2.4 Hz); 7.15 (dd, 1H, J=9.9, 2.3 Hz); 7.37 (dd, 1H, J=8.5, 4.4 Hz); 10.64 (s, 1H); ca. 11-12 (very br s, 2-3H).

Example AA-44

N-{6'-Fluoro-4',9'-dihydro-4-butyl-spiro[cyclohexane-1,1'(3'H)-pyrano[3,4-b]-indol]-4-yl}-piperidine (less polar diastereoisomer)

Trifluoromethanesulfonic acid (702 mg, 408 µl, 4.68 mmol) was added dropwise, while cooling with ice-water, to a solution of E-15 (860 mg, 3.6 mmol) and 2-(5-fluoro-1H-indol-3-yl)ethanol F-2 (645 mg, 3.6 mmol) in dichloromethane (70 ml). The reaction mixture was stirred for 20 h at room temperature, then 0.5 M sodium hydroxide solution (36 ml) was added and stirring was carried out for 2.5 h at room temperature. The organic phase was separated, and the aqueous phase was extracted with dichloromethane (3×20 ml). The combined organic phases were washed with sodium chloride solution (40 ml), dried with sodium sulfate and concentrated in vacuo. The isomer mixture (1.4 g) was separated by flash chromatography (140 g, 23×5.4 cm) with ethyl acetate/cyclohexane (1:3→1:2) and then with ethyl acetate.

Fraction 1 (non-polar diastereoisomer)
Yield: 98 mg (7%), white solid
Melting point: 126-130° C.
$^1$H-NMR (CDCl$_3$): 0.92 (t, 3H, J=6.8 Hz); 1.20-1.83 (m, 18H); 1.99-2.10 (m, 2H); 2.56 (m, 4H); 2.74 (t, 2H, J=5.4 Hz); 3.99 (t, 2H, J=5.4 Hz); 6.89 (dt, 1H, J=9.0, 2.5 Hz); 7.11 (dd, 1H, J=9.5, 2.5 Hz); 7.29-7.25 (m, 1H); 7.62 (s, 1H).
$^{13}$C-NMR (CDCl$_3$): 14.2; 22.5; 23.9; 25.4; 27.0; 27.6 (2); 28.0 (2); 30.5 (2); 33.6; 45.7; 56.4; 59.6; 72.6; 103.2 (d, J=23 Hz); 107.3 (d, J=4 Hz); 109.5 (d, J=26 Hz); 111.3 (d, J=10 Hz); 127.6 (d, J=10 Hz); 132.0; 141.6; 157.9 (d, J=234 Hz).

Fraction 2 (polar diastereoisomer)
Yield: 360 mg (25%), colorless oil
$^1$H-NMR (CDCl$_3$): 0.97 (t, 3H, J=6.4 Hz); 1.29-1.80 (m, 18H); 2.63-2.68 (m, 4H); 1.99 (t, 2H, J=11.2 Hz); 2.54-2.63

(m, 4H); 2.74 (t, 2H, J=5.4 Hz); 3.99 (t, 2H, J=5.4 Hz); 6.89 (dt, 1H, J=9.0, 2.4 Hz); 7.12 (dd, 1H, J=9.4, 2.2 Hz); 7.21-7.25 (m, 1H); 7.63 (s, 1H).

Example AA-45

N-{6'-Fluoro-4',9'-dihydro-4-butyl-spiro[cyclohexane-1,1'(3'H)-pyrano[3,4-b]-indol]-4-yl}-piperidine, 2-hydroxy-1,2,3-propanetricarboxylate (1:1) (more polar diastereoisomer)

A 0.5 M solution of citric acid in 2-propanol (1.38 ml, 0.69 mmol) was added to a hot solution of the more polar diastereoisomer prepared in Example AA-44 (fraction 2, 220 mg, 0.55 mmol) in 2-propanol (25 ml). The resulting precipitate was filtered out and dried in vacuo.

Yield: 160 mg (49%), white solid (AA-45)
Melting point: 236-238° C.
$^1$H-NMR (DMSO-$d_6$): 0.98 (t, 3H, J=6.9 Hz); 1.21-2.06 (m, 20H); 2.56 (d, 2H, J=15.1 Hz); 2.47 (d, 2H, J=15.1 Hz); 2.65 (t, 2H, J=5.1 Hz), 2.90 (br s, 4H), 3.90 (t, 2H, J=5.1 Hz, 2H), 6.89 (ddd, 1H, J=9.6, 8.9, 2.6 Hz); 7.16 (dd, 1H, J=9.9, 2.5 Hz); 7.29-7.35 (m, 1H); 11.03 (s, 1H).

Example AA-46

N-{6'-Fluoro-4',9'-dihydro-4-butyl-spiro[cyclohexane-1,1'(3'H)-pyrano[3,4-b]-indol]-4-yl}-n-methylpiperazine, 2-hydroxy-1,2,3-propanetricarboxylate (1:2) (one of two possible diastereoisomers)

Trifluoromethanesulfonic acid (900 mg, 530 µl, 6 mmol) was added, while cooling with ice, to a solution of E-16 (631 mg, 2.5 mmol) and 5-fluorotryptophol F-2 (449 mg, 2.5 mmol) in anhydrous dichloromethane (25 ml), and stirring was carried out over the weekend at room temperature. In order to monitor the conversion, a sample (0.5 ml) was removed and washed with 0.5 N sodium hydroxide solution, and the organic phase was dried with sodium sulfate. When the reaction was complete, 0.5 N sodium hydroxide solution (10 ml) was added to the reaction mixture, stirring was carried out for 2 h at room temperature, the aqueous phase was extracted with dichloromethane (2×20 ml), and the combined organic phases were dried with sodium sulfate and concentrated in vacuo. The crude product was purified by flash chromatography (200 g, 20×5.7 cm) with methanol.

Fraction 1:
Yield: 144 mg (14.0%), white solid
Melting point: 74-81° C.
$^1$H-NMR (DMSO-$d_6$): 0.88 (t, 3H, J=6.7 Hz); 1.14-1.36 (m, 7H); 1.55 (t, 4H, J=12.2 Hz); 1.68 (t, 2H, J=12.2 Hz); 2.04 (t, 2H, J=13.0 Hz); 2.23 (s, 3H); 2.42-2.48 (m, 4H); 2.52-2.57 (m, 3H); 2.62 (t, 2H, J=5.4 Hz); 3.88 (t, 2H, J=5.4 Hz); 6.86 (dt, 1H, J=9.3, 2.6 Hz); 7.12 (dd, 1H, J=9.9, 2.5 Hz); 7.37 (dd, 1H, J=8.7, 4.6 Hz); 10.57 (s, 1H).

In addition, two mixed fractions of fractions 2 & 3 (652 and 213 mg, 84%) were also obtained in the form of a yellow oil; these contain the spiroether and a secondary product in a ratio of about 9:1. A solution of citric acid (928 mg, 4.8 mmol) in hot ethanol (8 ml) is added to a solution of fractions 2 & 3 (796 mg, 1.93 mmol) in boiling ethanol (15 ml). A white precipitate formed after some time and was filtered out after cooling.

Yield: 675 mg (85%), white solid (AA-46)
Melting point: 213-220° C.
$^1$H-NMR (DMSO-$d_6$): 0.90 (t, 3H, J=6.9 Hz); 1.15-1.37 (m, 7H); 1.51-1.63 (m, 4H); 1.71 (t, 2H, J=12.8 Hz); 1.99 (t, 2H, J=13.0 Hz); 2.46-2.80 (m, 16H, superimposed with the DMSO signal); 3.12 (brs, 4H); 3.89 (t, 2H, J=5.4 Hz); 6.89 (dt, 1H, J=9.4, 2.6 Hz); 7.15 (dd, 1H, J=9.8, 2.4 Hz); 7.35 (dd, 1H, J=8.7, 4.5 Hz); 10.49 (s, 1H).
$^{13}$C-NMR (DMSO-$d_6$): 14.0; 22.1; 23.2; 26.5; 26.7 (2C); 29.7 (2C); 34.1; 42.0; 42.8; 44.2 (2C); 54.3; 55.8; 58.7; 71.5; 72.0; 102.5 (d, J=24 Hz); 105.8 (d, J=5 Hz); 108.4 (d, J=26 Hz); 111.8 (d, J=11 Hz); 126.9 (d, J=10 Hz); 132.3; 141.8; 156.8 (d, J=231 Hz); 171.4 (2C); 176.8.

Example AA-47

4',9'-Dihydro-N,N-dimethyl-4-butyl-spiro[cyclohexane-1,1'(3'H)-pyrano[3,4-b]-indol]-4-amine, 2-hydroxy-1,2,3-propanetricarboxylate (1:1) less polar diastereoisomer Example AA-47 is the citrate of the non-polar diastereoisomer obtained in Example AA-38 (fraction 1). This citrate was precipitated by the standard method.

Example AA-48

6'-Hydroxy-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate (1:1) non-polar diastereoisomer Indole F-3 (2.17 g, 12.2 mmol) and ketone E-2 (2.37 g, 12.2 mmol) were placed in abs. dichloromethane (100 ml), under argon; TMS triflate (2.37 ml, 14.4 mmol) in dichloromethane (5 ml) was added, while cooling with ice, and stirring was carried out for 30 min. at RT. The mixture was stirred for a further 16 h at RT. For working up, H$_2$O (85 ml) and K$_2$CO$_3$ (1.90 g) were added, and stirring was carried out for 20 min. at RT. The phases were separated. The aqueous phase was extracted with dichloromethane (2×40 ml). The organic phase was dried over Na$_2$SO$_4$ and concentrated in vacuo. The residue was purified by flash chromatography with CHCl$_3$/MeOH (9:1, 1:1, MeOH).

Yield: non-polar diastereoisomer 1.12 g (26%)
polar diastereoisomer 0.911 g (21%)
The resulting non-polar diastereoisomer (991 mg, 2.78 mmol) was dissolved in hot ethanol, and citric acid (529 mg, 2.78 mmol) dissolved in ethanol (5 ml) was added. The resulting precipitate was filtered out with suction and dried in vacuo. 567 mg (38%)

Melting point: 240-241° C.
$^1$H-NMR (DMSO-$d_6$): 0.92 (3H, t); 1.29 (4H, m); 1.46 (2H, m); 1.75 (4H, t); 1.85 (2H, t); 2.10 (2H, m); 2.54-2.69 (10H, m); 3.87 (2H; t); 6.54 (1H, d); 6.68 (1H, s); 7.16 (1H, d); 8.51 (1H, s, OH); 10.53 (1H, s).
$^{13}$C-NMR (DMSO-$d_6$): 13.91; 22.20; 23.05; 25.90; 26.29; 29.29; 30.65; 37.20; 44.44; 59.06; 60.52; 71.28; 72.08; 101.80; 104.34; 110.52; 111.58; 127.02; 130.11; 139.56; 150.27; 172.05; 177.47.

Example AA-49

6'-Hydroxy-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate (1:1) more polar diastereoisomer The more polar diastereoisomer obtained in Example AA-48 (900 mg, 2.52 mmol) was dissolved in hot ethanol/dioxane (5 ml, 30 ml) (poorly soluble). Citric acid (480 mg, 2.52 mmol) was then dissolved in hot ethanol (5 ml) and added. The mixture was cooled to RT; only a small amount of precipitate formed, so ether was added. The resulting precipitate was filtered out with suction and dried in vacuo.

: 874 mg (63%)

Melting point: 160-170° C.

$^1$H-NMR (DMSO-d$_6$): 0.97 (3H, t); 1.43 (4H, m); 1.65 (2H, m); 1.92 (9H, m); 2.51-2.67 (10H, m); 3.88 (2H; t); 6.58 (1H, d); 6.70 (1H, s); 7.12 (1H, d); 8.56 (1H, s, OH); 10.63 (1H, s).

$^{13}$C-NMR (DMSO-d$_6$): 14.00; 22.09; 22.68; 24.48; 24.74; 28.32; 30.91; 37.46; 44.27; 59.13; 64.84; 70.64; 71.1608; 101.96; 104.69; 110.80; 111.17; 127.03; 129.96; 138.62; 150.36; 171.21; 176.86.

Example AA-50

6'-Fluoro-4',9'-dihydro-N,N-dimethyl-4-cyclopentyl-methyl-spiro[cyclohexane 1,1'(3'H)-pyrano[3,4-b]indol]-4-amine, 2-hydroxy-1,2,3-propanetricarboxylate (2:1) one of two possible diastereoisomers The ketone E-17 (223 mg, 1.0 mmol) and 5-fluoro-tryptophol (179 mg, 1.0 mmol) were dissolved in abs. dichloromethane (10 ml); methanesulfonic acid (0.1 ml, 1.5 mmol) was added, under argon, and stirring was carried out for 3 d at RT. After addition of 1N NaOH (10 ml) and CH$_2$Cl$_2$ (20 ml), stirring was continued for a further 10 min., the phases were separated, the aqueous phase was extracted twice with CH$_2$Cl$_2$, and the combined organic phases were washed with water, dried (Na$_2$SO$_4$) and concentrated in vacuo. The residue that remained was separated by flash chromatography with CHCl$_3$/MeOH (20:1). 388 mg of solid were isolated which, according to NMR, was present in salt form; it was dissolved in CH$_2$Cl$_2$, washed with 1N NaOH solution, dried over Na$_2$SO$_4$ and concentrated in vacuo.

Yield: 310 mg (81%), only 1 diastereoisomer formed $^1$H-NMR (DMSO-d$_6$): 1.16 (2H, m); 1.51-1.84 (14H, m); 2.05 (2H, m); 2.45 (5H, m); 2.74 (6H, s); 3.90 (2H, m); 6.87 (1H, t); 7.17 (1H, m); 7.26 (1H, m); 8.44 (1H, bs); 11.5 (1H, bs)

The resulting amine (310 mg, 0.81 mmol) was dissolved in hot ethanol (10 ml), and a solution of citric acid (155 mg, 0.81 mmol) in hot ethanol (5 ml) was added. After standing in a refrigerator for 2 hours, the resulting solid was filtered out with suction and dried in vacuo.

Yield: 316 mg (81%), hemicitrate formed.

Melting point: 222-223° C.

$^1$H-NMR (DMSO-d$_6$): 1.11 (2H, m); 1.48-1.98 (15H, m); 2.15 (2H, m); 2.58 (6H, s); 2.65 (11H, m); 3.89 (2H, m); 6.83 (1H, m); 7.15 (1H, m); 7.37 (1H, m); 10. (1H, bs); 11.01 (1H, s), hemicitrate.

$^{13}$C-NMR (DMSO-d$_6$): 20.1; 24.6; 26.3; 29.2; 34.4; 35.6; 36.9; 44.2; 59.1; 61.6; 71.2; 72.5; 102.5; 105.6; 108.2; 112.2; 126.5; 132.3; 141.1; 155.6; 157.9; 172.1; 177.3.

Example AA-51

2',3',4',9'-Tetrahydro-N,N-dimethyl-4-butyl-2'-(2-phenylethenecarbonyl)-spiro[cyclohexane-1,1'(1'H)-pyrido[3,4-b]indol]-4-amine, 2-hydroxy-1,2,3-propanetricarboxylate (2:1) less polar diastereoisomer Cinnamic acid chloride (441 mg, 2.65 mmol) was dissolved in abs. tetrahydrofuran (30 ml), under argon, and the free base of the less polar spiroamine prepared in Example AA-9 (300 mg, 0.88 mmol), dissolved in abs. tetrahydrofuran (15 ml), was added at room temperature, in the course of 20 min. Vigorous precipitation occurred. After a reaction time of 1.5 h, the reaction mixture was diluted with water (10 ml); 1N sodium hydroxide solution (10 ml) was added, while cooling with ice, and stirring was then carried out for 2 h. Tetrahydrofuran was removed in vacuo. A solid precipitated and was separated by filtration and washed with water (3×10 ml). The crude product (408 mg) was separated by chromatography [silica gel 60 (50 g); ethyl acetate (500 ml)]. The less polar amide was obtained in the form of a colorless solid in a yield of 76% (314 mg).

The resulting less polar amide (296 mg, 0.63 mmol) was suspended at 80° C. in ethanol (14 ml), and an ethanolic solution (3 ml) of citric acid (133 mg, 0.69 mmol) was added. On cooling to room temperature, a solid precipitated from the clear solution. Stirring was carried out for 16 h at room temperature. The mixture was stored for 2 h at 5° C. The colorless solid was separated by filtration and washed with diethyl ether (3×3 ml). The less polar citrate AA-51 was thus obtained in a yield of 85% (302 mg) in the form of the hemicitrate having a melting point of 154-157° C.

$^{13}$C-NMR (101 MHz, DMSO-D$_6$) d ppm: (less polar diastereoisomer) 13.9, 22.2, 23.0, 26.2, 27.5, 29.5, 30.6, 37.3, 42.4, 44.0, 59.0, 71.6, 105.9, 111.3, 117.5, 118.4, 120.6, 123.1, 126.2, 127.8, 128.7, 129.3, 135.1, 135.5, 139.9, 140.2, 169.4, 171.4, 176.6

Example AA-52

2',3',4',9'-Tetrahydro-N,N-dimethyl-4-butyl-2'-(2-phenylethenecarbonyl)-spiro[cyclohexane-1,1'(1'H)-pyrido[3,4-b]indol]-4-amine, 2-hydroxy-1,2,3-propanetricarboxylate (1:1) more polar diastereoisomer Cinnamic acid chloride (C, 441 mg, 2.65 mmol) was dissolved in abs. tetrahydrofuran (30 ml), under argon, and the free base of the more polar spiroamine prepared in Example AA-9 (300 mg, 0.88 mmol), dissolved in abs. tetrahydrofuran (15 ml), was added at room temperature, in the course of 20 min. Slight precipitation occurred. After a reaction time of 1.5 h, the reaction mixture was diluted with water (10 ml); 1N sodium hydroxide solution (10 ml) was added, while cooling with ice, and stirring was carried out for 1 h. Tetrahydrofuran was removed in vacuo. A solid precipitated and was separated by filtration and washed with water (3×10 ml). The crude product (384 mg) was separated by chromatography [silica gel 60 (50 g); ethyl acetate/methanol 1:4 (750 ml)]. The more polar amide was obtained in the form of a beige-colored solid in a yield of 43% (177 mg).

$^{13}$C-NMR (101 MHz, CDCl$_3$) d ppm: (more polar diastereoisomer) 14.0, 22.4, 23.5, 25.9, 27.3, 31.5, 31.6, 37.8, 43.3, 58.8, 106.7, 111.8, 117.6, 119.3, 121.6, 122.1, 126.6, 127.7, 128.8, 129.6, 135.0, 136.0, 138.8, 141.9, 170.9

The resulting more polar amide (157 mg, 0.334 mmol) was dissolved in ethanol (5 ml), and an ethanolic solution (2 ml) of citric acid (72 mg, 0.37 mmol) was added. Stirring was carried out for 16 h at room temperature, whereupon no precipitation was observed. The mixture was concentrated and taken up in ethanol (2 ml), and diethyl ether (30 ml) was added slowly. After 1.5 h, a colorless solid was separated by filtration and washed with diethyl ether (3×3 ml). The polar citrate AA-52 was thus obtained in a yield of 73% (161 mg).

Comparison Tests on Solubility:

In order to determine the solubilities of the compounds, a series of tests were carried out on the basis of the dilution of a solution of 20 mg/ml in DMSO with an aqueous buffer solution. As pharmaceutical compositions pass through the digestive tract, they are exposed to different pH values. In the stomach, pH values of from 1 to 3 are expected, and following the gastric passage in the intestine, pH values of from 6 to 8 are to be expected. Because solubilities can be pH-dependent, aqueous buffers were used at different pH values (pH 1, 100 mM HCl; pH 2, 10 mM HCl; pH 4, 50 mM citric acid, titrated with 1N NaOH; pH 6, 50 mM sodium citrate, titrated with 1N HCl; pH 7, 50 mM Tris.HCl; pH 8, Tris.HCl), which maintained the established pH values at room temperature in the final solution.

Because DMSO in an increasing concentration promotes the formation of metastable supersaturated aqueous solutions, the stock solutions were diluted 1:100 in aqueous buffer. The solutions were shaken for at least 15 hours in closed vessels. 10 μl of DMSO stock solution were thereby diluted in 990 μl of aqueous buffer and in suitable vessels (e.g. Eppendorf vessels) so that the concentration was constant at 1% v/v. The solutions were then centrifuged off and samples of the clear supernatant were transferred to sample vessels which contained two equivalents of 50% acetonitrile in 0.1N HCl.

The calibration solutions were prepared by diluting the DMSO stock solutions in methanol (1:100). From these dilutions, further dilutions in methanol were prepared (1:100, 1:200, 1:400 and 1:800). Samples were analysed by RP-HPLC with UV detection. Linear calibration equations were derived by regression analysis, generally with correlation coefficients of above 0.95. With the aid of the experimentally determined calibration equations, the concentrations of the compounds in the buffer solutions were determined. Maximum concentrations of 200 μg/ml of substance in buffer could be determined by the described experiment. Higher solubilities could not be quantified.

The correlation between solubility and the variation of $R^3$ was shown by the following compounds.

$R^1$, $R^2$=$CH_3$; $R^5$, $R^6$, $R^7$, $R^9$, $R^{10}$=H, $R^8$=F, X=O

| Example | $R^3$ | Solubility |
|---|---|---|
| AA-8 | (isobutyl with $R^8$ = OH) | 200 μg/ml at pH 1-9 |
| AA-23 | (isobutoxy, -CH₂-O-CH(CH₃)₂) | About 180 μg/ml at pH 1-7 |
| AA-5 | (isobutyl) | 2.9 μg/ml (pH 1); 17.7 μg/ml (pH 2); 5.9 μg/ml (pH 4); 8.7 μg/ml (pH 6); 3.3 μg/ml (pH 7); 0.2 μg/ml (pH 8) |
| AA-2 | (isopropyl) | About 30 μg/ml at pH 1-7 |
| AA-22 | (isobutoxy); $R^8$ = H | 197.6 μg/ml (pH 1); 154.2 μg/ml (pH 2); 154.0 μg/ml (pH 4); 176.7 μg/ml (pH 6); 153.5 μg/ml (pH 7); 46.4 μg/ml (pH 8); 2.1 μg/ml (pH 9) |
| V-1 | (phenyl) | 1.9 μg/ml (pH 2); 0.4 μg/ml (pH 6); 0.8 μg/ml (pH 7), 0.9 μg/ml (pH 8); 0.04 μg/ml (pH 9) |

-continued

| Example | R³ | Solubility |
|---|---|---|
| V-2 | thiophen-2-yl | >5 µg/ml |
| V-3 | phenyl; R¹ = H | 2.7 µg/ml (pH 1), 2.8 µg/ml (pH 2); 1.7 µg/ml (pH 4), 1.5 µg/ml (pH 6), 0.4 µg/ml (pH 7); 0.4 µg/ml (pH 8); 0.4 µg/ml (pH 9) |
| V-4 | phenyl; R⁸ = OH | 1.9 µg/ml (pH 1); 6.4 µg/ml (pH 4); 3.8 µg/ml (pH 6); 1.7 µg/ml (pH 7); 5.1 µg/ml (pH 8); 0.5 µg/ml (pH 9) |
| V-5 | thiophen-2-yl; R⁸ = OH | 1.9 µg/ml (pH 1); 3.1 µg/ml (pH 4); 3.2 µg/ml (pH 7); 2.0 µg/ml (pH 8); 0.6 µg/ml (pH 9) |

The compounds of the invention exhibit an extraordinarily high affinity for the ORL1 or µ-opioid receptor. The affinity is of the same order of magnitude as that of the two comparison compounds. However, they have higher solubility.

Between pH 1 and pH 8, a slight pH-dependence of the solubility was observed. Below pH 8, the solubility of the compounds falls.

Tests of the Effectiveness of the Compounds According to the Invention:

The data mentioned in the following assays and models are summarized in Table 1.

Measurement of ORL1 Binding

The cyclohexane compounds corresponding to formula I were investigated in a receptor binding assay with $^3$H-nociceptin/orphanin FQ with membranes of recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 µg of membrane protein per 200 µl batch in 50 mM Hepes, pH 7.4, 10 mM $MgCl_2$ and 1 mM EDTA. The binding to the ORL1 receptor was determined using in each case 1 mg of WGA-SPA beads (Amersham-Pharmacia, Freiburg), by incubation of the batch for one hour at room temperature and subsequent measurement in a Trilux scintillation counter (Wallac, Finland). The affinity is indicated in Table 1 as the nanomolar $K_i$ value or % inhibition at c=1 µM.

Measurement of µ Binding

The receptor affinity for the human µ-opiate receptor was determined in a homogeneous batch on microtitre plates. To that end, serial dilutions of the particular substituted spirocyclic cyclohexane compound to be tested were incubated for 90 minutes at room temperature with a receptor membrane preparation (15-40 µg of protein per 250 µl of incubation batch) of CHO-K1 cells, which express the human µ-opiate receptor (RB-HOM receptor membrane preparation from NEN, Zaventem, Belgium), in the presence of 1 nmol/liter of the radioactive ligand [$^3$H]-naloxone (NET719, NEN, Zaventem, Belgium) and 1 mg of WGA-SPA beads (wheat-germ agglutinin SPA beads from Amersham/Pharmacia, Freiburg, Germany) in a total volume of 250 µl. The incubation buffer used was 50 mmol/liter of Tris-HCl supplemented with 0.05 wt. % sodium azide and with 0.06 wt. % bovine serum albumin. In order to determine non-specific binding, 25 µmol/liter of naloxone were additionally added. When the ninety-minute incubation time was complete, the microtitre plates were centrifuged off for 20 minutes at 1000 g and the radioactivity was measured in a β-counter (Microbeta-Trilux, PerkinElmer Wallac, Freiburg, Germany). The percentage displacement of the radioactive ligand from its binding to the human µ-opiate receptor at a concentration of the test substances of 1 µmol/liter was determined and stated as the percentage inhibition (% inhibition) of specific binding. In some cases, starting from the percentage displacement, $IC_{50}$ inhibitory concentrations, which effect 50% displacement of the radioactive ligand, were calculated by means of different concentrations of the compounds corresponding to formula I to be tested. Ki values for the test substances were obtained by conversion using the Cheng-Prusoff equation.

Analgesia Test in the Tail-Flick Test in the Mouse

The mice were each placed individually into a test cage and the base of the tail was exposed to the focused heat ray of an electric lamp (tail-flick type 50/08/1.bc, Labtec, Dr. Hess). The intensity of the lamp was adjusted so that the time from switching on of the lamp to the sudden twitching away of the tail (latency of pain) in untreated mice was from 3 to 5 seconds. Before administration of the solutions comprising the compound according to the invention, or of the particular comparison solutions, the mice were pre-tested twice in the course of five minutes and the mean of those measurements was calculated as the pre-test mean.

The solutions of the compound corresponding to formula I according to the invention and the comparison solutions were then administered intravenously. Pain measurement was carried out in each case 10, 20, 40 and 60 minutes following the intravenous administration. The analgesic activity was determined as the increase in the latency of pain (% of the maximum possible antinociceptive effect) according to the following formula:

$$[(T_1-T_0)/(T_2-T_0)]\times 100$$

where time $T_0$ is the latency before administration, time $T_1$ is the latency after administration of the active ingredient combination, and time $T_2$ is the maximum exposure time (12 seconds). In two cases the test was carried out analogously on rats.

TABLE 1

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-1 | | One of 2 possible diastereoisomers | 0.0031 | 0.0005 | 90% (100 μg/kg) |
| AA-2 | | Less polar diastereoisomer | 00120 | 0.0003 | n.d. |
| AA-3 | | One of 2 possible diastereoisomers | 0.0012 | 0.0003 | n.d. |
| AA-4 | | One of 2 possible diastereoisomers | 0.0002 | 0.0005 | 75% |
| AA-5 | | One of 2 possible diastereoisomers | 0.0016 | 0.0009 | 60% |
| AA-6 | | One of 2 possible diastereoisomers | 0.0009 | 0.0007 | Rat $ED_{50}$ = 11 μg/kg |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-7 | | One of 2 possible diastereoisomers | 0.0025 | 0.0002 | n.d. |
| AA-8 | | One of 2 possible diastereoisomers | 0.2600 | 0.0250 | Rat $ED_{50}$ = 385 μg/kg |
| AA-9 | | Less polar diastereoisomer | 0.0001 | 0.0003 | n.d. |
| AA-10 | | Less polar diastereoisomer | 0.0002 | 0.0003 | 75% |
| AA-11 | | Less polar diastereoisomer | 0.0006 | 0.0012 | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-12 | | Less polar diastereoisomer | 0.0015 | 0.0009 | n.d. |
| AA-13 | | Less polar diastereoisomer | 0.0006 | 0.0006 | n.d. |
| AA-14 | | Less polar diastereoisomer | 0.0002 | 0.0003 | n.d. |
| AA-15 | | More polar diastereoisomer | 0.0002 | 0.0004 | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-16 | 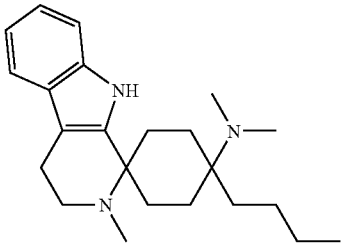 [SMILES: CCCCC1(N(C)C)CCC2(CC1)c1[nH]c3ccccc3c1CCN2C] | Less polar diastereoisomer | 0.0002 | 0.0004 | n.d. |
| AA-17 | 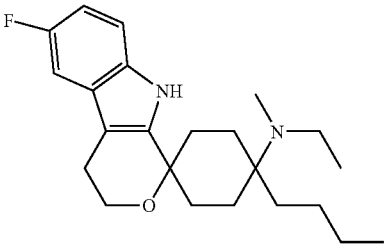 [SMILES: CCCCC1(N(C)CC)CCC2(CC1)OCCc1c2[nH]c2ccc(F)cc12] | One of 2 possible diastereoisomers | 0.0066 | 0.0018 | n.d. |
| AA-18 | 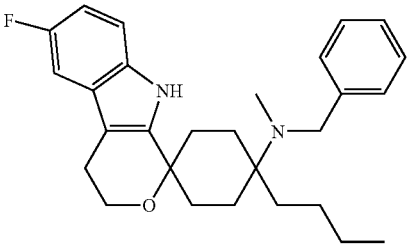 [SMILES: CCCCC1(N(C)Cc2ccccc2)CCC2(CC1)OCCc1c2[nH]c2ccc(F)cc12] | — | — | 0.3733 | n.d. |
| AA-19 | 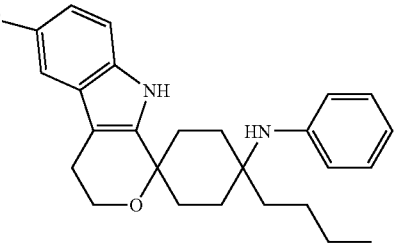 | One of 2 possible diastereoisomers | — | 1.9400 | n.d. |
| AA-20 | 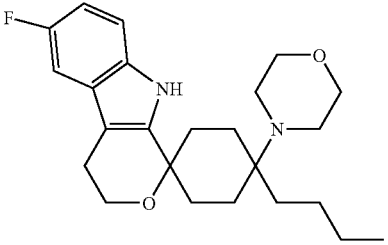 | Less polar diastereoisomer | — | 36% | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-21 | | | | 36% | n.d. |
| AA-22 | | One of 2 possible diastereoisomers | 0.0006 | 0.0002 | n.d. |
| AA-23 | | Less polar diastereoisomers | 0.0050 | 0.0003 | 100% (46.4 μg/kg) |
| AA-24 | | Less polar diastereoisomer | 0.0003 | 0.0003 | n.d. |
| AA-25 | | One of 2 possible diastereoisomers | 0.0032 | 0.0002 | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-26 | 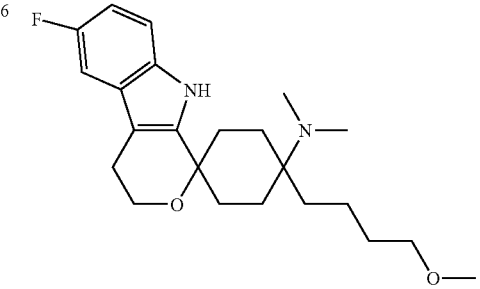 | More polar diastereoisomer | 0.0243 | 0.0004 | n.d. |
| AA-27 | 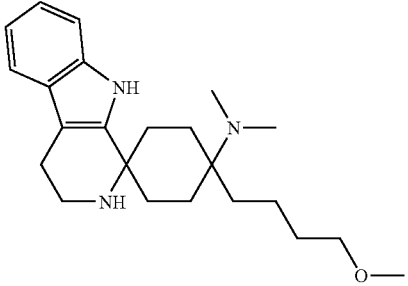 [SMILES: COCCCCC1(N(C)C)CCC2(CC1)NCCc1c2[nH]c2ccccc12] | Less polar diastereoisomer | 0.0014 | 0.0004 | n.d. |
| AA-28 | 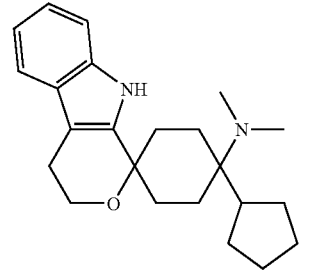 [SMILES: CN(C)C1(C2CCCC2)CCC2(CC1)OCCc1c2[nH]c2ccccc12] | One of 2 possible diastereoisomers | 0.0001 | 0.0006 | 90% |
| AA-29 | 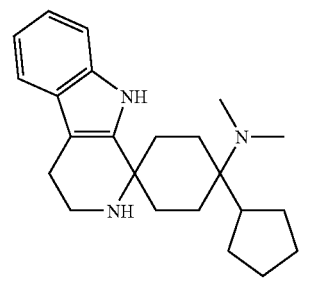 [SMILES: CN(C)C1(C2CCCC2)CCC2(CC1)NCCc1c2[nH]c2ccccc12] | One of 2 possible diastereoisomers | 0.0001 | 0.0002 | n.d. |
| AA-30 | 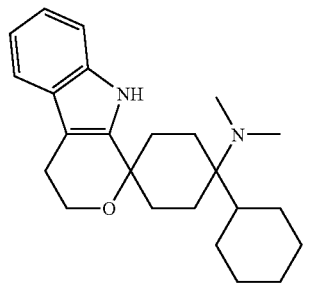 [SMILES: CN(C)C1(C2CCCCC2)CCC2(CC1)OCCc1c2[nH]c2ccccc12] | One of 2 possible diastereoisomers | 0.0004 | 0.0007 | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-31 | | One of 2 possible diastereoisomers | 0.0012 | 0.0015 | n.d. |
| AA-32 | | One of 2 possible diastereoisomers | 0.0001 | 0.0002 | n.d. |
| AA-33 | | More polar diastereoisomer | 0.2500 | 0.3400 | n.d. |
| AA-34 | | More polar diastereoisomer | | 1.0767 | n.d. |
| AA-35 | | More polar diastereoisomer | | 26% | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-36 | | More polar diastereoisomer | 1.7500 | 0.0633 | n.d. |
| AA-37 | | More polar diastereoisomer | | 0.2750 | n.d. |
| AA-38 | | More polar diastereoisomer | 1.2600 | 0.3650 | n.d. |
| AA-39 | | More polar diastereoisomer | 3.7900 | 1.0433 | n.d. |
| AA-40 | | One of 2 possible diastereoisomers | | 0.3167 | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-41 | | | | 3.8033 | n.d. |
| AA-42 | | One of 2 possible diastereoisomers | | 53% | n.d. |
| AA-43 | | One of 2 possible diastereoisomers | 47% | 94% | n.d. |
| AA-44 | | Less polar diastereoisomer | | 42% | n.d. |
| AA-45 | | More polar diastereoisomer | | 44% | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-46 | | One of 2 possible diastereoisomers | | 34% | n.d. |
| AA-47 | | Less polar diastereoisomer | 0.0003 | 0.0006 | n.d. |
| AA-48 | | Less polar diastereoisomer | 98% | 0.0005 | n.d. |
| AA-49 | | More polar diastereoisomer | 27% | 1.3 | n.d. |
| AA-50 | | One of 2 possible diastereoisomers | 0.0052 | 0.0027 | n.d. |

TABLE 1-continued

| Example | Structure without salt For salt form see example description | Diastereoisomer | Ki (ORL1) mean [μM] Solid or % inhibition [1 μM] | Ki (μ) mean [μM] Solid or % inhibition [1 μM] | Tail-flick mouse i. v. % inhibition [10 μg/kg] |
|---|---|---|---|---|---|
| AA-51 | | Less polar diastereoisomer | 0.0043 | 0.0030 | n.d. |
| AA-52 | | More polar diastereoisomer | 0.6600 | 0.1200 | n.d. |

Parenteral Solution of a Spirocyclic Cyclohexane Compound According to the Invention 38 g of one of the spirocyclic cyclohexane compounds according to the invention, here Example 3, are dissolved in 1 liter of water for injection purposes at room temperature and then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A spirocyclic cyclohexane compound corresponding to formula I:

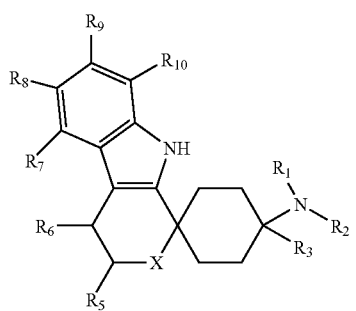

87 wherein
R¹ and R² each independently represent H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl, unsubstituted or mono- or poly-substituted;

R³ represents $C_{1-8}$-alkyl, in each case saturated or unsaturated, branched or unbranched, mono- or poly-substituted or unsubstituted;

R⁵ represents H;

R⁶ represents H;

R⁷, R⁸, R⁹ and R¹⁰ each independently represent H, F, Cl, Br, I, $NO_2$, $CF_3$, OH, $OCH_3$, $NH_2$, COOH, $COOCH_3$, $NHCH_3$, thienyl, pyrimidinyl, pyridyl, $N(CH_3)_2$, or $C_{1-5}$-alkyl, branched or unbranched, unsubstituted or mono- or poly-substituted;

X represents O, S, SO or $SO_2$;

wherein "alkyl substituted" or "cycloalkyl substituted" denotes the replacement of one or more hydrogens by F, Cl, Br, I, —CN, $CH_3$, $C_2H_5$, $NH_2$, $NO_2$, SH, cyclopentyl, cyclohexyl, $CF_3$ OH, $OCH_3$, $OC_2H_5$ or $N(CH_3)_2$; and "aryl substituted" or "heteroaryl substituted" denotes the replacement of one or more hydrogens by F, Cl, Br, I, CN, $CH_3$, $C_2H_5$, $NH_2$, $NO_2$, SH, $CF_3$, OH, $OCH_3$, $OC_2H_5$ or $N(CH_3)_2$, or a physiologically acceptable salt thereof.

2. A compound according to claim 1, wherein said compound is in the form of an isolated stereoisomer.

3. A compound according to claim 1, wherein said compound is in the form of a mixture of stereoisomers in any mixing ratio.

4. A compound according to claim 3, wherein said mixture is a racemic mixture.

5. A compound according to claim 1, wherein R¹ and R² each independently represent H, $C_{1-5}$-alkyl, branched or unbranched, saturated or unsaturated, unsubstituted or mono- or poly-substituted, or phenyl or benzyl, unsubstituted or mono- or poly-substituted.

6. A compound according to claim 5, wherein R¹ and R² represent H or $CH_3$, wherein R¹ and R² do not simultaneously denote $CH_3$.

7. A compound according to claim 1, wherein R³ represents ethyl, n-propyl, 2-propyl, allyl, n-butyl, isobutyl, sec-butyl, tert-butyl, n-pentyl, isopentyl, neopentyl, n-hexyl, methylcyclopentyl, or methylcyclohexyl, in each case unsubstituted or mono- or poly-substituted by OH, $OCH_3$ or $OC_2H_5$.

8. A compound according to claim 1, wherein R³ represents ethyl, n-propyl, 2-propyl, allyl, n-butyl, isobutyl, sec-butyl, tert-butyl, n-pentyl, isopentyl, neopentyl, or n-hexyl, in each case unsubstituted or mono- or poly-substituted by OH, $OCH_3$ or $OC_2H_5$.

9. A compound according to claim 1, wherein X represents O.

10. A compound according to claim 1, selected from the group consisting of:

4',9'-dihydro-N,N-dimethyl-4-ethyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-ethyl-spiro[cyclohexane-1,1'(3'H)-pyrano[3,4-b]indol]-4-amine, 2-hydroxy-1,2,3-propanetricarboxylate 4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate

88

6'-fluoro-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-hydroxy-4',9'-dihydro-N,N-dimethyl-4-butyl-spiro[cyclohexane-1,1'(3'H)-pyrano[3,4-b]indol]-4-amine, 2,2,2-trifluoroacetate 6'-hydroxy-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-fluoro-4',9'-dihydro-N-ethyl-N-methyl-4-butyl-spiro[cyclohexane-1,1'(3'H)-pyrano[3,4-b]indol]-4-amine, 2-hydroxy-1,2,3-propanetricarboxylate 6'-fluoro-4',9'-dihydro-N-benzyl-N-methyl-4-butyl-spiro[cyclohexane-1,1'(3'H)-pyrano[3,4-b]indol]-4-amine 6'-fluoro-4',9'-dihydro-N-phenyl-4-butyl-spiro[cyclohexane-1,1'(3'H)-pyrano[3,4-b]indol]-4-amine 4',9'-dihydro-N,N-dimethyl-4-methoxypropyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-methoxypropyl-spiro[cyclohexane-1,1'(3'H)-pyrano[3,4-b]indol]-4-amine, 2-hydroxy-1,2,3-propanetricarboxylate 4',9'-dihydro-N,N-dimethyl-4-(4-methoxybutyl)-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-(4-methoxybutyl)-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-ethyl-spiro[cyclohexane-1,1'(3'H)-pyrano[3,4-b]indol]-4-amine, 2-hydroxy-1,2,3-propanetricarboxylate 4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-fluoro-4',9'-dihydro-N-benzyl-4-allyl-spiro[cyclohexane-1,1'(3'H)-pyrano[3,4-b]indol]-4-amine, 2-hydroxy-1,2,3-propanetricarboxylate 6'-fluoro-4',9'-dihydro-N-phenyl-4-allyl-spiro[cyclohexane-1,1'(3'H)-pyrano[3,4-b]indol]-4-amine 6'-fluoro-4',9'-dihydro-N-(4-methoxybenzyl)-4-allyl-spiro[cyclohexane-1,1'(3'H)-pyrano[3,4-b]indol]-4-amine 4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-hydroxy-4',9'-dihydro-N,N-dimethyl-4-butyl-spiro[cyclohexane-1,1'(3'H)-pyrano[3,4-b]indol]-4-amine, 2-hydroxy-1,2,3-propanetricarboxylate 6'-fluoro-4',9'-dihydro-N,N-dimethyl-4-cyclopentylmethyl-spiro[cyclohexane 1,1'(3'H)-pyrano[3,4-b]indol]-4-amine, 2-hydroxy-1,2,3-propanetricarboxylate physiologically acceptable salts thereof, and mixtures thereof.

11. A pharmaceutical composition comprising a compound according to claim 1 and at least one pharmaceutically acceptable carrier or additive.

12. A method of preparing a compound according to claim 1, said method comprising reacting a compound corresponding to formula E with a starting material corresponding to formula F, wherein R¹ to R³ and R⁵ to R¹⁰ have the meanings given in claim 1, according to the equation:

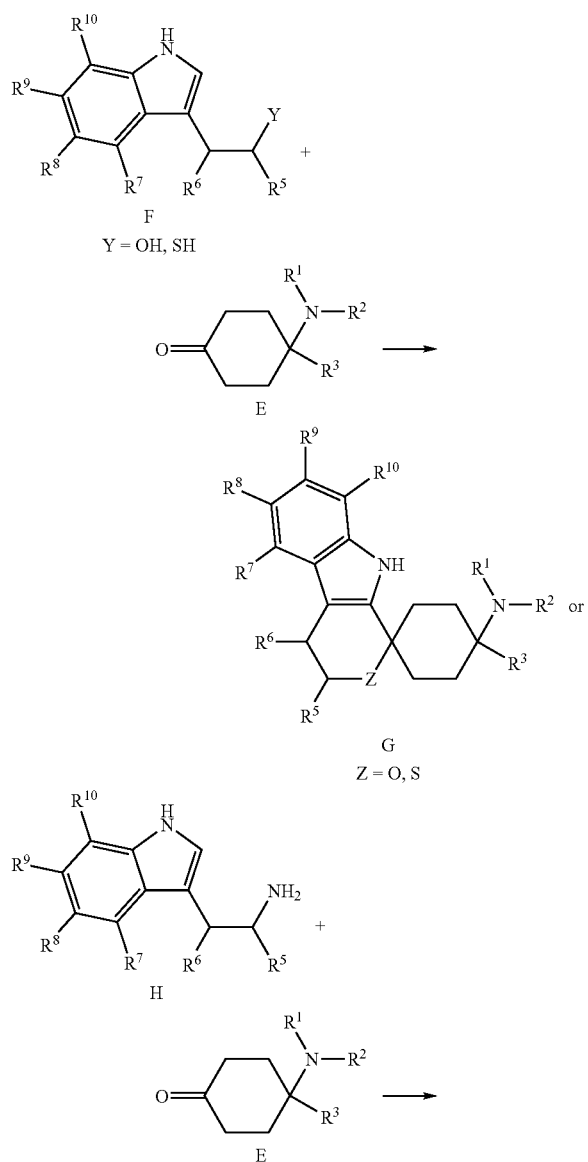

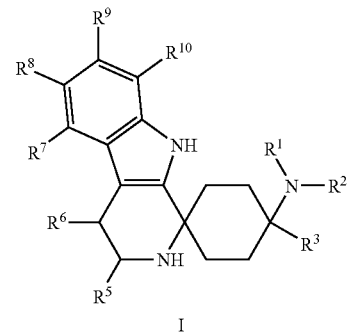

with the addition of acid or a trimethylsilyl ester thereof, in a solvent.

13. A method according to claim 12, wherein said reaction is carried out in a solvent selected from the group consisting of dichloroethane, dichloromethane, chloroform, acetonitrile, diethyl ether, and nitromethane, with addition of trifluoromethanesulfonic acid trimethylsilyl ester, or of an acid selected from the group consisting of trifluoromethanesulfonic acid, acetic acid, phosphoric acid, methanesulfonic acid, and trifluoroacetic acid.

14. A method according to claim 12, wherein X denotes SO or $SO_2$, said method comprising oxidizing a compound of formula I in which X denotes S with an oxidizing agent.

15. A method according to claim 14, wherein said oxidizing agent comprises $H_2O_2$.

16. A method of treating pain in a subject in need thereof, said method comprising administering to said subject a pharmacologically effective amount of a compound according to claim 1.

17. A method according to claim 16, wherein said pain is acute pain, neuropathic pain or chronic pain.

* * * * *